United States Patent
Sahin et al.

(10) Patent No.: US 11,473,085 B2
(45) Date of Patent: *Oct. 18, 2022

(54) METHODS AND COMPOSITIONS FOR DIAGNOSIS AND TREATMENT OF CANCER

(71) Applicants: GANYMED PHARMACEUTICALS AG, Mainz (DE); JOHANNES GUTENBERG-UNIVERSITAT MAINZ, Mainz (DE)

(72) Inventors: Ugur Sahin, Mainz (DE); Özlem Tureci, Mainz (DE); Michael Koslowski, Frankfurt (DE); Gerd Helftenbein, Gemunden (DE); Korden Walter, Wiesbaden (DE); Stefan Woll, Nackenheim (DE); Gabriela-Elena Oprea, Mainz (DE)

(73) Assignees: GANYMED PHARMACEUTICALS GMBH, Mainz (DE); JOHANNES GUTENBERG-UNIVERSITAT MAINZ, Mainz (DE)

( * ) Notice: Subject to any disclaimer, the term of this patent is extended or adjusted under 35 U.S.C. 154(b) by 352 days.

This patent is subject to a terminal disclaimer.

(21) Appl. No.: 16/275,111

(22) Filed: Feb. 13, 2019

(65) Prior Publication Data

US 2019/0169614 A1   Jun. 6, 2019

Related U.S. Application Data

(60) Continuation of application No. 15/726,063, filed on Oct. 5, 2017, now abandoned, which is a division of application No. 13/201,702, filed as application No. PCT/EP2010/001062 on Feb. 19, 2010, now Pat. No. 9,809,815.

(60) Provisional application No. 61/260,135, filed on Nov. 11, 2009, provisional application No. 61/231,843, filed on Aug. 6, 2009, provisional application No. 61/154,167, filed on Feb. 20, 2009.

(30) Foreign Application Priority Data

| Feb. 20, 2009 | (EP) | 09002452 |
| Aug. 6, 2009 | (EP) | 09010164 |
| Nov. 11, 2009 | (EP) | 09014135 |

(51) Int. Cl.
C12N 15/113 (2010.01)
A61K 31/7088 (2006.01)

(52) U.S. Cl.
CPC ........ *C12N 15/113* (2013.01); *A61K 31/7088* (2013.01)

(58) Field of Classification Search
CPC .. C12N 15/113; A61K 31/7088; A61K 39/00; A61P 37/04; A61P 35/04; A61P 35/00; C12Q 1/6886; C12Q 2600/158; G01N 33/57423; G01N 33/57449; G01N 33/68
See application file for complete search history.

(56) References Cited

U.S. PATENT DOCUMENTS

| 4,946,778 A | 8/1990 | Ladner et al. |
| 5,624,821 A | 4/1997 | Winter et al. |
| 5,648,260 A | 7/1997 | Winter et al. |
| 6,121,022 A | 9/2000 | Presla et al. |
| 6,194,551 B1 | 2/2001 | Idusogie et al. |
| 6,277,375 B1 | 8/2001 | Ward |
| 7,431,927 B2 | 10/2008 | Couto et al. |
| 9,321,842 B2 | 4/2016 | Sahin et al. |
| 9,487,584 B2 | 11/2016 | Sahin et al. |
| 9,718,886 B2 | 8/2017 | Sahin et al. |
| 2002/0086356 A1 | 7/2002 | Tuschl |
| 2002/0127584 A1 | 9/2002 | Baker et al. |
| 2003/0017534 A1 | 1/2003 | Buelow et al. |
| 2003/0036635 A1 | 2/2003 | Baker et al. |
| 2003/0118592 A1 | 6/2003 | Ledbetter et al. |
| 2003/0133939 A1 | 7/2003 | Ledbetter et al. |
| 2007/0082345 A1 | 4/2007 | Ota et al. |
| 2007/0207142 A1 | 9/2007 | Crowley et al. |
| 2011/0059469 A1 | 3/2011 | Aburatani et al. |
| 2011/0300144 A1 | 12/2011 | Sahin et al. |
| 2012/0308478 A1 | 12/2012 | Sahin et al. |
| 2013/0183305 A1 | 7/2013 | Sahin et al. |
| 2014/0127219 A1 | 5/2014 | Sahin et al. |
| 2016/0159901 A1 | 6/2016 | Sahin et al. |
| 2016/0222125 A1 | 8/2016 | Sahin et al. |

(Continued)

FOREIGN PATENT DOCUMENTS

| CA | 2379661 | 9/2003 |
| CN | 101212989 | 11/2008 |

(Continued)

OTHER PUBLICATIONS

Ushiku et al. Distinct expression patter of claudin-6, a primitive phenotypic tight junction molecule, in germ cell tumours and visceral carcinomas. Histopathology 61: 1043-1056, 2012.*
"Bunshi Saibo Seibutsugaku Jiten" (Molecular Cell Biology Dictionary), 1stEd., 2002, Tokyo Kagaku Dojin Co., LTD., p. 282, definition of antigen binding site.
"Menekigaku Jiten" (Dictionary of Immunology), 2nd Ed., 2001, Tokyo Kagaku Dojin Co., Ltd., p. 501, Iefinition of humanized antibody.
Brown, et al., "Tolerance to Single, but not Multiple, Amino Acid Replacements in Antibody VH CDR2," J. Immunol. May 1996: 156 (9):3285-91.

(Continued)

*Primary Examiner* — Alana Harris Dent
(74) *Attorney, Agent, or Firm* — Neal, Gerber & Eisenberg LLP; Kevin A. O'Connor

(57) ABSTRACT

The present invention relates to the identification of nucleic acid and amino acid sequences that are characteristic of tumor tissues such as ovarian tumor and lung tumor tissues and which represent targets for therapy or diagnosis of tumor diseases in a subject.

10 Claims, 23 Drawing Sheets

Figure 1:
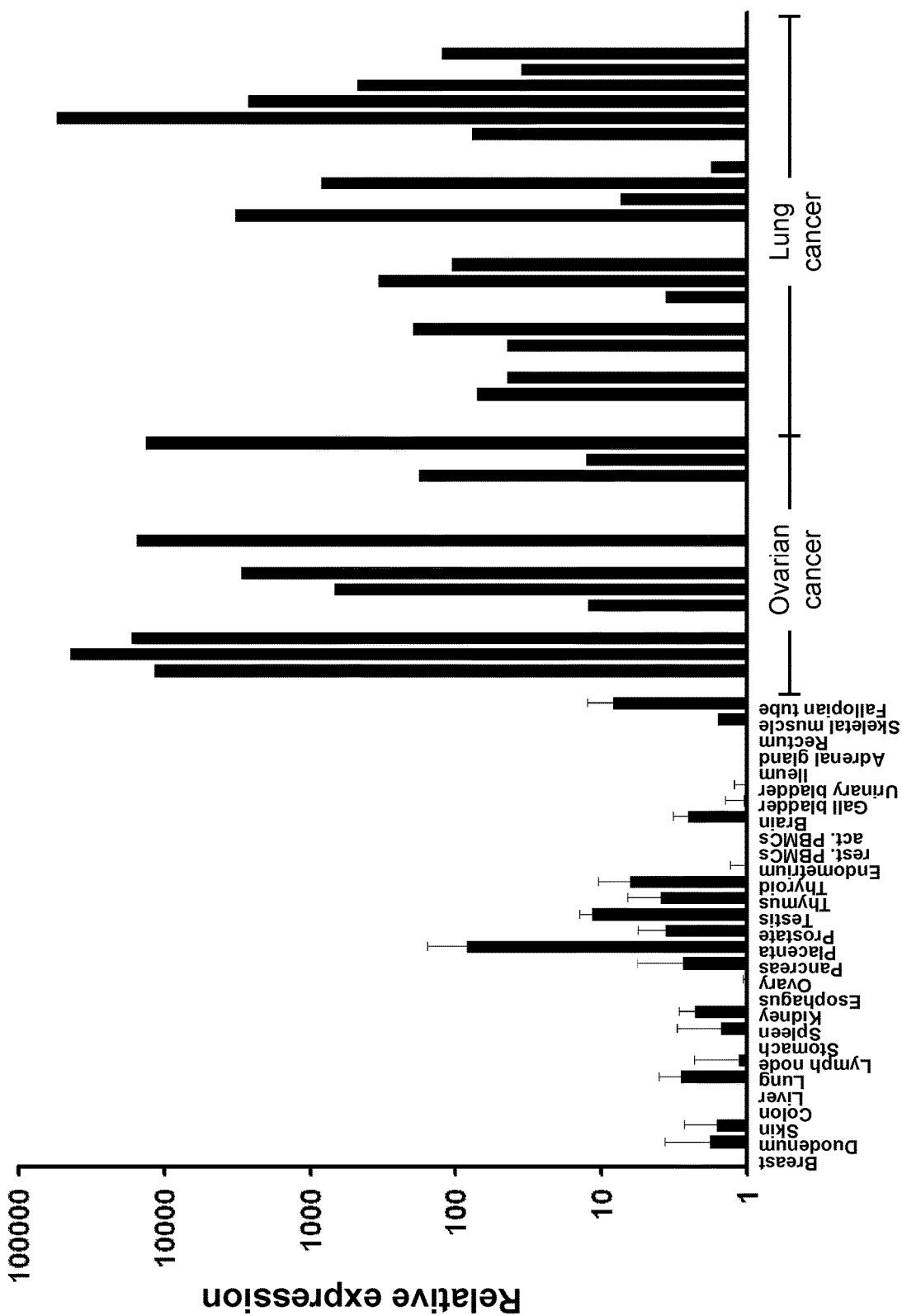

Specification includes a Sequence Listing.

(56) References Cited

U.S. PATENT DOCUMENTS

| | | |
|---|---|---|
| 2016/0264677 A1 | 9/2016 | Sahin et al. |
| 2016/0355604 A1 | 12/2016 | Sahin et al. |
| 2018/0119146 A1 | 5/2018 | Sahin et al. |
| 2018/0142033 A1 | 5/2018 | Sahin et al. |
| 2018/0162938 A1 | 6/2018 | Sahin et al. |

FOREIGN PATENT DOCUMENTS

| | | |
|---|---|---|
| CN | 101312989 | 11/2008 |
| CN | 101687929 | 3/2010 |
| EP | 338841 | 10/1989 |
| EP | 1067182 | 1/2001 |
| EP | 2011886 | 1/2009 |
| EP | 2241578 | 10/2010 |
| EP | 2322555 | 5/2011 |
| JP | H11503014 | 3/1999 |
| JP | 2001506275 | 5/2001 |
| JP | 2002536995 | 11/2002 |
| JP | 2004537534 | 12/2004 |
| JP | 2007529416 | 10/2007 |
| JP | 2010178650 | 8/2010 |
| JP | 2011501758 | 1/2011 |
| JP | 2011516580 | 5/2011 |
| JP | 2012512778 | 8/2012 |
| JP | 2012518608 | 8/2012 |
| JP | 2012518609 | 8/2012 |
| RU | 2010133547 | 2/2012 |
| WO | 87/04462 | 7/1987 |
| WO | 89/01036 | 2/1989 |
| WO | 92/04381 | 3/1992 |
| WO | 96/33265 | 10/1996 |
| WO | 96/33739 | 10/1996 |
| WO | 99/24463 | 5/1999 |
| WO | 99/45962 | 9/1999 |
| WO | 00/12708 | 3/2000 |
| WO | 2000/26360 | 5/2000 |
| WO | 00/35937 | 6/2000 |
| WO | 00/73348 | 12/2000 |
| WO | 00/78961 | 12/2000 |
| WO | WO 2000/73348 | 12/2000 |
| WO | 01/51513 | 7/2001 |
| WO | 01/53312 | 7/2001 |
| WO | 01/93983 | 12/2001 |
| WO | 02/00690 | 1/2002 |
| WO | 02/08284 | 1/2002 |
| WO | 02/08288 | 1/2002 |
| WO | 02/43478 | 6/2002 |
| WO | 03/088808 | 10/2003 |
| WO | 2004/030615 | 4/2004 |
| WO | 2004/035607 | 4/2004 |
| WO | 2004/060270 | 7/2004 |
| WO | 2004110363 | 12/2004 |
| WO | 2005/005601 | 1/2005 |
| WO | 2006033664 | 3/2006 |
| WO | 2008/114733 | 9/2008 |
| WO | 2009/025759 | 2/2009 |
| WO | 2009/028663 | 3/2009 |
| WO | 2009/087978 | 7/2009 |
| WO | 2010/043650 | 4/2010 |
| WO | 2010/094499 | 8/2010 |
| WO | 2011/057788 | 5/2011 |
| WO | 2011105551 | 9/2011 |
| WO | 2012/003956 | 1/2012 |
| WO | 2013035824 | 3/2013 |
| WO | 2013/087929 | 6/2013 |
| WO | 2014/015148 | 1/2014 |

OTHER PUBLICATIONS

Vare, et al., "Twist is inversely associated with claudins in germ cell tumors of the testis," APMIS 118: 640-647, published online Jun. 11, 2010.
Adams, G.P. et al., Cancer Res., (2001), vol. 61, pp. 4750-4755.
K. Fujimori et al., J. Nucl. Med., 31: 1191-1198, 1990.
Sharon, J., Proc. Natl. Acad. Sci. USA, (1990), vol. 87, pp. 4814-4817.
David U., et al., "Immunoligic and Chemical Targeting of the Tight-Junction Protein Claudin-6 Eliminates Tumorigenic Human Pluripotent Stem Cells", Natural Communications 2013, vol. 4, Jun. 18, 2013, XP008168176, p. 1992.
Dormeyer, W. et al., "Plasma Membrane Proteomics of Human Embryonic Stem Cells and Human Embroyonal Carcinoma Cells", Journal of Proteome Research, American Chemical Society, Washington, DC., US, vol. 7, XP002599270, Jul. 3, 2008, pp. 2936-2951.
ISR for PCT/EP2014/066330 dated Nov. 17, 2014.
Kwon, M. "Emerging Roles of Claudins in Human Cancer", International Journal of Molecular Science, vol. 14, No. 9, Sep. 4, 2013, XP0055107170, pp. 18148-18180.
Prat, A., et al., "Phenotypic and Molecular Characterization of the Claudin-Low Intrinsic Subtype of Breast Cancer", Breast Cancer Research, Current Science, London, GB, vol. 12, No. 5, Sep. 2, 2010, XP021085380, p. R68.
Trail, P. "Antibody Drug Conjugates as Cancer Therapeutics", Antibodies, M D P I AG, CH, vol. 2, No. 1, Feb. 27, 2013, XPD02725437, pp. 113-129.
Turksen, K. "Claudins and Cancer Stem Cells", Stem Cell Reviews and Reports, Humana Press Inc., New York, vol. 7 No. 4, Apr. 28, 2011, XP019985913, pp. 797-798.
Ushiku T. et al., "Distinct Expression Pattern of Claudin-6, a Primitive Phenotypic Tight Junction Molecule, In Germ Cell Tumours and Visceral Carcinomas", Histopathology, vol. 61, No. 6, Jul. 17, 2012, XP055107355, pp. 1043-1056.
Wang, L., et al, "Claudin 6: A Novel Surface Marker for Characterizing Mouse Pluripotent Stem Cells", Cell Research, vol. 22, No. 6, May 8, 2012, XP055107350, pp. 1082-1085.
Poljak, R. J., et al. (1994) Structure2: 1121-1123.
Anonymous: "Tumor Markers—National Cancer institude", Dec. 7, 2011 (Dec. 7, 2011), Retrieved from the Internet: URL:http://www.cancer.gov/cancertopics/diagnosis-staging/diagnosis/tumor-markers-fact-sheet [retrieved on Mar. 20, 2015].
Extended European Search Report for European Patent Application No. 09002452.2-1212, dated Oct. 22, 2009.
GenBank. Homo sapiens claudin 6 (CLDN6), mRNA NCB I Reference Sequence: NM_021195.4,2014.
Hong Yeon-Hee et al., "Up-regulation of the claudin-6 gene in adipongenesis." Bioscience Biotechnology, and Biochemistry, Nov. 2005, vol. 69, No. 11. pp. 2117-2121, XP002547908.
Huang Yu-Hung et al., "Claudin-3 gene silencing with siRNA suppresses ovarian tumor growth and metastasis." Proceedings of the National Academy of Sciences of the United Slates of America 3, Mar. 2009, vol. 106, No. 9, Feb. 10, 2009, pp. 3426-3430, XP002547909.
IPRP for PCT/EP2010/001062, dated Sep. 1, 2011.
Kuby, Janis Immunology, W. H. Freeman and Company New York, N Y (1992).
Osanai Makoto et al., "Epigenetic silencing of claudin-6 promotes anchorage-independent growth of breast carcinoma cells." Cancer Science Oct. 2007, vol. 98, No. 10, pp. 1557-1562, XP002547907.
Almagaro & Fransson, Frontiers in Bioscience 2008; 13:1619-33.
De Genst et al., Developmental and Comparative Immunology, 2006, 30:187-98.
Barthelemy et al., Journal of Biological Chemistry, 2008, 283:3639-3654.
Choi et al., 2011, Molecular BioSystems, 2011, 7:3327-334.
Griffiths et al., The EMBO Journal, 1993, 12:725-734.
Klimka et al., British Journal of Cancer, 2000, 83:252-260.
Beiboer et al., Journal of Molecular Biology, 2000, 296:833-849.
Kohler, "Immunoglobulin chain loss in hybridoma lines," Proc. Natl. Acad. Sci. USA, vol. 77, No. 4 pp. 2197-2199, Apr. 1980.
Ozturk et al., "Loss of Antibody Productivity During Long-Term Cultivation of a Hybridoma Cell Line in Low Serum and Serum-Free Media," Hybridoma, vol. 9, No. 2, 1990.
Sela-Culang et al., "The structural basis of antibody-antigen recognition," Frontiers in Immunology, vol. 4, Article 302, Oct. 8, 2013.
Wu et al., "Humanization of a Murine Monoclonal Antibody by Simultaneous Optimization of Framework and CDR Residues," Journal of Molecular Biology, 294, 1999.

(56) References Cited

OTHER PUBLICATIONS

Kang et al., "Studies on SP6 promoter using a new plasmid vector that allows gene insertion at the transcription initiation site", Nuc. Acids Res., 15, pp. 2279-2294, Mar. 1987.
Morita et al. (Proc. Natl. Acad. Sci. USA 96: 511-516, Jan. 1999).
NCBI (*Homo sapiens* claudin 6 (CLDN6), mRNA-Nucleotide) Mar. 15, 2015.
Mariuzza el al., "The Structural Basis of Antigen-Antibody Recognilion", Ann. Rev. Biophys. Biophys. Chem. 1987, 16: 139-59.
Padlan et al. (Proceedings of the National Academy of Sciences, 1989, 86:5938-5942).
Pakula A. A. et al., Genetic analysis of protein stability and function. Annu. Rev. Genet., 1989 No. 23, pp. 289-310.
Pascalis et al. (The Journal of Immunology, 2002, 169, 2076-3084).
Robinson, J.R., ed. Sustained and Controlled Release Drug Delivery Systems, Marcel Dekker, Inc., New York, 1978.
Rudikoff et al. (Proceedings of the National Academy of Science USA, 1982, 79:1979).
Satohisa et al. (Experimental Cell Research, 2005: 310:66-78).
Vajdos F. F et al., Comprehensive Functional Maps of the Antigenbinding Site of an Anti-ErbB2 Antibody Obtained with Shotgun Scanning Mutagenesis, J. Mol. Biol., 2002, vol. 320, pp. 415-428.
Benny K.C. Lo Antibody Engineering ISBN: 1-58829-092-1.
Ming-Ming Tsai: "Potential prognostic, diagnostic and therapeutic markers for human gastric cancer", World Journal of Gastroenterology, vol. 20, No. 38, Oct. 14, 2014 (Oct. 14, 2014), p. 13791.
Allard et al, Clin Cancer Res 10: 6897-904, 2004.
Altman et al., Science 274:94-96, 1996.
Anderson et al., 1. Immunol. 143: 1899-1904, 1989.
Azorsa et al., J. Immunol. Methods 229: 35-48, 1999.
Beadling et al. Nature Medicine 12:1208 (2006).
Clark, W.R. (1986), The Experimental Foundations of Modern immunology.
Dunbar et al., Curro Bioi. 8:413-416, 1998.
Gardsvoll, J. Immunol. Methods 234:107-116, 2000.
Goodman and Gilman, "The Pharmacological Basis of Therapeutics", 8th Edition, 1990, McGraw-Hill, Inc., in particular Chapter 52 Antineoplastic Agents Paul Calabresi and Bruce A. Chabner.
Harlow et al. Antibodies: A Laboratory Manual ISBN: 0879693142, Jan. 1, 1998.
Harlow et al. Using Antibodies: A Laboratory Manual: Portable Protocol No. ISBN 0879695447.
Ossendorp et al., Immunol Lett. 74:75-9, 2000.
Ossendorp et al., J. Exp. Med. 187:693-702, 1998.
Pearson and Lipman, 1988, Proc. Natl Acad. Sci. USA 85, 2444.
Sambrook et al. Molecular Cloning: A Laboratory Manual, 2nd Edition, Cold Spring Harbor Laboratory press, Cold Spring Harbor, New York, 1989, Ausubel et al., Current Protocols in Molecular Biology, Editors, John Wiley & Sons, Inc., New York.
Science 268: 1432-1434, 1995.
Shepherd et al. Monoclonal Antibodies: A Practical Approach ISBN 0-19-963722-9, Jul. 13, 2020.
Smirnov et al, Cancer Res 65: 4993-7, 2005.
Smith and Waterman, 1981, Ads App. Math. 2,482.
So et at., Mol. Cells 7:178-186, 1997.
Stanislawski et al., Nat Immunol. 2:962-70, 2001.
Tuschl T. et al., "The siRNA User Guide", revised Oct. 11, 2002.
Roitt, I. (1991), Essential Immunology, 7th Edition, Blackwell Scientific Publications, Oxford).
Yuan et al. (Cytotherapy 8:498, 2006).
Reddehase et al., Nature vol. 337, pp. 651-653 (Feb. 1989).
Neefies et al., Nature Reviews, Immunology, vol. 11, pp. 823-836 (Dec. 2011).
Kessels et al., Nat Immunol. 2:957-61, 2001.
Kraeft et al, Clin Cancer Res 10: 3020-8, 2004.
Krieg et al., Nature 374:546-9, 1995.
Maloy et al., Proc Natl Acad Sci USA 98:3299-303,2001.
Neddleman and Wunsch, 1970, J. Mol. Biol. 48, 443.
Koslowski et al, 2006.
Koslowski et al, Cancer Research, American Association for Cancer Research, Baltimore, MD, vol. 67, No. 19, Oct. 1, 2007 (Oct. 1, 2007), pp. 9528-9534, XPQ02471063 ISSN: 0008-5472.
Merrifield, 1964.
Iacobuzio-Donahue et al. 2002.
Lu et al. (2004) Clinical Cancer Research vol. 10: 3291-3300.
Documentation of Affymetrix probe set "75948_AT", Feb. 13, 2019.
Arnon et al. Monoclonal Antibodies for Immunotargeting of Drugs in Cancer Therapy Resifeld et al. (eds.), pp. 243-256 (Alan R. Liss, Inc. 1985).
Babcook et al., Proc. Natl. Acad. Sci, USA, vol. 93, pp. 7843-7848, Jul. 1996; A novel strategy for generating monoclonal antibodies from single, isolated lymphocytes producing antibodies of defined strategy.
Order, S., "Analysis, Results, and Future Prospective of the Therapeutic Use of Radiolabeled Antibody in Cancer Therapy", in Monoclonal Antibodies for Cancer Detection and Therapy Baldwin et al. (eds.), pp. 303-316 (Academic Press 1985).
Berg, S.M., et al. (1977) J. Pharm. Sci. 66:12-19.
Berzolsky et al., "Antibody-Antigen Interactions" In Fundamental Immunology, Paul, W. E., Ed., Raven Press New York, NY (1984), Kuby, Janis Immunology, W. H. Freeman and Company New York, N Y (1992).
Bird et al. (1988) Science 242: 423-426.
Cunningham-Rundles C, Zhuo Z, Griffith B, Keenan J. (1992) Biological activities of polyethylene-glycol immunoglobulin conjugates. Resistance to enzymatic degradation. 1. Immunol. Methods, 152: 177-190.
Fischer, R., et al. (1999) Biol. Chem. 380: 825-839.
Casset et al. (Biochemical and Biophysical Research Communications, 2003, 307:198-205).
Hellstrom et al., "Antibodies for Drug Delivery" in Controlled Drug Delivery (2nd Ed.), Robinson et al. (eds.), pp. 623-653 (Marcel Dekker, Inc. 1987).
Holliger, P., et al. (1993) Proc. Natl. Acad. Sci. USA 90: 6444-6448.
Xu et al. "Diversity in the CDR3 Region of VH is Sufficient for Most Antibody Specificities", Immunity, vol. 13, No. 1, Jul. 2000.
Arabzadeh et al. "Role of the Cldn6 Cytoplasmic Tail Domain in Membrane Targeting and Epidermal Differentiation in Vivo", Molecular and Cellular Biology, vol. 26(15), Aug. 2006.
GenBank: NP_067018.1, printed Apr. 25, 2018.
U.S. Appl. No. 15/726,063, filed Oct. 5, 2017.
U.S. Appl. No. 13/201,702, filed Aug. 29, 2011.
Huston et al. (1988) Proc. Natl. Acad. Sci. USA 85: 5879-5883.
Jones, P. et al. (1986) Nature 321: 522-525.
Kohler and Milstein, Nature 256: 495 (1975).
Kozak, 1991, J. Biol Chem. 266: 19867-19870.
ISR & WO for PCT/EP2011/003312, mailed Oct. 5, 2011.
Arabzadeh et al., "Changes in the distribution pattern of Caludin tight junction proteins during the progression of mouse skin tumorigenesis.", BMC Cancer, vol. 7, Oct. 18, 2007, p. 196, XP021034484.
Landor M. (1995) Maternal-fetal transfer of immunoglobulins, Ann. Allergy Asthma Immunol. 74: 279-283.
Watz et al. (Nucleic Acids research, 1999 vol. 27, No. 6 1558-60.
Monteiro, R. C. et al. (1992) J. Immunol. 148: 1764).
Morris, Glenn E. Epitope Mapping Protocols (Methods in Molecular Biology) ISBN-089603-375-9 , 1996.
Morrison, S. (1985) Science 229: 1202.
Morton, H.C. et al. (1996) Critical Reviews in Immunology 16: 423-440).
Chen et al. (Journal of Molecular Biology, 1999, 293:865-881).
IPRP for PCT/EP2012/001721 mailed Nov. 19, 2013.
Pollock, et al. (1999) J. Immunol. Meth. 231: 147-157.
Queen, C. et aL (1989) Proc, NatL Acad. Sci. U. S. A. 86: 10029-10033.
Remington: The Science and Practice of Pharmacy, 19th Edition, Gennaro, Ed., Mack Publishing Co., Easton, PA, 1995.
Riechmann, L. et aL (1998) Nature 332: 323-327.
Rossi et al., Am. J. Clin. Pathol. 124: 295 (2005).
Cristofanilli et al, N Eng.J Med 351: 781-91, 2004.
Scatchard et al., Ann N.Y. Acad. ScL, 51:660 (1949).
Shields et al. (2002) JBC, 277: 26733.

(56) References Cited

OTHER PUBLICATIONS

European Search Report corresponding to European Patent Application Seriai No. 09014136.7 dated Mar. 23, 2010.
Extended European Search Report for 10006957.4-2406 dated Nov. 10, 2010.
Spieker-Polet et al. Proc. Natl. Acad. Sci. U.S.A. 92:9348 (1995).
Strejan et al. (1984) J. Neuroimmunol. 7:27.
Thorp et al., "The Preparation and Cytotoxic Properties of Antibody-Toxin Conjugates" Immunol. Rev., 62: 119-58 (1982).
Thorp, "Antibody Carriers of Cytotoxic Agents in Cancer Therapy: A Review" in Monoclonal Antibodies '84: Biological and Clinical Applications, Pinchera et al. (eds. ), pp. 475-506 (1985).
Verma, R., et al. (1998) J. Immunol. Meth. 216: 165-181.
Ward et al., (1989) Nature 341: 544-546.
Welschof and Kraus, Recombinant antibodes for cancer therapy ISBN-0-89603-918-8, 2003.
Westwood, et al. "Epitope Mapping: A Practical Approach" Practical Approach Series, 248, 2001.
Hall (1995) Science 268: 1432-1434.
Hewitt et al., "The claudin gene family: expression in normal and neoplastic tissdues." BMC Cancer, Biomed Central. vol. 6, No. 1, Jul. 12, 2006. XP021016181.
ISR for PCT/EP2012/001721 dated Jul. 25, 2012.
Benny K.C. Lo Antibody Engineering ISBN 1-58829-092-1, 2004.
IPRP for PCT/EP2010/006888 dated May 15, 2012.
ISR & WO for PCT/EP2010/006888, mailed Feb. 4, 2011.
Lamminmaki et al. (Journal of Biological Chemistry, 2001, 276:36687-36694.
Morita et al., "Endothelial claudin: Claudin-5/TMVCF constitutes tight junction strands in endothelial cells." The Journal of Cell Biology, vol. 147, No. 1, Oct. 4, 1999, pp. 185-194, XP002239048.

\* cited by examiner

Figure 4

| | | |
|---|---|---|
| NIH-OVCAR3 | NIH-OVCAR3 | NIH-OVCAR3 |
| Pancreas | Breast | Esophagus |
| Pancreas | Breast | Esophagus |
| Pancreas | Breast | Esophagus |
| Pancreas | Breast | Esophagus |
| Liver | Lymph node | Thyroid |
| Liver | Lymph node | Prostate |
| Liver | Lymph node | Prostate |
| Liver | Lymph node | Prostate |
| Liver | Lymph node | NIH-OVCAR3 |
| Gall bladder | Spleen | Breast |
| Gall bladder | Spleen | Breast |
| Gall bladder | Spleen | Breast |
| Duodenum | Kidney | Colon |
| Duodenum | Kidney | Colon |
| Duodenum | Kidney | Colon |
| Testis | Endometrium | Colon |
| Testis | Endometrium | Colon |
| Testis | Epididymis | Colon |
| Lung | | |
| Lung | | |

Figure 8A:
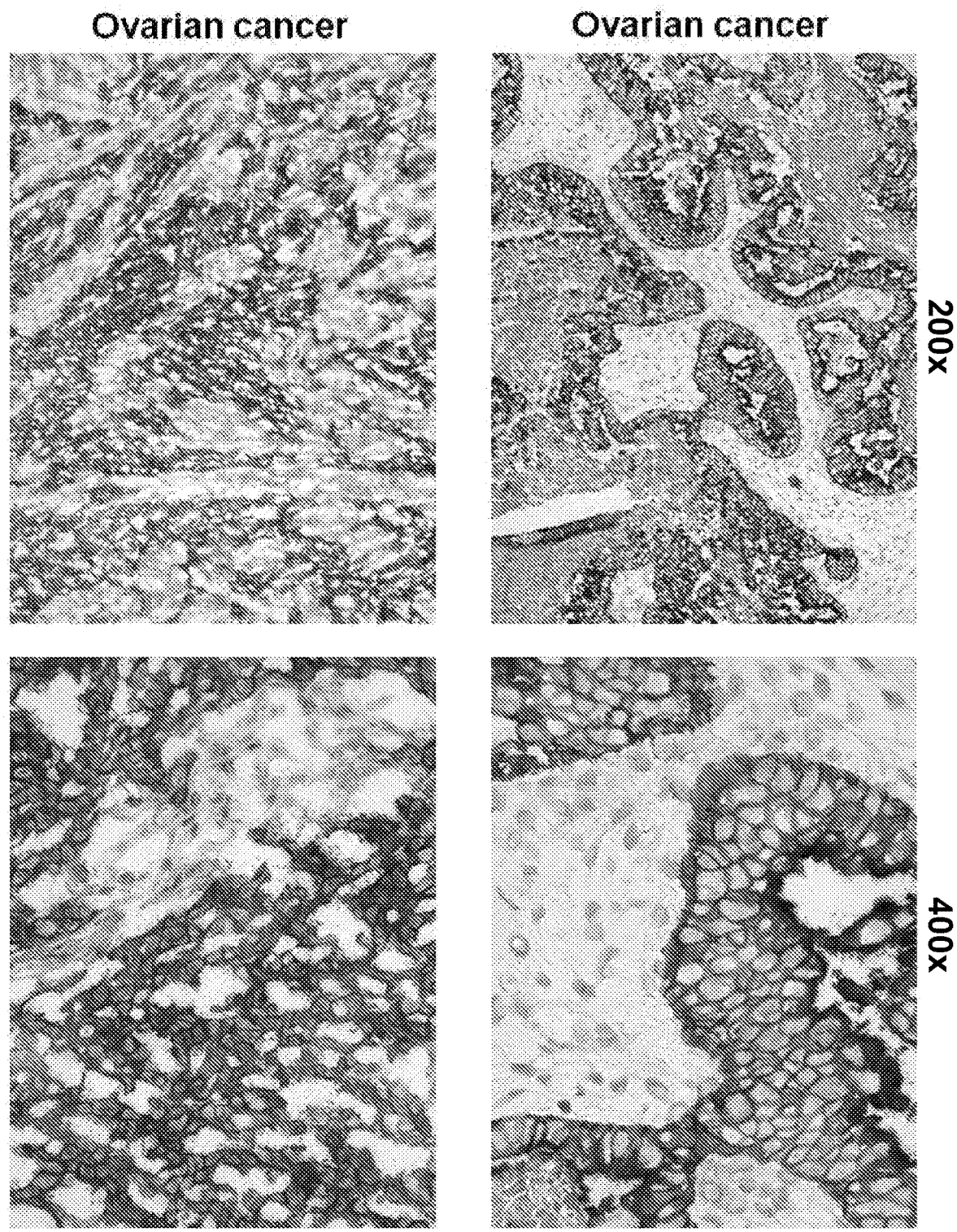
Figure 8C:
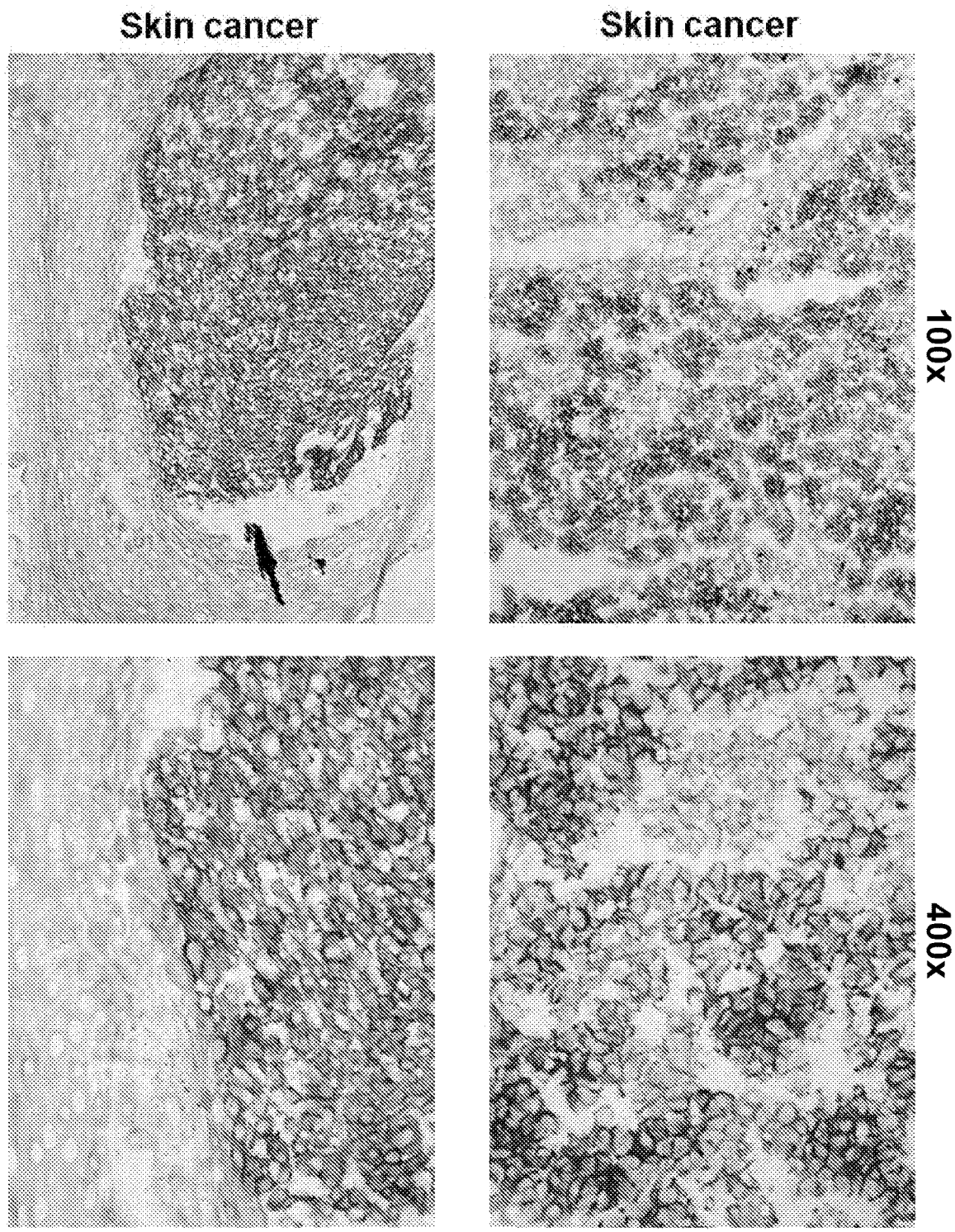
Figure 8E:
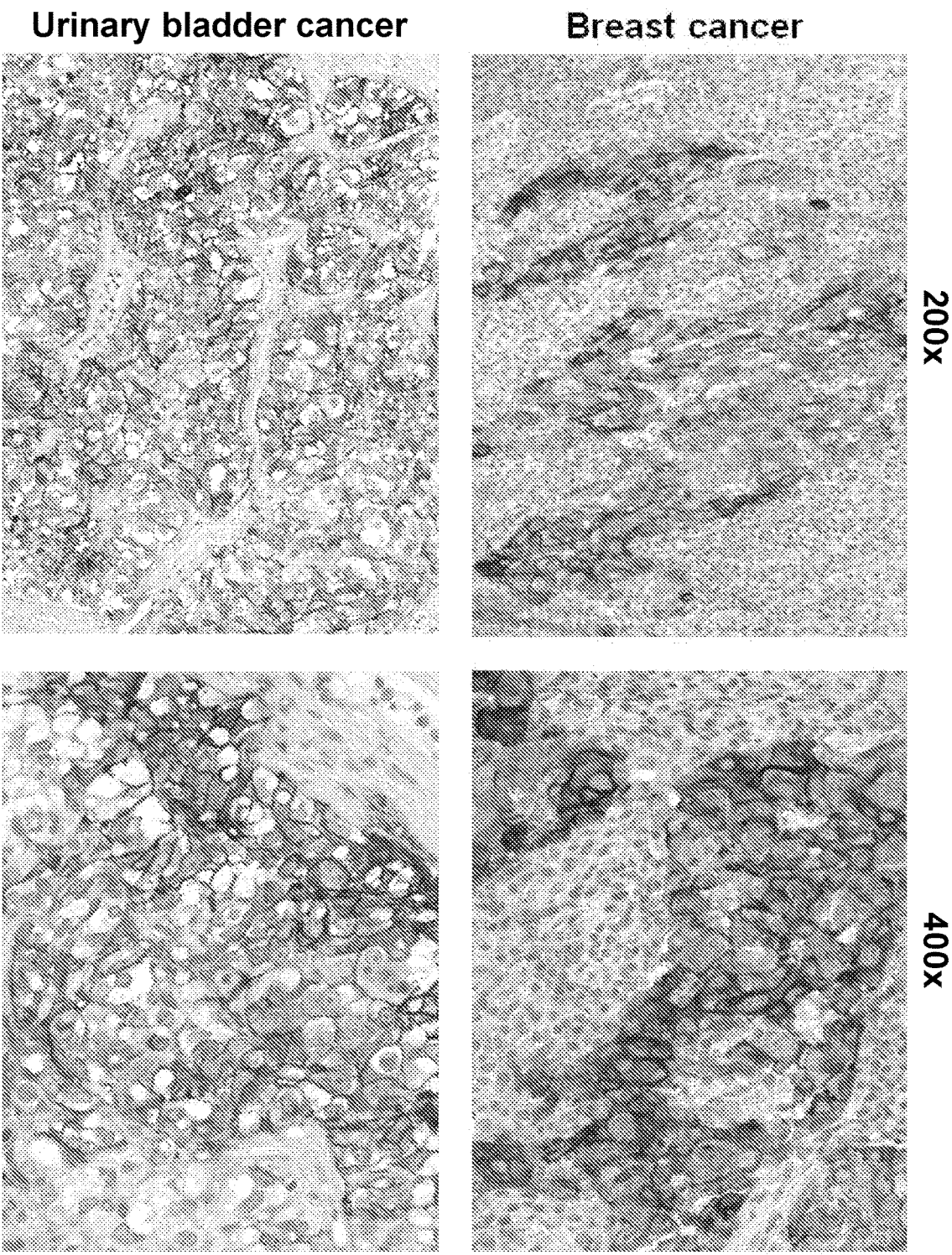

Figure 8b
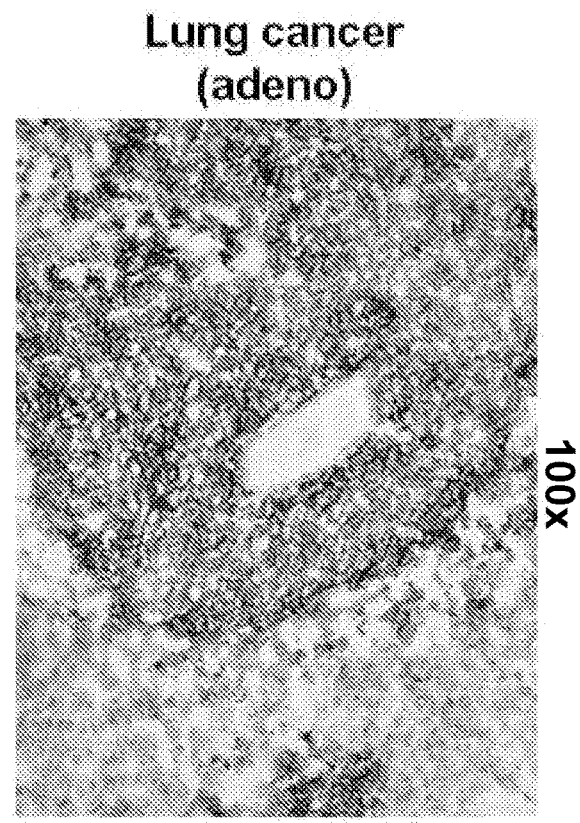
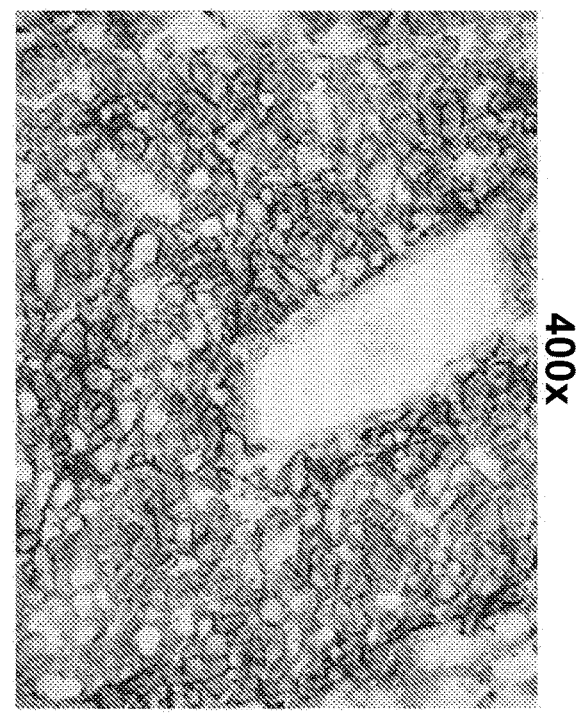

Figure 8d
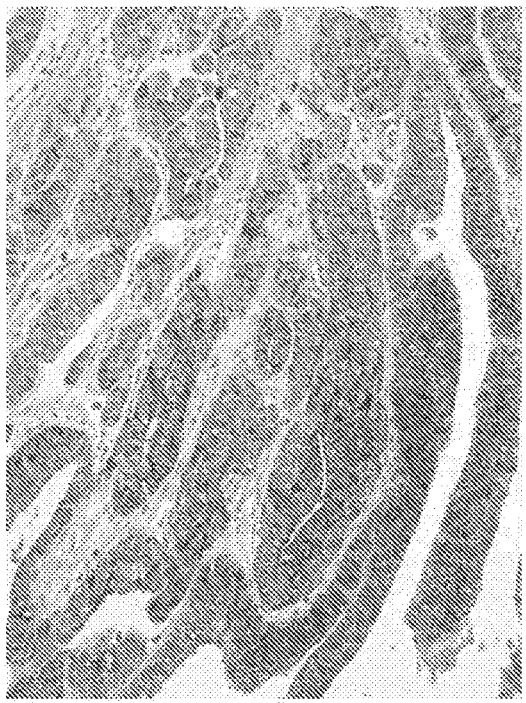
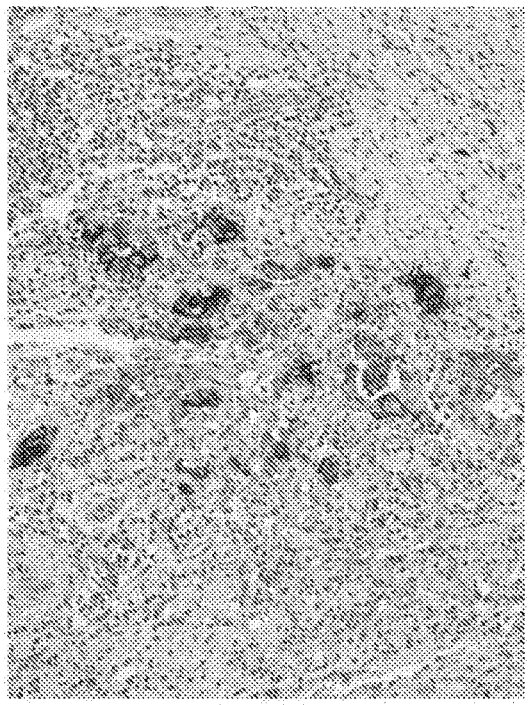
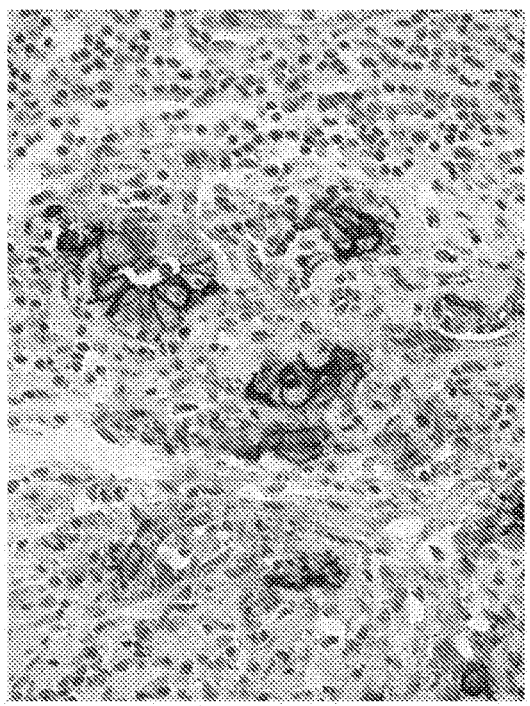

Figure 8f
| Cervical cancer | Testicular cancer (Seminoma) |
|---|---|
| 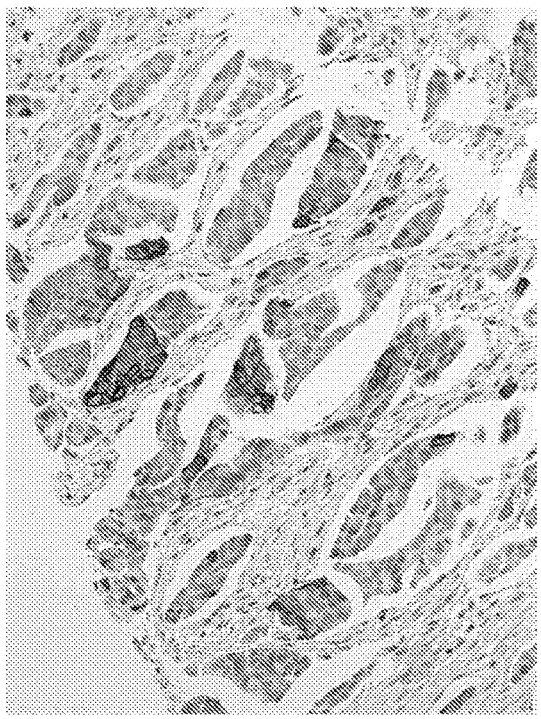 | 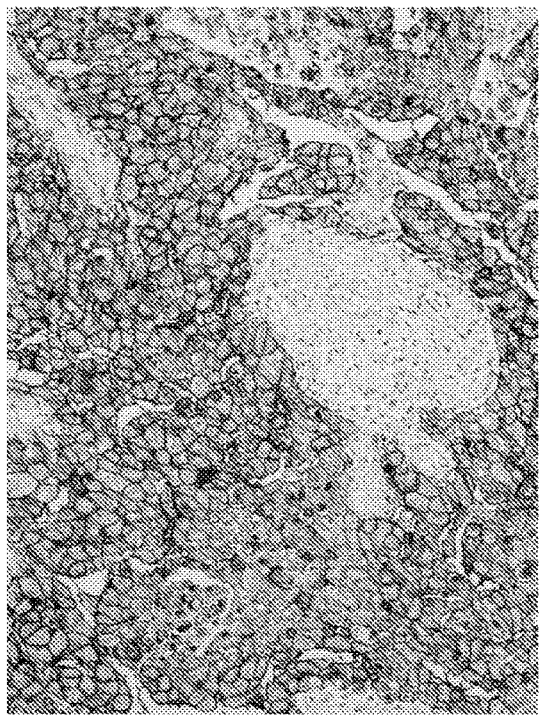 200x |
|  | 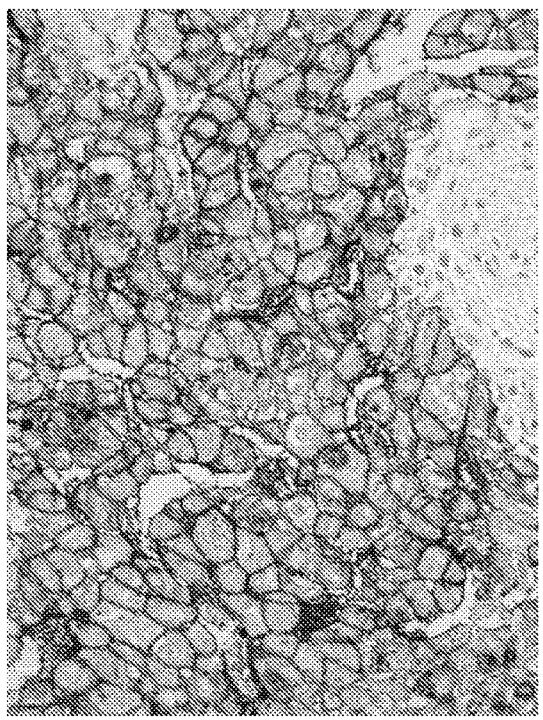 400x |

Figure 8g
Small bowel cancer  Uterine cancer
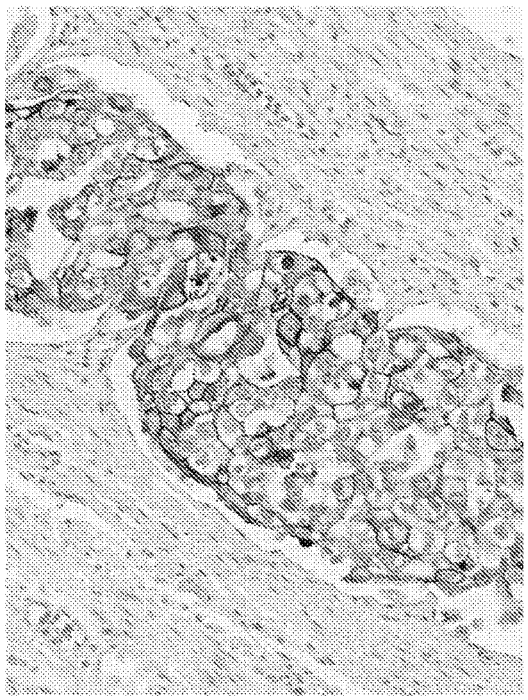 
200x
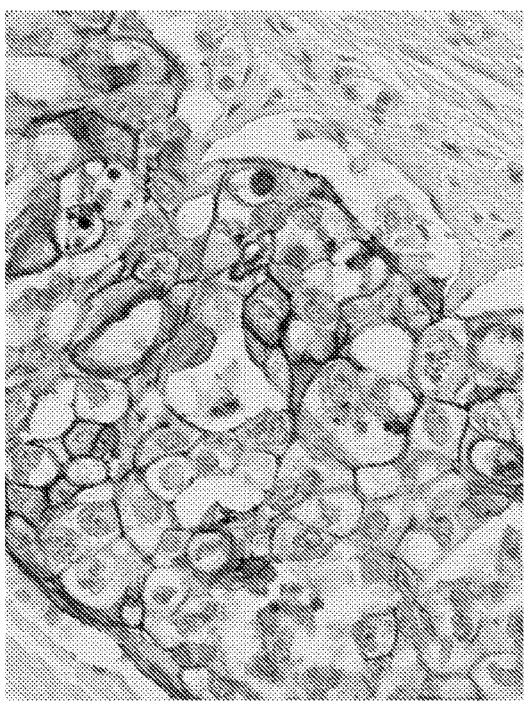 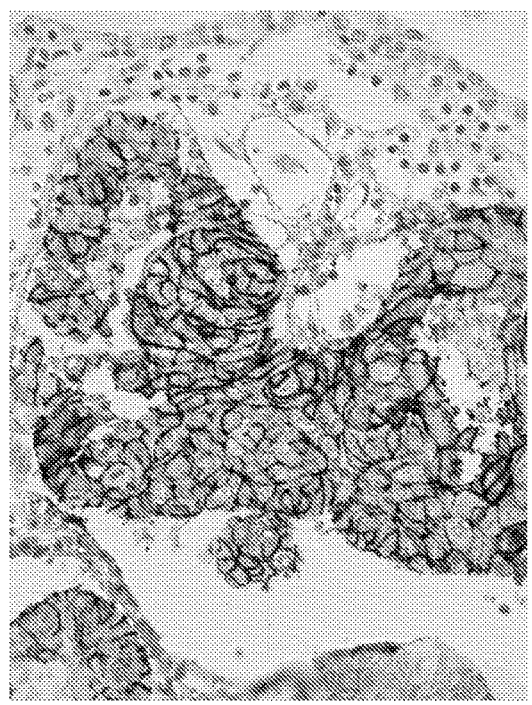
400x Figure 8h
Testicular cancer (Teratoma)     Testicular cancer (embryonic)
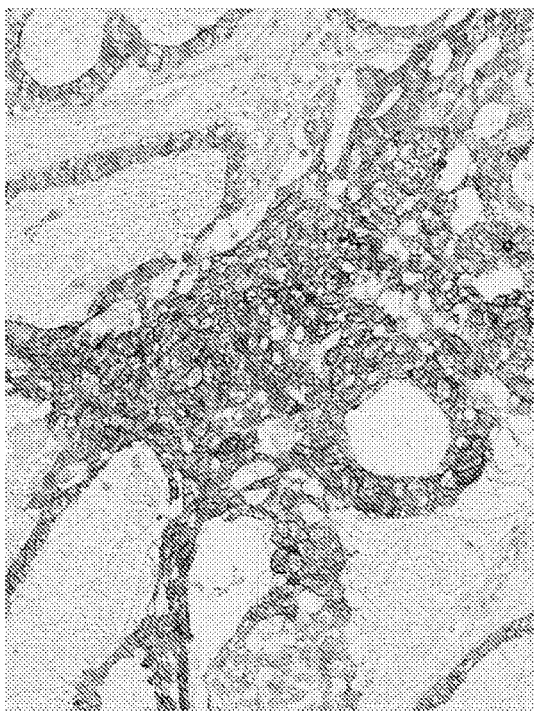 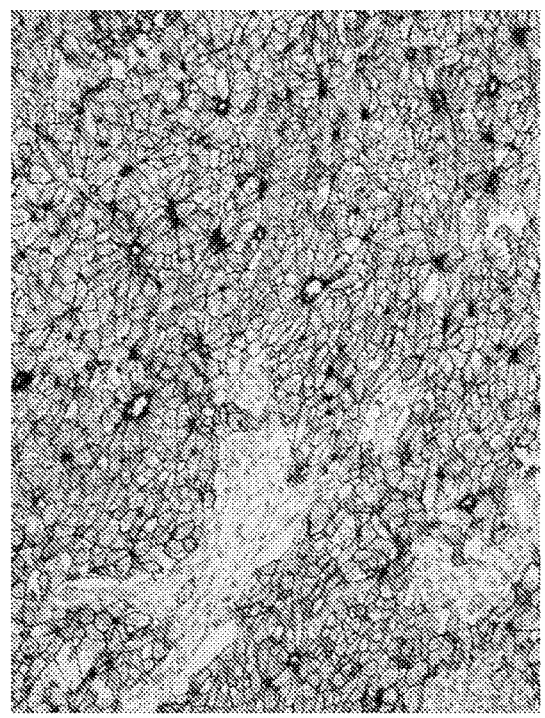
200x
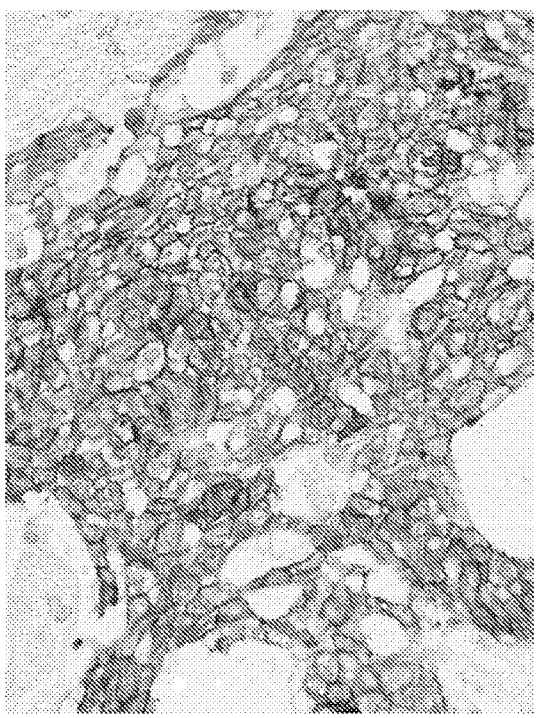 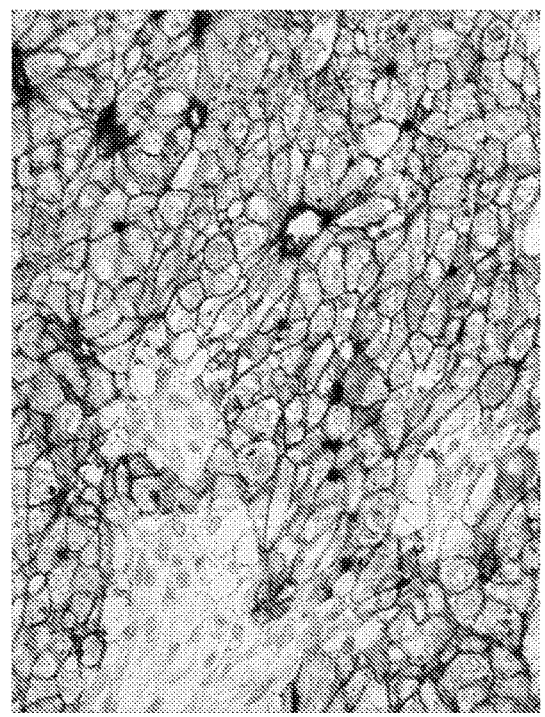
400x

METHODS AND COMPOSITIONS FOR DIAGNOSIS AND TREATMENT OF CANCER

This application is a continuation of U.S. application Ser. No. 15/726,063, filed on Oct. 5, 2017 as a divisional of U.S. application Ser. No. 13/201,702, now U.S. Pat. No. 9,809,815, filed on Aug. 29, 2011 as a National Stage Entry of PCT/EP10/01062, filed on Feb. 19, 2010, which claimed priority to U.S. Application No. 61/260,135, filed on Nov. 11, 2009, European Application No. 09014135.9, filed on Nov. 11, 2009, U.S. Application No. 61/231,843, filed on Aug. 6, 2009, European Application No. 09010164.3, filed on Aug. 6, 2009, U.S. Application No. 61/154,167, filed on Feb. 20, 2009, and European Application No. 09002452.2, filed on Feb. 20, 2009. The contents of each of the aforementioned applications are incorporated herein by reference in their entireties.

Cancer is a significant health problem throughout the world and is still among the leading causes of death.

Ovarian cancer is a cancerous growth arising from an ovary. Ovarian cancer is the fifth leading cause of death from cancer in women and the leading cause of death from gynecological cancer. A woman has a lifetime risk of ovarian cancer of around 1.5%, which makes it the second most common gynecologic malignancy.

The diagnosis of ovarian cancer can be suspected from an abnormal physical examination (including a pelvic examination), a blood test (for CA-125, more specifically) or from medical imaging studies. The diagnosis can be confirmed with a surgical procedure to inspect the abdominal cavity, take biopsies and look for cancer cells in the abdominal fluid. Treatment usually involves chemotherapy and surgery, and sometimes radiotherapy.

There is an increased risk of ovarian cancer in older women and in those who have a first or second degree relative with the disease. Hereditary forms of ovarian cancer can be caused by mutations in specific genes (most notably BRCA1 and BRCA2). Infertile women and those with a condition called endometriosis, those who have never been pregnant and those who use postmenopausal estrogen replacement therapy are at increased risk. Use of oral contraceptive pills is a protective factor. The risk is also lower in women who have had their uterine tubes blocked surgically (tubal ligation).

Ovarian cancer usually has a poor prognosis. It is disproportionately deadly because it lacks any clear early detection or screening test, meaning that most cases are not diagnosed until they have reached advanced stages. More than 60% of patients presenting with this cancer already have stage III or stage IV cancer, when it has already spread beyond the ovaries. Ovarian cancers shed cells into the naturally occurring fluid within the abdominal cavity. These cells can implant on other abdominal (peritoneal) structures, included the uterus, urinary bladder, bowel and the lining of the bowel wall (omentum). These cells can begin forming new tumor growths before cancer is even suspected.

The five-year survival rate for all stages of ovarian cancer is 45.5%. For cases where a diagnosis is made early in the disease, when the cancer is still confined to the primary site, the five-year survival rate is 92.7%.

The main categories of ovarian tumors are as follows: Epithelial tumors, which account for about 75% of all ovarian tumors, and 90-95% of ovarian malignancies; Sex cord-stromal tumors, which account for about 5-10% of all ovarian neoplasms; Germ cell tumors, which account for about 15-20% of all ovarian neoplasms; Metastatic tumors, accounting for about 5% of ovarian malignancies, and usually arising from breast, colon, endometrium, stomach and cervical cancers. Ovarian cancer most commonly forms in the lining of the ovary (resulting in epithelial ovarian cancer) or in the egg cells (resulting in a germ cell tumor).

Surface epithelial-stromal tumor, also known as ovarian epithelial carcinoma, is the most common type of ovarian cancer. Surface epithelial-stromal tumors are a class of ovarian neoplasms that may be benign or malignant. Neoplasms in this group are thought to be derived from the ovarian surface epithelium (modified peritoneum) or from ectopic endometrial or Fallopian tube (tubal) tissue. Surface epithelial-stromal tumors include serous tumor, endometrioid tumor and mucinous cystadenocarcinoma.

Lung cancer is a disease of uncontrolled cell growth in tissues of the lung. This growth may lead to metastasis, which is invasion of adjacent tissue and infiltration beyond the lungs. Lung cancer, the most common cause of cancer-related death in men and the second most common in women (after breast cancer), is responsible for 1.3 million deaths worldwide annually.

Lung tumors include epidermoid cancers and adenocarcinomas. The vast majority of lung cancers are carcinomas—malignancies that arise from epithelial cells.

Lung cancer may be characterized by five histopathological criteria. A distinction is drawn between squamous epithelial carcinoma, adenocarcinoma, large cell carcinoma, adenosquamous carcinoma and small cell lung carcinoma (SCLC). The first four are cited as non-SCLC (NSCLC) in literature.

Non-small cell lung carcinoma (NSCLC) is sometimes treated with surgery, while small cell lung carcinoma (SCLC) usually responds better to chemotherapy and radiation.

Lung cancer may be seen on chest x-ray and computed tomography (CT scan). The diagnosis is confirmed with a biopsy. This is usually performed via bronchoscopy or CT-guided biopsy. Treatment and prognosis depend upon the histological type of cancer, the stage (degree of spread), and the patient's performance status. Possible treatments include surgery, chemotherapy, and radiotherapy. With treatment, the five-year survival rate is 14%.

The immune system has the ability to recognize and destroy cells via two separate modalities: innate and adaptive immunity. The innate component consists of macrophages, natural killer (NK) cells, monocytes, and granulocytes. These cells identify molecular patterns involved in cellular transformation and release various cytokines and inflammatory mediators. The innate response lacks the memory capability for foreign antigens, a feature present in adaptive immune response. This latter component of immune system also features specificity for foreign antigens, imparted by presence of receptors on lymphocytes. Antigen presenting cells (APCs) also play a role in the adaptive response—they engulf foreign antigens and present them to the lymphocytes in the context of major histocompatibility complex. CD4+ T cells bear receptors that recognize antigens in the context of MHC class II molecules, which then enables them to release cytokines and further activate CD8+ lymphocytes (CTLs) or B cells. CTLs are part of cell-mediated immunity and are capable of eliminating cells presented in the context of MHC class I molecules, via apoptosis or perforin-mediated cell lysis. It is widely accepted that T-cell mediated immunity plays a vital role in the anti-tumor response.

B cells are involved in release of immunoglobulins and as such are part of the humoral immune system.

If properly aimed and enhanced, immune functions can be therapeutically exploited to control and even eradicate malignant lesions. Genetic and epigenetic changes involved in carcinogenesis generate antigens that are recognized by the immune system in analogous fashion to microbial antigens.

There is a need in the art for genetic markers and targets of tumors such as ovarian tumors and lung tumors, in particular ovarian adenocarcinomas and bronchiolar adenocarcinomas, and metastatic tumors derived therefrom, allowing the design of specific, reliable and sensitive diagnostic and therapeutic approaches of these diseases.

The invention relates to the therapy and diagnosis of tumors such as ovarian tumors and lung tumors, in particular ovarian adenocarcinomas and bronchiolar adenocarcinomas, and metastatic tumors derived therefrom. In particular, the invention relates to the identification of molecular structures that are present on tumors such as ovarian tumors and lung tumors and can serve as targets for diagnostic and therapeutic approaches of these diseases.

SUMMARY OF THE INVENTION

The present invention relates to the identification of nucleic acid and amino acid sequences that are characteristic of tumor tissues such as ovarian and lung tumor tissues, and which represent targets for therapy or diagnosis of tumor diseases in a subject.

These sequences encompass proteins identified to be in the plasma membrane of the cells, and accessible on the extra-cellular region, so that the sequences may be useful in the preparation of tumor vaccines, including prophylatic and therapeutic vaccines.

The nucleic acids identified according to the invention to be expressed in tumor cells comprise the nucleic acid sequence according to SEQ ID NO: 1 of the sequence listing or a variant of said nucleic acid sequence. Preferably, the nucleic acids identified according to the invention to be expressed in tumor cells encode a peptide comprising the amino acid sequence according to SEQ ID NO: 2 of the sequence listing or a variant of said amino acid sequence. These nucleic acids are also termed "tumor-associated nucleic acids" or simply "tumor nucleic acids" herein.

In another aspect, the invention relates to peptides encoded by the tumor nucleic acids identified according to the invention, also termed "tumor-associated antigens" or simply "tumor antigens" herein. Accordingly, the tumor antigens identified according to the invention comprise an amino acid sequence encoded by a nucleic acid which comprises the nucleic acid sequence according to SEQ ID NO: 1 of the sequence listing or a variant of said nucleic acid sequence. Preferably, the tumor antigens identified according to the invention comprise the amino acid sequence according to SEQ ID NO: 2 of the sequence listing or a variant of said amino acid sequence.

In one aspect, the invention provides peptides comprising amino acid sequences derived from the sequences of the tumor antigens identified according to the invention, also termed "tumor antigen peptides" herein. Preferably, the tumor antigen peptides of the invention are capable of stimulating a cellular response against cells characterized by presentation of a tumor antigen identified according to the invention with class I MHC and/or of eliciting antibodies that specifically bind to a tumor antigen identified according to the invention when used itself or attached to an immunogenic carrier. Preferred tumor antigen peptides may be presented, directly or following processing, with class I MHC molecules. Preferably, the tumor antigen peptides according to the invention are MHC class I and/or class II presented peptides or can be processed to produce MHC class I and/or class II presented peptides. Preferably, the tumor antigen peptides according to the invention comprise an amino acid sequence substantially corresponding to the amino acid sequence of a fragment of a tumor antigen identified according to the invention. Preferably, said fragment of a tumor antigen identified according to the invention is a MHC class I and/or class II presented peptide or is an immunogen that is capable of eliciting antibodies binding to said fragment. Preferably, a tumor antigen peptide according to the invention comprises an amino acid sequence substantially corresponding to the amino acid sequence of such fragment and is processed to produce such fragment, i.e. a MHC class I and/or class II presented peptide derived from a tumor antigen identified according to the invention or an immunogen derived from a tumor antigen identified according to the invention that is capable of eliciting antibodies binding to said fragment. Thus, a tumor antigen peptide according to the invention comprises an amino acid sequence substantially corresponding to the amino acid sequence of a fragment of a tumor antigen comprising an amino acid sequence encoded by a nucleic acid which comprises the nucleic acid sequence according to SEQ ID NO: 1 of the sequence listing or a variant of said nucleic acid sequence and preferably comprises an amino acid sequence substantially corresponding to the amino acid sequence of a fragment of a tumor antigen comprising the amino acid sequence according to SEQ ID NO: 2 of the sequence listing or a variant of said amino acid sequence. In one embodiment, a tumor antigen peptide according to the invention comprises an amino acid sequence selected from the group consisting of SEQ ID NOs: 3, 4 and 5 of the sequence listing or a fragment thereof, or a variant of said amino acid sequence or fragment.

The present invention generally embraces the treatment and/or diagnosis of tumor diseases by targeting tumor nucleic acids or tumor antigens. These methods provide for the selective detection of cells and/or eradication of cells that express such tumor nucleic acids and/or tumor antigens thereby minimizing adverse effects to normal cells not expressing such tumor nucleic acids and/or tumor antigens. Thus, preferred diseases for a therapy or diagnosis are those in which one or more of the tumor nucleic acids and/or tumor antigens identified according to the invention are expressed such as tumor diseases, in particular cancer diseases such as those described herein.

According to the invention, particularly suitable for targeting the tumor antigens identified according to the invention is a part of the tumor antigens which corresponds to the non-transmembrane portion, in particular the extracellular portion of the tumor antigens or is comprised thereof. In one embodiment, said part or portion comprises an amino acid sequence selected from the group consisting of SEQ ID NOs: 3, 4 and 5 of the sequence listing or a fragment thereof, or a variant of said amino acid sequence or fragment. Therefore, the entities used according to the invention which are capable of binding to the tumor antigens identified according to the present invention preferably are capable of binding to a part of the tumor antigens identified according to the invention which corresponds to the non-transmembrane portion, in particular the extracellular portion of the tumor antigens or is comprised thereof. In one embodiment, said part or portion comprises an amino acid sequence selected from the group consisting of SEQ ID NOs: 3, 4 and 5 of the sequence listing or a fragment thereof, or a variant of said amino acid sequence or fragment. Similarly, peptides and nucleic acids used according to the invention for inducing an immune response with specificity to the tumor antigens identified according to the present invention preferably induce specificity for a part of the tumor antigens identified according to the invention which corresponds to the non-transmembrane portion, in particular the extracellular portion of the tumor antigens or is comprised thereof. In one embodiment, said part or portion comprises an amino acid sequence selected from the group consisting of SEQ ID NOs: 3, 4 and 5 of the sequence listing or a fragment thereof, or a variant of said amino acid sequence or fragment. Preferably, said peptides comprise a sequence substantially corresponding to a part of the tumor antigens identified according to the invention which corresponds to the non-transmembrane portion, in particular the extracellular portion of the tumor antigens or is comprised thereof, and said nucleic acids encode such peptides. In one embodiment, said part or portion comprises an amino acid sequence selected from the group consisting of SEQ ID NOs: 3, 4 and 5 of the sequence listing or a fragment thereof, or a variant of said amino acid sequence or fragment.

One aspect of this invention relates to therapies for treatment of tumor diseases, in particular ovarian tumors and lung tumors, involving the administration of an inhibitor of expression and/or activity of a tumor antigen identified according to the invention.

In this aspect, the present invention relates to a pharmaceutical composition comprising an inhibitor of expression and/or activity of a tumor antigen identified according to the invention. In one embodiment, said inhibitor is specific for a tumor nucleic acid identified according to the invention. In another embodiment, said inhibitor is specific for a tumor antigen identified according to the invention. According to the invention the phrase "inhibit expression and/or activity" includes a complete or essentially complete inhibition of expression and/or activity and a reduction in expression and/or activity. Preferably, said inhibition of expression of a tumor antigen identified according to the invention may take place by inhibiting the production of or reducing the level of transcript, i.e. mRNA, coding for a tumor antigen identified according to the invention, e.g. by inhibiting transcription or inducing degradation of transcript, and/or by inhibiting the production of tumor antigen identified according to the invention, e.g. by inhibiting translation of transcript coding for a tumor antigen identified according to the invention. Preferably, said inhibition of expression and/or activity of a tumor antigen identified according to the present invention reduces tumor cell growth and/or induces tumor cell death and thus, has a tumor-inhibiting or tumor-destroying effect.

In a particular embodiment, the inhibitor of expression of a tumor antigen identified according to the invention is an inhibitory nucleic acid (e.g., anti-sense oligonucleotide, ribozyme, iRNA, siRNA or a DNA encoding the same) selectively hybridizing to and being specific for a tumor nucleic acid identified according to the invention, thereby inhibiting (e.g., reducing) transcription and/or translation thereof.

Inhibitory nucleic acids of this invention include oligonucleotides having sequences in the antisense orientation relative to the target nucleic acids. Suitable inhibitory oligonucleotides typically vary in length from five to several hundred nucleotides, more typically about 20-70 nucleotides in length or shorter, even more typically about 10-30 nucleotides in length. These inhibitory oligonucleotides may be administered as free (naked) nucleic acids or in protected forms, e.g., encapsulated in liposomes. The use of liposomal or other protected forms may be advantageous as it may enhance in vivo stability and thus facilitate delivery to target sites.

Also, the target tumor nucleic acid may be used to design ribozymes that target the cleavage of the corresponding mRNAs in tumor cells. Similarly, these ribozymes may be administered in free (naked) form or by the use of delivery systems that enhance stability and/or targeting, e.g., liposomes.

Also, the target tumor nucleic acid may be used to design siRNAs that can inhibit (e.g., reduce) expression of the tumor nucleic acid. The siRNAs may be administered in free (naked) form or by the use of delivery systems that enhance stability and/or targeting, e.g., liposomes. They may also be administered in the form of their precursors or encoding DNAs.

siRNA preferably comprises a sense RNA strand and an antisense RNA strand, wherein the sense and antisense RNA strands form an RNA duplex, and wherein the sense RNA strand comprises a nucleotide sequence substantially identical to a target sequence of about 19 to about 25 contiguous nucleotides in a tumor nucleic acid identified according to the invention, preferably mRNA coding for the target tumor antigen.

In a further embodiment, the inhibitor of activity of a tumor antigen identified according to the invention is an antibody that specifically binds to said tumor antigen. In one embodiment, said antibody specifically binds to a peptide comprising an amino acid sequence selected from the group consisting of SEQ ID NOs: 3, 4 and 5 of the sequence listing or a fragment thereof, or a variant of said amino acid sequence or fragment. Binding of the antibody to the tumor antigen can interfere with the function of the tumor antigen, e.g. by inhibiting binding activity or catalytic activity.

Also, the present invention in another aspect relates to therapies for treatment of tumor diseases involving the administration of a ligand of a target molecule, i.e. a tumor nucleic acid or tumor antigen identified according to the invention. In this respect, a nucleic acid may be administered that selectively hybridizes to the target nucleic acid or an antibody may be administered that specifically binds to a target antigen, attached to therapeutic effector moieties, e.g., radiolabels, cytotoxins, cytotoxic enzymes, and the like in order to selectively target and kill cells that express these targets, e.g. tumor cells. In one embodiment, said antibody specifically binds to a peptide comprising an amino acid sequence selected from the group consisting of SEQ ID NOs: 3, 4 and 5 of the sequence listing or a fragment thereof, or a variant of said amino acid sequence or fragment.

In this aspect, the present invention relates to a pharmaceutical composition, comprising a ligand of a tumor nucleic acid or tumor antigen identified according to the invention, said ligand being attached to one or more therapeutic effector moieties. Preferably, said ligand is specific for said tumor nucleic acid or tumor antigen. In one embodiment, said ligand of a tumor nucleic acid or tumor antigen reduces tumor cell growth and/or induces tumor cell death and thus, has a tumor-inhibiting or tumor-destroying effect.

According to a further aspect of the invention, the identification of tumor nucleic acids and tumor antigens makes it possible to develop specific immunotherapies based on attacking tumor cells bearing the identified antigens, thereby delaying or preventing the development of a tumor disease or eradicating tumor cells. Immunotherapy encompasses a variety of interventions and techniques with the common goal of eliciting tumor cell destructive immune responses. A variety of clinical approaches utilising these nucleic acids and antigens are possible as summarised below. Approaches to cancer immunotherapy can be divided into active and passive categories. Active immunotherapy may involve the direct immunization of patients with antigens or nucleic acids encoding such antigens in an attempt to boost immune responses against the tumor. Passive immunotherapy refers to the administration of immune reagents with the goal of directly mediating antitumor responses. The present invention contemplates both approaches.

In this aspect, the invention relates to a pharmaceutical composition which comprises one or more agents selected from the group consisting of (i) a peptide comprising the amino acid sequence of a tumor antigen identified according to the invention or of a tumor antigen peptide derived from said tumor antigen, or a derivative of said peptide, (ii) a nucleic acid which codes for a peptide comprising the amino acid sequence of a tumor antigen identified according to the invention or of a tumor antigen peptide derived from said tumor antigen, or a derivative of said nucleic acid, (iii) a host cell which codes for a peptide comprising the amino acid sequence of a tumor antigen identified according to the invention or of a tumor antigen peptide derived from said tumor antigen, (iv) a virus which codes for a peptide comprising the amino acid sequence of a tumor antigen identified according to the invention or of a tumor antigen peptide derived from said tumor antigen, (v) a cell presenting a peptide comprising the amino acid sequence of a tumor antigen peptide derived from a tumor antigen identified according to the invention, or a derivative of said peptide, (vi) an antibody or T cell receptor which binds to a peptide comprising the amino acid sequence of a tumor antigen identified according to the invention or of a tumor antigen peptide derived from said tumor antigen, (vii) an immunoreactive cell sensitized in vitro to recognize a peptide comprising the amino acid sequence of a tumor antigen identified according to the invention or of a tumor antigen peptide derived from said tumor antigen, and (viii) an effector cell (or stem cell) transduced with a nucleic acid encoding a T cell receptor that recognises a peptide comprising the amino acid sequence of a tumor antigen identified according to the invention or of a tumor antigen peptide derived from said tumor antigen.

In one embodiment, a peptide according to (i) is a tumor antigen specific MHC class I or class II presented peptide or can be processed to produce a tumor antigen specific MHC class I or class II presented peptide, preferably a tumor antigen specific MHC class I presented peptide. Preferably, said peptide has a sequence substantially corresponding to a fragment of a tumor antigen identified according to the invention which is presented by MHC class I or class II, preferably MHC class I or can be processed to produce a peptide fragment having such sequence. Preferably, said peptide is capable of stimulating a cellular response against a tumor characterized by presentation of a tumor antigen identified according to the invention with class I MHC and/or is capable of stimulating a humoral immune response against a tumor characterized by expression of a tumor antigen identified according to the invention. In one embodiment, said peptide comprises an amino acid sequence selected from the group consisting of SEQ ID NOs: 3, 4 and 5 of the sequence listing or a fragment thereof, or a variant of said amino acid sequence or fragment.

In one embodiment, a nucleic acid according to (ii) codes for a tumor antigen specific MHC class I or class II presented peptide or codes for a peptide which can be processed to produce a tumor antigen specific MHC class I or class II presented peptide, preferably a tumor antigen specific MHC class I presented peptide. Preferably, said peptide has a sequence substantially corresponding to a fragment of a tumor antigen identified according to the invention which is presented by MHC class I or class II, preferably MHC class I or can be processed to produce a peptide fragment having such sequence. Preferably, said peptide is capable of stimulating a cellular response against a tumor characterized by presentation of a tumor antigen identified according to the invention with class I MHC and/or is capable of stimulating a humoral immune response against a tumor characterized by expression of a tumor antigen identified according to the invention. In one embodiment, said peptide comprises an amino acid sequence selected from the group consisting of SEQ ID NOs: 3, 4 and 5 of the sequence listing or a fragment thereof, or a variant of said amino acid sequence or fragment. Such nucleic acid may be present in a plasmid or an expression vector and may be functionally linked to a promoter.

In one embodiment, a host cell according to (iii) codes for a tumor antigen specific MHC class I or class II presented peptide or codes for a peptide which can be processed to produce a tumor antigen specific MHC class I or class II presented peptide, preferably a tumor antigen specific MHC class I presented peptide. Preferably, said peptide has a sequence substantially corresponding to a fragment of a tumor antigen identified according to the invention which is presented by MHC class I or class II, preferably MHC class I or can be processed to produce a peptide fragment having such sequence. Preferably, said peptide is capable of stimulating a cellular response against a tumor characterized by presentation of a tumor antigen identified according to the invention with class I MHC and/or is capable of stimulating a humoral immune response against a tumor characterized by expression of a tumor antigen identified according to the invention. In one embodiment, said peptide comprises an amino acid sequence selected from the group consisting of SEQ ID NOs: 3, 4 and 5 of the sequence listing or a fragment thereof, or a variant of said amino acid sequence or fragment. The host cell may be a recombinant cell and may secrete the encoded peptide or a procession product thereof, may express it on the surface and preferably may additionally express an MHC molecule which binds to said peptide or a procession product thereof and preferably presents said peptide or a procession product thereof on the cell surface. In one embodiment, the host cell expresses the MHC molecule endogenously. In a further embodiment, the host cell expresses the MHC molecule and/or the peptide or the procession product thereof in a recombinant manner. The host cell is preferably nonproliferative. In a preferred embodiment, the host cell is an antigen-presenting cell, in particular a dendritic cell, a monocyte or a macrophage.

In one embodiment, a virus according to (iv) codes for a tumor antigen specific MHC class I or class II presented peptide or codes for a peptide which can be processed to produce a tumor antigen specific MHC class I or class II presented peptide, preferably a tumor antigen specific MHC class I presented peptide. Preferably, said peptide has a sequence substantially corresponding to a fragment of a tumor antigen identified according to the invention which is presented by MHC class I or class II, preferably MHC class I or can be processed to produce a peptide fragment having such sequence. Preferably, said peptide is capable of stimulating a cellular response against a tumor characterized by presentation of a tumor antigen identified according to the invention with class I MHC and/or is capable of stimulating a humoral immune response against a tumor characterized by expression of a tumor antigen identified according to the invention. In one embodiment, said peptide comprises an amino acid sequence selected from the group consisting of SEQ ID NOs: 3, 4 and 5 of the sequence listing or a fragment thereof, or a variant of said amino acid sequence or fragment.

In one embodiment, a cell according to (v) endogenously expresses an MHC molecule. In a further embodiment, the cell recombinantly expresses an MHC molecule and/or a peptide comprising the amino acid sequence of a tumor antigen peptide derived from a tumor antigen identified according to the invention. Preferably, the cell presents the peptide comprising the amino acid sequence of a tumor antigen peptide derived from a tumor antigen identified according to the invention, or a derivative of said peptide by MHC molecules on its surface. Preferably, the presented peptide is a peptide having a sequence substantially corresponding to a fragment of a tumor antigen identified according to the invention which is presented by MHC class I or class II, preferably MHC class I. The cell is preferably nonproliferative. In a preferred embodiment, the cell is an antigen-presenting cell such as a dendritic cell, a monocyte or a macrophage. Thus, in a preferred embodiment, the cell according to (v) is an antigen presenting cell that comprises a tumor antigen peptide as described herein presented with class I MHC.

In one embodiment, an antibody according to (vi) is a monoclonal antibody. In further embodiments, the antibody is a chimeric, human or humanized antibody, or is a fragment of an antibody or a synthetic antibody. The antibody may be coupled to a therapeutic effector moiety or a detectable label. Preferably, the antibody or T cell receptor according to (vi) binds to a sequence in the peptide substantially corresponding to a fragment of a tumor antigen identified according to the invention. In one embodiment, said antibody or T cell receptor binds to a peptide comprises an amino acid sequence selected from the group consisting of SEQ ID NOs: 3, 4 and 5 of the sequence listing or a fragment thereof, or a variant of said amino acid sequence or fragment.

Preferably, a cell according to (vii) binds to a sequence in the peptide substantially corresponding to a fragment of a tumor antigen identified according to the invention which fragment is preferably presented by MHC class I or class II, preferably MHC class I. In one embodiment, a cell according to (vii) is obtainable by a method comprising the steps of (a) providing a sample containing immunoreactive cells, either obtained from a patient or from another individual of the same species, in particular a healthy individual, or an individual of a different species, (b) contacting said sample with cells presenting a peptide comprising an amino acid sequence substantially corresponding to a fragment of a tumor antigen identified according to the invention, or a derivative of said peptide, under conditions which favor production of CTLs against said peptide, and (c) introducing the CTLs into the patient in an amount suitable for lysing cells expressing the tumor antigen and preferably presenting it with class I MHC such as tumor cells.

In one embodiment, the method includes cloning of the T cell receptor of CTLs obtained and transferring the nucleic acid coding for the T cell receptor to effector cells such as CTLs or immature CTLs, either obtained from said patient or from another individual of the same species, in particular a healthy individual, or an individual of a different species, which effector cells thus receive the desired specificity and may be introduced into the patient. Effector cells according to (viii) can be produced in this way.

Vaccination using agents as described above may provide MHC class II-presented epitopes that are capable of eliciting a CD4+ helper T-cell response and/or a CD8+ T-cell response against tumor antigens identified according to the invention, in particular if expressed in cells such as tumor cells. Alternatively or additionally, vaccination using agents as described above may provide MHC class I-presented epitopes that are capable of eliciting a CD8+ T-cell response against tumor antigens identified according to the invention, in particular if expressed in cells such as tumor cells. Furthermore, vaccination using agents as described above may elicit antibodies specific for a tumor antigen identified according to the invention.

In one embodiment, the pharmaceutical composition of the present invention is a therapeutic or prophylactic anti-tumor vaccine preferably further comprising an immunomodulatory agent, or a nucleic acid encoding the same. In one embodiment, the immunomodulatory agent is an agonist of a positive costimulatory molecule, e.g., an Ig-fusion protein capable of effecting costimulation of a CTL. In another embodiment, the costimulatory agent is an antagonist of a negative costimulatory molecule, e.g., an antibody capable of reducing inhibition of CTL costimulation. In a preferred embodiment, the immunomodulatory agent is an anti-CTLA4 antibody.

A pharmaceutical composition of the invention may comprise a pharmaceutically acceptable carrier and may optionally comprise one or more adjuvants, stabilizers etc.

Another aspect of the invention involves the use of the agents and compositions described herein for a prophylactic and/or therapeutic treatment of tumor diseases.

In one aspect, the invention provides therapeutic and prophylactic methods of treating a patient having a tumor disease or being at risk of developing a tumor disease. In one aspect, the invention provides methods for inhibiting tumor growth. In one aspect, the invention provides methods for inducing tumor cell death.

Preferably, the tumor disease is a cancer disease, preferably selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, and uterine cancer, and the metastatic forms thereof. In one embodiment, the cancer disease is selected from the group consisting of ovarian cancer, lung cancer, metastatic ovarian cancer and metastatic lung cancer. Preferably, the ovarian cancer is a carcinoma or an adenocarcinoma. Preferably, the lung cancer is a carcinoma or an adenocarcinoma, and preferably is bronchiolar cancer such as a bronchiolar carcinoma or bronchiolar adenocarcinoma. In one embodiment, the tumor cell is a cell of such a cancer.

Preferably, the agents and compositions described herein are administered in a way such that the therapeutically active substance is not delivered or not substantially delivered to a tissue or organ wherein the cells when the tissue or organ is free of tumors substantially express a tumor antigen identified according to the invention and/or a tumor nucleic acid identified according to the invention such as placenta tissue. To this end, the agents and compositions described herein can be administered locally. Preferably, the agents and compositions are delivered to the ovary and/or lungs.

According to various embodiments, the methods of the invention comprise the administration of an inhibitor of expression and/or activity of a tumor antigen identified according to the invention, of a ligand of a tumor nucleic acid or of a tumor antigen identified according to the invention and/or of one or more immunotherapeutic agents as described herein. In one embodiment, the methods involve administering a pharmaceutical composition as described herein to a patient and preferably vaccinating a patient with an anti-tumor vaccine described herein. Any of the wide variety of vaccination methods known in the art may be used according to the present invention. Anti-tumor vaccines of the invention are preferably capable of inducing or promoting CTL activity against a tumor characterized by presentation of a tumor antigen identified according to the invention with class I MHC. These may be used in combination with adjuvants, which facilitate stimulation of the immune system by acting on T cells directly or through APCs. Adjuvants include immunomodulatory substances having a positive immunomodulatory effect, as described herein.

In various embodiment, the methods of the invention involve the stimulation of an anti-tumor CTL response against tumor cells expressing a tumor antigen identified according to the invention and preferably presenting a tumor antigen identified according to the invention with class I MHC, the inhibition of the growth of tumor cells expressing a tumor antigen identified according to the invention and preferably presenting a tumor antigen identified according to the invention with class I MHC, and/or the induction of the death of cells expressing a tumor antigen identified according to the invention and preferably presenting a tumor antigen identified according to the invention with class I MHC.

In one aspect, the invention provides an inhibitor of expression and/or activity of a tumor antigen identified according to the invention, a ligand of a tumor nucleic acid or of a tumor antigen identified according to the invention and/or one or more immunotherapeutic agents as described herein for use in the methods of treatment described herein. In one embodiment, the invention provides a pharmaceutical composition as described herein for use in the methods of treatment described herein.

The treatments based on targeting tumor nucleic acids or tumor antigens such as the immunotherapies described herein can be combined with surgical resection and/or radiation and/or traditional chemotherapy.

Another object of the invention is to provide methods for diagnosis, detection or monitoring, i.e. determining the regression, progression, course and/or onset, of a tumor disease. Preferably said methods involve the use of ligands such as monoclonal antibodies and nucleic acid probes which specifically bind to a target molecule. Suitable target molecules are (i) a tumor nucleic acid identified according to the invention, (ii) a tumor antigen identified according to the invention or a tumor antigen peptide derived therefrom, (iii) an antibody against a tumor antigen identified according to the invention or a tumor antigen peptide derived therefrom, (iv) a T cell which recognizes a tumor antigen identified according to the invention or a tumor antigen peptide derived therefrom and/or (v) a cell which presents a tumor antigen peptide derived from a tumor antigen identified according to the invention with class I or class II MHC, preferably class I MHC. Such methods may be used to detect whether a subject has or is at (increased) risk of developing a tumor disease, or, for instance, whether a treatment regimen is efficient.

Accordingly, the present invention relates to methods for diagnosis, detection or monitoring of a tumor disease comprising the detection of and/or determination of the quantity of one or more parameters selected from the group consisting of (i) a nucleic acid which comprises the nucleic acid sequence of a tumor nucleic acid identified according to the invention/a nucleic acid which codes for a peptide comprising the amino acid sequence of a tumor antigen identified according to the invention, (ii) a peptide comprising the amino acid sequence of a tumor antigen identified according to the invention or of a tumor antigen peptide derived from said tumor antigen, (iii) an antibody which binds to a peptide comprising the amino acid sequence of a tumor antigen identified according to the invention or of a tumor antigen peptide derived from said tumor antigen, (iv) a T cell that recognises a peptide comprising the amino acid sequence of a tumor antigen identified according to the invention or of a tumor antigen peptide derived from said tumor antigen and/or (v) a cell which presents a peptide comprising the amino acid sequence of a tumor antigen peptide derived from a tumor antigen identified according to the invention with class I or class II MHC, preferably class I MHC, in a biological sample isolated from a patient, preferably from a patient having a tumor disease, being suspected of having or falling ill with a tumor disease or having a potential for a tumor disease.

In one embodiment, a nucleic acid according to (i) codes for a peptide which is processed to produce a tumor antigen specific MHC class I or class II presented peptide, preferably, a tumor antigen specific MHC class I presented peptide.

In one embodiment, a peptide according to (ii) is a tumor antigen specific MHC class I or class II presented peptide or can be processed to produce a tumor antigen specific MHC class I or class II presented peptide, preferably, a tumor antigen specific MHC class I presented peptide.

Preferably, a T cell according to (iv) recognizes a sequence in the peptide substantially corresponding to a fragment of a tumor antigen identified according to the invention which is presented by MHC class I or class II, preferably MHC class I.

In one embodiment, a cell according to (v) presents the peptide by MHC class I or class II, preferably MHC class I on its surface. The cell is preferably nonproliferative. In a preferred embodiment, the cell is an antigen-presenting cell such as a dendritic cell, a monocyte or a macrophage. Thus, in a preferred embodiment, the cell according to (v) is an antigen presenting cell that comprises a tumor antigen peptide as described herein presented with class I MHC. In another embodiment, the cell is a tumor cell.

In one embodiment, the nucleic acid according to (i) or the peptide according to (ii) is detected or its quantity determined in situ in a cell, preferably a tumor cell. In one embodiment, the peptide according to (ii) is detected or its quantity determined in situ on the surface of a cell, either incorporated in the plasma membrane or in a complex with MHC class I or class II, preferably MHC class I.

Preferably, the tumor disease which is to be diagnosed, detected or monitored using the method of the invention is a cancer disease, preferably selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, and uterine cancer, and the metastatic forms thereof.

In one embodiment of the method for diagnosis, detection or monitoring of a tumor disease according to the invention, a biological sample and/or a control/reference sample is from a tissue or organ corresponding to the tissue or organ which is to be diagnosed, detected or monitored with respect to affection by a tumor disease; e.g. the tumor disease which is to be diagnosed, detected or monitored is ovarian cancer and the biological sample and/or control/reference sample is ovarian tissue. Such tissues and organs are described herein, for example, in connection with different tumor diseases and cancers.

In one embodiment of the methods for diagnosis, detection or monitoring of a tumor disease the biological sample is from a tissue or organ wherein the cells when the tissue or organ is free of tumors do not substantially express a tumor antigen identified according to the invention and/or a tumor nucleic acid identified according to the invention. Preferably said tissue is a tissue other than placenta tissue. Preferably, said tissue is tissue of ovary, lung, breast, duodenum, skin, colon, liver, lymph node, stomach, spleen, kidney, esophagus, pancreas, endometrium, brain, gallbladder, urinary bladder, ileum, adrenal gland, rectum and skeletal muscle, preferably tissue of ovary or tissue of lung.

According to the invention a tumor antigen and/or a tumor nucleic acid is not substantially expressed if the level of expression is lower compared to expression in placenta cells or placenta tissue and/or is lower compared to expression in ovarian tumor cells and/or lung tumor cells or ovarian tumor tissue and/or lung tumor tissue. Preferably, the level of expression is less than 10%, preferably less than 5%, 3%, 2%, 1%, 0.5%, 0.1% or 0.05% or even lower compared to the above cells or tissues. Preferably, a tumor antigen and/or a nucleic acid is not substantially expressed if the level of expression is below the detection limit.

The methods for diagnosis, detection or monitoring allow quantitative and/or qualitative evaluations, e.g., absolute and/or relative measure of target molecules e.g. expression levels of a tumor nucleic acid or a tumor antigen.

Means for accomplishing said detection and/or determination of the quantity are described herein and will be apparent to the skilled person.

Preferably, the detection and/or determination of the quantity in the methods of the invention comprises (i) contacting a biological sample with an agent which binds specifically to the nucleic acid, the peptide, the antibody, the T cell or the cell which is to be detected and/or the amount of which is to be determined, and (ii) detecting the formation of and/or determining the quantity of a complex between the agent and the nucleic acid, the peptide, the antibody, the T cell or the cell which is to be detected or the amount of which is to be determined.

Typically, the level of a target molecule in a biological sample is compared to a reference level, wherein a deviation from said reference level is indicative of the presence and/or stage of a tumor disease in a subject. The reference level may be a level as determined in a control sample (e.g., from a healthy tissue or subject) or a median level from healthy subjects. A "deviation" from said reference level designates any significant change, such as an increase or decrease by at least 10%, 20%, or 30%, preferably by at least 40% or 50%, or even more. Preferably, the presence of the nucleic acid, the peptide, the antibody, the T cell and/or the cell in said biological sample or a quantity of the nucleic acid, the peptide, the antibody, the T cell and/or the cell in the biological sample which is increased compared to a reference level indicates the presence of a tumor disease.

Typically, the detection and/or determination of the quantity in the methods of the invention involves the use of labeled ligands which specifically bind to a target molecule, e.g. a labeled nucleic acid probe that hybridizes to a target nucleic acid and/or a labeled antibody or fragment/derivative thereof that specifically binds to a target peptide.

According to the invention, detection of a nucleic acid or determining the quantity of a nucleic acid may be carried out using known nucleic acid detection methods such as methods involving hybridization or nucleic acid amplification techniques. In one embodiment, mRNA transcripts are detected or the quantity thereof is determined using RT-PCR or Northern blot analysis.

Such nucleic acid detection methods may involve the use of oligonucleotides hybridizing to the target nucleic acids. Suitable oligonucleotides typically vary in length from five to several hundred nucleotides, more typically about 20-70 nucleotides in length or shorter, even more typically about 10-30 nucleotides in length.

According to the invention, detection of a peptide or determining the quantity of a peptide may be carried out in a number of ways, including but not limited to immunodetection using an antibody binding specifically to said peptide. Preferably, the antibody binds to a sequence substantially corresponding to a fragment of a tumor antigen identified according to the invention. In one embodiment, said sequence comprises an amino acid sequence selected from the group consisting of SEQ ID NOs: 3, 4 and 5 of the sequence listing or a fragment thereof, or a variant of said amino acid sequence or fragment.

Methods for using antibodies to detect peptides are well known and include ELISA, competitive binding assays, and the like. In general, such assays use an antibody or antibody fragment that specifically binds the target peptide directly or indirectly bound to a label that provides for detection, e.g. indicator enzymes, radiolabels, fluorophores, or paramagnetic particles.

According to the invention, detection of an antibody or determining the quantity of an antibody may be carried out using a peptide binding specifically to said antibody.

T cells may be isolated from patient peripheral blood, lymph nodes, tissue samples such as derived from biopsy and resection, or other source. Reactivity assays may be performed on primary T cells or other appropriate derivatives. For example, T cells may be fused to generate hybridomas. Assays for measuring T cell responsiveness are known in the art, and include proliferation assays and cytokine release assays.

In one embodiment, the T cell that recognises a peptide comprising the amino acid sequence of a tumor antigen identified according to the invention or of a tumor antigen peptide derived from said tumor antigen is a tumor antigen-responsive CTL.

A CTL may be detected and its quantity determined in a number of ways, including but not limited to the following preferred embodiments. In one embodiment, CTLs are directly stained using an appropriate fluorescent tumor antigen peptide/MHC tetramer. In another embodiment, the "TRAP" assay ("T-cell recognition of APCs by protein transfer") is used (see, for example, Beadling et al. Nature Medicine 12:1208 (2006)). In another embodiment, detection of T cells in blood samples is performed using methods outlined by Yuan et al. (Cytotherapy 8:498, 2006). Assays and indices for detecting reactive T cells are known, and include but are not limited to the use of IFN-gamma ELISPOT and IFN-gamma intracellular cytokine staining.

Other various methods are known in the art for determining whether a T cell clone will respond to a particular antigenic peptide. Typically the peptide is added to a suspension of the T cells for a period of from one to three days. The response of the T cells may be measured by proliferation, e.g., uptake of labeled thymidine, or by release of cytokines, e.g., IL-2. Various assays are available for detecting the presence of released cytokines.

T cell cytotoxic assays can be used to detect cytotoxic T cells having specificity for tumor antigens. In one embodiment, cytotoxic T cells are tested for their ability to kill target cells presenting tumor antigen peptide with MHC class I molecules. Target cells presenting tumor antigen peptide may be labeled and added to a suspension of T cells from a patient sample. The cytotoxicity may be measured by quantitating the release of label from lysed cells. Controls for spontaneous and total release may be included in the assay.

A cell presenting a peptide may be detected and its quantity determined by testing for its ability to induce a cellular response, e.g. to activate T cells, or measuring lysis of cells by CTLs having specificity for such cell.

The presence of said nucleic acid, said peptide, said antibody, said T cell and/or said cell which is to be detected and/or the quantity of which is to be determined and/or a quantity of said nucleic acid, said peptide, said antibody, said T cell and/or said cell which is increased compared to a reference level, e.g. compared to a patient without a tumor disease, may indicate the presence of or risk for (i.e. a potential for a development of) a tumor disease in said patient. In one embodiment, the presence of said nucleic acid, said peptide, said antibody, said T cell and/or said cell which is to be detected and/or the quantity of which is to be determined and/or a quantity of said nucleic acid, said peptide, said antibody, said T cell and/or said cell which is increased compared to a reference level, e.g. compared to a patient without a tumor disease, may indicate the presence of or risk for metastatic cancer such as metastatic ovarian cancer or metastatic lung cancer.

In one embodiment, the biological sample is from a tissue or organ wherein the cells when the tissue or organ is free of tumors do not substantially express a tumor antigen identified according to the invention and/or a tumor nucleic acid identified according to the invention. The indication of the presence of or risk for a tumor disease in a patient by the methods of the invention may indicate that the tumor disease is in said tissue or organ or that said tissue or organ is at risk for said tumor disease.

In one embodiment, the biological sample is from a tissue or organ wherein the cells when the tissue or organ is free of tumors do not substantially express a tumor antigen identified according to the invention and/or a tumor nucleic acid identified according to the invention and the tissue or organ optionally has already been diagnosed as being affected by a tumor disease, e.g. by visual inspection or culture testing of cells of said tissue or organ. In this embodiment, the presence of said nucleic acid, said peptide, said antibody, said T cell and/or said cell which is to be detected and/or the quantity of which is to be determined and/or a quantity of said nucleic acid, said peptide, said antibody, said T cell and/or said cell which is increased compared to a reference level, e.g. compared to a patient without a tumor disease, may indicate that the tumor disease is metastatic ovarian cancer or metastatic lung cancer. Preferred biological samples for such testing may comprise tissue which is known to be susceptible to such metastatic cancers. Such tissues are described herein.

The indication of the presence of or risk for metastatic ovarian cancer or metastatic lung cancer in a patient by the methods of the invention may also indicate the presence of or risk for ovarian cancer and lung cancer in said patient.

The methods for diagnosis, detection or monitoring of a tumor disease of the invention also include embodiments wherein by detection or determination of the quantity of said nucleic acid, said peptide, said antibody, said T cell and/or said cell it is possible to assess and/or prognose the metastatic behavior of a tumor disease, wherein, preferably, the presence of said nucleic acid, said peptide, said antibody, said T cell and/or said cell and/or a quantity of said nucleic acid, said peptide, said antibody, said T cell and/or said cell which is increased compared to a reference level, e.g. a patient without said disease or without a metastasis of said disease, may indicate a metastatic behavior of a tumor disease or a risk for a metastatic behavior of a tumor disease.

In one embodiment, the biological sample is from a tissue or organ wherein the cells when the tissue or organ is free of tumors do not substantially express a tumor antigen identified according to the invention and/or a tumor nucleic acid identified according to the invention. In one embodiment, the tumor disease is in said tissue or organ.

The methods of monitoring according to the invention preferably comprise a detection of and/or determination of the quantity of one or more of the parameters mentioned above in a first sample at a first point in time and in a further sample at a second point in time, wherein the regression, progression, course and/or onset of a tumor disease may be determined by comparing the two samples.

A quantity of said nucleic acid, said peptide, said antibody, said T cell and/or said cell which is decreased in a biological sample compared to a biological sample taken earlier from a patient may indicate a regression, a positive course, e.g. a successful treatment, or a reduced risk for an onset of a tumor disease in said patient.

In one embodiment, the biological sample is from a tissue or organ wherein the cells when the tissue or organ is free of tumors do not substantially express a tumor antigen identified according to the invention and/or a tumor nucleic acid identified according to the invention. In one embodiment, the tumor disease is in said tissue or organ.

A quantity of said nucleic acid, said peptide, said antibody, said T cell and/or said cell which is increased in a biological sample compared to a biological sample taken earlier from a patient may indicate a progression, a negative course, e.g. an unsuccessful treatment, recurrence or metastatic behaviour, an onset or a risk for an onset of a tumor disease in said patient.

In one embodiment, the biological sample is from a tissue or organ wherein the cells when the tissue or organ is free of tumors do not substantially express a tumor antigen identified according to the invention and/or a tumor nucleic acid identified according to the invention. In one embodiment, the tumor disease is in said tissue or organ.

In a particular aspect, the invention relates to a method for detection, i.e. determining the position or site, of a tumor disease, e.g. a particular tissue or organ. In one embodiment said method comprises administering an antibody which binds to a tumor antigen identified according to the present invention and which is coupled to a detectable label to a patient. In one embodiment, said antibody binds to a peptide comprising an amino acid sequence selected from the group consisting of SEQ ID NOs: 3, 4 and 5 of the sequence listing or a fragment thereof, or a variant of said amino acid sequence or fragment. The antibody may be a monoclonal antibody. In further embodiments, the antibody is a chimeric, human or humanized antibody, a fragment of an antibody or a synthetic antibody.

Labelling of a tissue or organ in said patient may indicate the presence of or risk for a tumor disease in said tissue or organ.

In one embodiment, the tissue or organ is a tissue or organ wherein the cells when the tissue or organ is free of tumors do not substantially express a tumor antigen identified according to the invention and/or a tumor nucleic acid identified according to the invention.

In one embodiment, the tissue or organ is a tissue or organ wherein the cells when the tissue or organ is free of tumors do not substantially express a tumor antigen identified according to the invention and/or a tumor nucleic acid identified according to the invention and the tissue or organ has already been diagnosed as being affected by a tumor disease, e.g. by visual inspection or culture testing of cells of said tissue or organ. In this embodiment, the labelling of the tissue or organ may indicate that the tumor disease is metastatic ovarian cancer or metastatic lung cancer.

The indication of the presence of or risk for metastatic ovarian cancer or metastatic lung cancer in a tissue or organ by the methods of the invention may also indicate the presence of or risk for ovarian cancer and lung cancer in the patient.

Preferably the tumor disease in the methods for diagnosis, detection or monitoring of a tumor disease of the invention is a tumor disease of a tissue other than placenta tissue. Preferably, said tissue is tissue of ovary, lung, breast, duodenum, skin, colon, liver, lymph node, stomach, spleen, kidney, esophagus, pancreas, endometrium, brain, gallbladder, urinary bladder, ileum, adrenal gland, rectum and skeletal muscle, preferably tissue of ovary or tissue of lung. In a further aspect, the tumor disease is selected from the group consisting of ovarian cancer, lung cancer, metastatic ovarian cancer and metastatic lung cancer.

A positive diagnosis of a tumor disease and/or a metastatic tumor disease and/or a recurrence of a tumor disease as described above using the methods of the present invention may indicate a tumor disease and/or a metastatic tumor disease and/or a recurrence of a tumor disease which is amenable to the methods of treatment described herein.

Circulating tumor cells (CTCs) have been observed in the peripheral blood of patients with epithelial-derived cancers at ultra low concentrations. The number of these cells has been shown to correlate with outcome for cohorts of metastatic cancer patients with progressive disease at the time of sampling. Some reports suggest a prognostic role for circulating tumor cells in patients affected by colon cancer. Consequently, an instrument for measuring circulating tumor cells, could be a valuable diagnostic tool.

The tumor nucleic acids and tumor antigens identified according to the present invention are useful in methods for detecting circulating tumor cells in a patient. The methods may indicate the presence of metastatic cancer or an early stage cancer. In one aspect of the method, the presence of circulating tumor cells in the specimen indicates the likelihood of cancer recurrence in the mammalian subject. In a further aspect of the method, the presence of the circulating tumor cells in the specimen indicates the cancer remission status in the mammalian subject.

Accordingly, the present invention relates to a method for detecting circulating tumor cells in a patient comprising the detection of and/or determination of the quantity of (i) a nucleic acid which comprises the nucleic acid sequence of a tumor nucleic acid identified according to the invention/a nucleic acid which codes for a peptide comprising the amino acid sequence of a tumor antigen identified according to the invention and/or (ii) a peptide comprising the amino acid sequence of a tumor antigen identified according to the invention or of a tumor antigen peptide derived from said tumor antigen in a biological sample containing or suspected of containing disseminating or circulating tumor cells or metastatic tumor cells isolated from said patient. Preferably the patient is a patient having a tumor disease, being suspected of having or falling ill with a tumor disease or having a potential for a tumor disease.

Thus, in the methods for detecting circulating tumor cells of the invention tumor nucleic acids identified according to the invention and/or tumor antigens identified according to the invention or tumor antigen peptides derived therefrom are used as target molecules to identify cells which are characterized by the presence of said target molecules. These cells are likely to represent circulating tumor cells.

In one embodiment, the nucleic acid or the peptide is detected or its quantity determined in situ in a cell, preferably a tumor cell. In one embodiment, the peptide is detected or its quantity determined in situ on the surface of a cell, either incorporated in the plasma membrane or in a complex with MHC class I or class II, preferably MHC class I. Means for accomplishing said detection and/or determination of the quantity of such target molecules are described herein and will be apparent to the skilled person.

A biological sample containing or suspected of containing disseminating or circulating tumor cells or metastatic tumor cells includes, for example, blood, serum, abdominal fluid, bone marrow, sputum, bronchial aspirate, and/or bronchial lavage.

In one aspect of the method, the presence of said nucleic acid according to (i) and/or said peptide according to (ii) in said biological sample or a quantity of said nucleic acid and/or said peptide in said biological sample which is increased compared to a reference level indicates the presence of circulating tumor cells in said patient.

In one aspect of the method, the presence of circulating tumor cells in the sample may indicate the presence of or risk for a tumor disease, in particular a metastatic tumor disease in the patient. In a further aspect, the presence of circulating tumor cells in the sample may indicate the presence of or risk for an early stage tumor disease in the patient. In a further aspect, the presence of circulating tumor cells in said patient may indicate the presence of or risk for a tumor disease selected from the group consisting of ovarian cancer, lung cancer, metastatic ovarian cancer, and metastatic lung cancer.

In particular embodiments, the methods of the invention make possible to assess and/or prognose the success of a cancer therapy which has been administered or will be administered. In one aspect of the method, the presence of the circulating tumor cells in the sample may indicate the presence of or risk for tumor metastasis or tumor recurrence in the patient. In a further aspect of the method, the presence of the circulating tumor cells in the sample may indicate the tumor remission status in the patient.

The detection of circulating tumor cells using the methods for detecting circulating tumor cells of the invention may indicate a tumor disease and/or a metastasis of a tumor disease and/or a relapse of a tumor disease which is amenable to the methods of treatment described herein.

In a detailed aspect, the presence of the circulating tumor cells in the sample may indicate the presence of or risk for cancer including, but not limited to, lymphoma, myeloma, neuroblastoma, breast cancer, ovarian cancer, lung cancer, rhabdomyosarcoma, small-cell lung tumors, primary brain tumors, stomach cancer, colon cancer, pancreatic cancer, urinary bladder cancer, testicular cancer, thyroid cancer, neuroblastoma, esophageal cancer, genitourinary tract cancer, cervical cancer, endometrial cancer, adrenal cortical cancer, or prostate cancer.

Preferably, such assay for circulating tumor cells is performed using antibodies directed against target peptides wherein said antibodies are detectably labeled. In one particular embodiment, such assay for circulating tumor cells is performed using immunofluorescence assays via monoclonal antibodies directed against target peptides and is preferably performed on peripheral blood of patients. In one embodiment, said antibodies bind to a peptide comprising an amino acid sequence selected from the group consisting of SEQ ID NOs: 3, 4 and 5 of the sequence listing or a fragment thereof, or a variant of said amino acid sequence or fragment.

The presence of circulating tumor cells in blood can be correlated with a metastatic tumor disease or a risk for a metastatic tumor disease and with poor outcome and lower survival rate.

The most reliable method currently available for CTC detection is automated digital microscopy (ADM) using image analysis for recognition of immunocytochemically labeled tumor cells. ADM, however, is disadvantaged by its very slow scan speeds of 800 cells/sec. Kraeft et al, Clin Cancer Res 10: 3020-8, 2004. The ADM scan speed is constrained by the latency associated with stepping the sample many times due to the limited field of view.

To circumvent this speed constraint, several CTC enrichment technologies have been developed to reduce the total number of cells that need scanning. To date the most successful of these enrichment approaches is immunomagnetic enrichment (IME). Smirnov et al, Cancer Res 65: 4993-7, 2005; Allard et al, Clin Cancer Res 10: 6897-904, 2004; Cristofanilli et al, N EnglJ Med 351: 781-91, 2004. In most implementations of IME, monoclonal antibodies conjugated to small magnetic beads target the epithelial cell adhesion molecule, EpCAM. The beads are then manipulated in magnetic fields for enrichment.

A further aspect of the invention relates to a method of detecting metastatic ovarian cancer cells or metastatic lung cancer cells in a patient comprising the detection of and/or determination of the quantity of (i) a nucleic acid which comprises the nucleic acid sequence of a tumor nucleic acid identified according to the invention/a nucleic acid which codes for a peptide comprising the amino acid sequence of a tumor antigen identified according to the invention, and/or (ii) a peptide comprising the amino acid sequence of a tumor antigen identified according to the invention or of a tumor antigen peptide derived from said tumor antigen, in a biological sample isolated from a tissue or organ of said patient having a tumor wherein the cells when the tissue or organ is free of tumors do not substantially express said nucleic acid or peptide.

Thus, in the methods of detecting metastatic ovarian cancer cells or metastatic lung cancer cells tumor nucleic acids identified according to the invention and/or tumor antigens identified according to the invention or tumor antigen peptides derived therefrom are used as target molecules to identify tumor cells which are characterized by the presence of said target molecules. These cells are likely to represent metastatic ovarian cancer cells or metastatic lung cancer cells. In one embodiment, the nucleic acid or the peptide is detected or its quantity determined in situ in a cell, preferably a tumor cell.

In one embodiment, the peptide is detected or its quantity determined in situ on the surface of a cell, either incorporated in the plasma membrane or in a complex with MHC class I or class II, preferably MHC class I. Means for accomplishing said detection and/or determination of the quantity of such target molecules are described herein and will be apparent to the skilled person.

According to the invention a nucleic acid and/or a peptide is not substantially expressed if the level of expression is lower compared to expression in placenta cells or placenta tissue and/or is lower compared to expression in ovarian tumor cells and/or lung tumor cells or ovarian tumor tissue and/or lung tumor tissue. Preferably, the level of expression is less than 10%, preferably less than 5%, 3%, 2%, 1%, 0.5%, 0.1% or 0.05% or even lower compared to the above cells or tissues. Preferably, a nucleic acid and/or a peptide is not substantially expressed if the level of expression is below the detection limit.

Preferably, the tissue is a tissue other than placenta tissue and preferably is a tissue other than ovarian tissue or lung tissue. Preferably, said tissue is tissue of breast, duodenum, skin, colon, liver, lymph node, stomach, spleen, kidney, esophagus, pancreas, endometrium, brain, gallbladder, urinary bladder, ileum, adrenal gland, rectum and skeletal muscle. Preferably, such tissue is a tissue which is known to be susceptible to metastatic ovarian cancer and/or metastatic lung cancer. Such tissues are described herein.

Preferably, the tissue or organ has already been diagnosed as being affected by a tumor disease by visual inspection or culture testing of cells of said tissue organ.

In one aspect of the method, the presence of said nucleic acid according to (i) and/or said peptide according to (ii) in said biological sample or a quantity of said nucleic acid and/or peptide in said biological sample which is increased compared to a reference level indicates the presence of or risk for metastatic ovarian cancer cells or metastatic lung cancer cells in said tissue or organ. The presence of metastatic ovarian cancer cells or metastatic lung cancer cells in said tissue or organ may also indicate the presence of or risk for ovarian cancer and lung cancer in said patient.

A positive diagnosis of metastatic ovarian cancer cells or metastatic lung cancer cells may indicate that the tumor of the tissue or organ from which the biological sample has been isolated is amenable to the methods of treatment described herein.

A further object of this invention relates to diagnostic test kits useful in the methods for diagnosis, detection or monitoring and in the methods for detecting circulating tumor cells and/or in the methods of detecting metastatic ovarian cancer cells or metastatic lung cancer cells of the invention. These kits in one embodiment comprise a ligand that specifically binds to a target molecule as defined above and, optionally, a detectable label, e.g. indicator enzymes, a radiolabels, fluorophores, or paramagnetic particles. In a particular embodiment, the ligand comprises nucleic acid primers or probes specific for target nucleic acids as described above, or an antibody or a derivative thereof, specific for a target peptide as described above. In one embodiment, said antibody is specific for a peptide comprising an amino acid sequence selected from the group consisting of SEQ ID NOs: 3, 4 and 5 of the sequence listing or a fragment thereof, or a variant of said amino acid sequence or fragment. Kits may include informative pamphlets, for example, pamphlets informing one how to use reagents to practice a method disclosed herein.

In a further aspect, the invention relates to a recombinant nucleic acid molecule, in particular DNA or RNA molecule, which comprises a nucleic acid which codes for a peptide comprising the amino acid sequence of a tumor antigen or of a tumor antigen peptide derived from said tumor antigen.

The invention also relates to host cells which comprise a recombinant nucleic acid molecule of the invention. Preferably, such host cells express the encoded peptide.

The host cell may be a recombinant cell and may secrete the encoded peptide, may express it on the surface and preferably may additionally express an MHC molecule which binds to said peptide or a procession product thereof. In one embodiment, the host cell expresses the MHC molecule endogenously. In a further embodiment, the host cell expresses the MHC molecule and/or the peptide or the procession product thereof in a recombinant manner. The host cell is preferably nonproliferative. In a preferred embodiment, the host cell is an antigen-presenting cell, in particular a dendritic cell, a monocyte or a macrophage.

In a further aspect, the invention relates to a peptide comprising the amino acid sequence of a tumor antigen identified according to the invention or of a tumor antigen peptide derived from said tumor antigen, or a derivative of said peptide. In one embodiment, said peptide comprises an amino acid sequence selected from the group consisting of SEQ ID NOs: 3, 4 and 5 of the sequence listing or a fragment thereof, or a variant of said amino acid sequence or fragment.

In a further aspect, the invention relates to an agent which binds to a peptide comprising the amino acid sequence of a tumor antigen identified according to the invention or of a tumor antigen peptide derived from said tumor antigen, or a derivative of said peptide. In one embodiment, said peptide comprises an amino acid sequence selected from the group consisting of SEQ ID NOs: 3, 4 and 5 of the sequence listing or a fragment thereof, or a variant of said amino acid sequence or fragment. In a preferred embodiment, the agent is a protein or peptide, in particular an antibody, a T cell receptor or an MHC molecule. In further embodiments, the antibody is a monoclonal, chimeric, human or humanized antibody, an antibody produced by combinatory techniques, a fragment of an antibody, or a synthetic antibody.

The invention furthermore relates to a conjugate between an agent of the invention which binds to a peptide comprising the amino acid sequence of a tumor antigen identified according to the invention or of a tumor antigen peptide derived from said tumor antigen, or a derivative of said peptide and a therapeutic effector moiety or a detectable label.

DETAILED DESCRIPTION OF THE INVENTION

Some aspects of the present invention envision the immunotherapy of tumor diseases, in particular cancer diseases, utilizing the tumor nucleic acids and tumor antigens identified according to the invention by means of active or passive immunotherapeutic approaches which can be summarized as follows:

Immunotherapy

I. Active immunotherapy ("Cancer vaccines")
Immunisation with:
i) antigen or peptide (native or modified)
ii) nucleic acid encoding the antigen or peptide
iii) recombinant cells encoding the antigen or peptide
iv) recombinant viruses encoding the antigen or peptide
v) antigen presenting cells pulsed with antigen or peptide (native or modified) or transfected with nucleic acids encoding the antigen or peptide II. Passive immunotherapy ("Adoptive immunotherapy")
vi) Transfer of antibodies or T cell receptors that recognise antigen
vii) Transfer of cells sensitized in vitro to antigen (bulk or cloned populations)
viii) Transfer of effector cells (or stem cells) transduced with nucleic acids encoding T cell receptors that recognise antigen and preferably are responsive to tumor-specific class I MHC presented peptides In the past few years, much attention has been given to the role of CD8+ T cells in tumor immunity. Tumor-specific CD8+ CTLs have been shown to be capable of lysing tumor cells directly and eradicating tumor masses in vivo in animal models. However, CD4+ T cells are also thought to play a critical role and it may be that optimal cancer vaccines require the participation of both CD4+ and CD8+ T cells.

Immunisation with intact or substantially intact tumor antigen has the potential advantage of simultaneously immunising against both class I and class II epitopes but requires extensive and time-consuming efforts to purify large amounts of tumor antigen. The identification of MHC class I and class II peptides within a tumor antigen makes it possible to immunise with high levels of pure synthetic peptide. The peptide approach also has the advantage that one can choose between a MHC class I and a class II type response (or mixture) by choosing which epitopes to use. Immunisation with peptide also means that subdominant and/or cryptic epitopes can be chosen (as the need for antigen processing may be bypassed or reduced to a "trimming" role) in order to stimulate a different subset of T cells. Also the peptide may be modified (for example at their HLA class I or II anchor sites) to increase its immunogenicity.

The invention relates to tumor-specific class I MHC presented peptides and methods of using the same, as well as cytotoxic T lymphocytes (CTLs) responsive to tumor-specific class I MHC presented peptides and methods of using the same.

In one aspect, the invention provides anti-tumor vaccines capable of stimulating a cellular response against a tumor characterized by presentation of a tumor antigen identified according to the invention with class I MHC. The anti-tumor vaccines of the invention preferably comprise a tumor antigen peptide, or a tumor antigen peptide nucleic acid.

The invention also encompasses the use of nucleic acids encoding one or more of the tumor antigens identified according to the invention or one or more tumor antigen peptides derived therefrom. It is anticipated that the antigens or peptides so encoded are effective as therapeutic or prophylactic anti-tumor vaccines. For example, a particular contemplated application of these nucleic acids involves the induction of a cellular response such as a CTL response and/or a humoral immune response against such antigens.

Immunization with plasmid DNA can elicit antigen-specific immune responses consisting of CD8+ T cells, CD4+ T cells, and antibodies. DNA can be administered by the gene gun method of immunization. In gene gun immunization, plasmid DNA may be coated onto gold particles followed by delivery of the DNA-coated particles into the skin by a high-pressure, helium-driven gene gun.

Advances in molecular biology have made it possible to construct recombinant viruses that encode tumor antigens or tumor antigen peptides as described herein. Several recombinant viral vaccines have been used up to now.

Several viral vectors have shown promising results with regard to their potential to enhance immunotherapy of malignant diseases. Replication competent and replication incompetent viruses can be used, with the latter group being preferred. Herpes virus, adenovirus, vaccinia, reovirus, and New Castle Disease viruses are examples of preferred viruses useful according to the present invention.

Antigen presenting cells (APC) such as dendritic cells (DCs) can be loaded with either MHC class I-presented peptides or tumor lysate, or transduced with nucleic acid such as by transduction using adenovirus encoding a tumor antigen.

In a preferred embodiment, an anti-tumor vaccine of the invention comprises an APC loaded with tumor antigen peptide. In this respect, protocols may rely on in vitro culture/differentiation of DCs manipulated in such a way that they artificially present tumor antigen peptide. Production of genetically engineered DCs may involve introduction of nucleic acids encoding tumor antigens or tumor antigen peptides into DCs. Transfection of DCs with mRNA is a promising antigen-loading technique of stimulating strong antitumor immunity.

Dendritic cells (DCs) are leukocyte populations that present antigens captured in peripheral tissues to T cells via both MHC class II and I antigen presentation pathways. It is well known that DCs are potent inducers of immune responses and the activation of these cells is a critical step for the induction of antitumoral immunity. DC maturation is referred to as the status of DC activation at which such antigen-presenting DCs leads to T-cell priming, while its presentation by immature DCs results in tolerance. DC maturation is chiefly caused by biomolecules with microbial features detected by innate receptors (bacterial DNA, viral RNA, endotoxin, etc), pro-inflammatory cytokines (TNF, IL-1, IFNs), ligation of CD40 on the DC surface by CD40L, and substances released from cells undergoing stressful cell death. The DCs can be derived by culturing bone marrow cells in vitro with cytokines, such as granulocyte-macrophage colony-stimulating factor (GM-CSF) and tumor necrosis factor alpha.

Yet another embodiment of the invention comprises the preparation of antibodies, preferably monoclonal antibodies against a target antigen as defined above. Such monoclonal antibodies may be produced by conventional methods and include fragments or derivatives thereof, including, without limitation, human monoclonal antibodies, humanized monoclonal antibodies, chimeric monoclonal antibodies, single chain antibodies, e.g., scFv's and antigen-binding antibody fragments such as Fab and Fab' fragments. Methods for the preparation of monoclonal antibodies are known in the art. In general, the preparation of monoclonal antibodies comprises immunization of an appropriate host with the subject antigens, isolation of immune cells therefrom, use of such immune cells to isolate monoclonal antibodies and screening for monoclonal antibodies that specifically bind to either of such antigens. Antibody fragments may be prepared by known methods, e.g., enzymatic cleavage of monoclonal antibodies.

These monoclonal antibodies and fragments are useful for passive anti-tumor immunotherapy, or may be attached to therapeutic effector moieties, e.g., radiolabels, cytotoxins, therapeutic enzymes, agents that induce apoptosis, and the like in order to provide for targeted cytotoxicity, i.e., killing of tumor cells. In one embodiment of the present invention, such antibodies or fragments are administered in labeled or unlabeled form, alone or in conjunction with other therapeutics, e.g., chemotherapeutics such as cisplatin, methotrexate, adriamycin, and the like suitable for cancer therapy.

If used for passive anti-tumor immunotherapy, antibodies may or may not be attached to therapeutic effector moieties. Preferably the antibodies described herein mediate killing of cells by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis. The antibodies described herein preferably interact with components of the immune system, preferably through ADCC or CDC. However, antibodies of the invention may also exert an effect simply by binding to tumor antigens on the cell surface, thus, e.g. blocking proliferation of the cells.

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that also leads to antigen presentation and the induction of tumor-directed T-cell responses. Preferably, in vivo induction of ADCC will lead to tumor-directed T-cell responses and host-derived antibody responses.

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell and may lead to apoptosis.

Passive immunotherapy with immune cells (optionally genetically modified) capable of recognizing tumor antigens is effective in mediating the regression of cancer in selected patients. These techniques may be based on ex-vivo reactivation and expansion of cloned or polyclonal cultures of tumor reactive T cells. After culture, T cells may be reinfused into the patient along with IL-2. In vitro techniques have been developed in which human lymphocytes are sensitized in vitro to tumor antigen peptides presented on antigen presenting cells. By repetitive in vitro stimulation cells can be derived with a great capacity to recognize human tumor antigens. The adoptive transfer of these cells may be more effective in mediating tumor regression in vivo than are conventionally grown cells.

In one embodiment, autologous cytotoxic lymphocytes or tumor infiltrating lymphocytes may be obtained from a patient with cancer. The lymphocytes may be grown in culture and tumor antigen-responsive CTLs expanded by culturing in the presence of tumor antigen peptide presented with MHC class I, alone or in combination with at least one immunomodulatory agent, preferably additionally with cytokines. The tumor antigen-responsive CTLs are then infused back into the patient in an amount effective to reduce or eliminate the tumors in the patient.

Patients could be pre-stimulated with an anti-tumor peptide vaccine prior lymphocyte harvest if the existing response was inadequate. It is expected that the adoptively transferred CTLs would survive best with IL-2 infusion at low to intermediate doses.

By "tumor antigen-responsive CTL" is meant a CD8+ T cell that is responsive to a tumor antigen peptide derived from said tumor antigen, which is presented with class I MHC, e.g. on the surface of tumor cells.

According to the invention, CTL responsiveness may include sustained calcium flux, cell division, production of cytokines such as IFN-gamma and TNF-alpha, upregulation of activation markers such as CD44 and CD69, and specific cytolytic killing of tumor antigen expressing target cells. CTL responsiveness may also be determined using an artificial reporter that accurately indicates CTL responsiveness.

By "tumor antigen peptide" or "tumor antigen peptide derived from a tumor antigen" is meant an oligopeptide or polypeptide comprising an amino acid sequence substantially corresponding to the amino acid sequence of a fragment or peptide of a tumor antigen identified according to the present invention. Preferably, a tumor antigen peptide is capable of stimulating a cellular response against a tumor characterized by presentation of a tumor antigen identified herein with class I MHC and preferably a tumor antigen-responsive CTL and/or of eliciting antibodies that specifically bind to a tumor antigen identified according to the present invention when used itself or attached to an immunogenic carrier. A tumor antigen peptide according to the invention preferably is a peptide comprising a sequence substantially corresponding to the sequence of a fragment of the amino acid sequence according to SEQ ID NO: 2 of the sequence listing or is a derivative of said peptide. In one embodiment, said peptide comprises an amino acid sequence selected from the group consisting of SEQ ID NOs: 3, 4 and 5 of the sequence listing or a fragment thereof, or a variant of said amino acid sequence or fragment. A tumor antigen peptide may be of any length.

If a tumor antigen peptide is to be presented directly, i.e. without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of a tumor antigen peptide which is to be presented directly is derived from the amino acid sequence of a tumor antigen identified according to the invention, i.e. its sequence substantially corresponds and is preferably completely identical to a fragment of a tumor antigen identified according to the invention. If a tumor antigen peptide is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of the peptide which is to be presented following processing is derived from the amino acid sequence of a tumor antigen identified according to the invention, i.e. its sequence substantially corresponds and is preferably completely identical to a fragment of a tumor antigen identified according to the invention. Thus, a tumor antigen peptide according to the invention in one embodiment comprises a sequence of 7-20 amino acids in length, more preferably 7-12 amino acids in length, more preferably 8-11 amino acids in length, in particular 9 or 10 amino acids in length which substantially corresponds and is preferably completely identical to a fragment of a tumor antigen identified according to the invention and following processing of the tumor antigen peptide makes up the presented peptide. However, the tumor antigen peptide may also comprise a sequence which substantially corresponds and preferably is completely identical to a fragment of a tumor antigen identified according to the invention which is even longer than the above stated sequence. In one embodiment, a tumor antigen peptide may comprise the entire sequence of a tumor antigen identified according to the invention.

Preferably, a tumor antigen peptide may be presented, directly or following processing, with class I MHC molecules, and when so presented is capable of stimulating a tumor antigen-responsive CTL. Peptides having amino acid sequences substantially corresponding to a sequence of a peptide which is presented by the class I MHC may differ at one or more residues that are not essential for TCR recognition of the peptide as presented by the class I MHC, or for peptide binding to MHC. Such substantially corresponding peptides are also capable of stimulating a tumor antigen-responsive CTL. Peptides having amino acid sequences differing from a presented peptide at residues that do not affect TCR recognition but improve the stability of binding to MHC may improve the immunogenicity of the tumor antigen peptide, and may be referred to herein as "optimized peptides". Using existing knowledge about which of these residues may be more likely to affect binding either to the MHC or to the TCR, a rational approach to the design of substantially corresponding peptides may be employed. Resulting peptides that are functional are contemplated as tumor antigen peptides.

By "immunoreactive cell" is meant a cell which can mature into an immune cell (such as a B cell, a helper T cell, or a CTL) upon appropriate stimulation. Thus immunoreactive cells include CD34+ hematopoietic stem cells, immature T cells and immature B cells. When it is desired to produce CTLs which recognize a tumor antigen, the immunoreactive cell is contacted with a cell which presents the tumor antigen or a tumor antigen peptide derived from said tumor antigen under conditions favoring production, differentiation and/or selection of CTLs.

By "cell characterized by presentation of a tumor antigen with class I MHC" or "cell presenting a tumor antigen with class I MHC" or similar expressions is meant a cell such as a tumor cell or an antigen presenting cell presenting the tumor antigen it expresses or a fragment derived from said tumor antigen, e.g. by processing of the tumor antigen, in the context of MHC Class I molecules. Similarly, the term "tumor characterized by presentation of a tumor antigen with class I MHC" denotes a tumor comprising cells characterized by presentation of a tumor antigen with class I MHC.

By "fragment of a tumor antigen identified according to the invention which is presented" or similar expressions is meant that the fragment can be presented by MHC class I or class II, preferably MHC class I, e.g. when added directly to antigen presenting cells. In one embodiment, the fragment is a fragment which is naturally presented by cells expressing a tumor antigen identified according to the invention, e.g. tumor cells.

By "cell that recognizes a tumor antigen or a tumor antigen peptide derived from said tumor antigen" or "immunoreactive cell that recognizes a tumor antigen or a tumor antigen peptide derived from said tumor antigen" or similar expressions is meant a cell that is able to recognize said tumor antigen or a tumor antigen peptide derived from said tumor antigen with some degree of specificity, in particular if presented in the context of MHC molecules such as on the surface of antigen presenting cells or tumor cells. Preferably, said recognition enables the cell that recognizes a tumor antigen or a tumor antigen peptide derived from said tumor antigen to be responsive. If the cell is a helper T cell (CD4+ T cell) bearing receptors that recognize a tumor antigen or a tumor antigen peptide derived from said tumor antigen in the context of MHC class II molecules such responsiveness may involve the release of cytokines and/or the activation of CD8+ lymphocytes (CTLs) and/or B cells. If the cell is a CTL such responsiveness may involve the elimination of cells presented in the context of MHC class I molecules, i.e. cells characterized by presentation of a tumor antigen with class I MHC, for example via apoptosis or perforin-mediated cell lysis. Such CTL that recognizes a tumor antigen or a tumor antigen peptide derived from said tumor antigen and are responsive are also termed "tumor antigen-responsive CTL" herein. If the cell is a B cell such immune such responsiveness may involve the release of immunoglobulins.

By "T cell receptor that recognizes a tumor antigen or a tumor antigen peptide derived from said tumor antigen" is meant a T cell receptor that is able to recognize said tumor antigen or a tumor antigen peptide derived from said tumor antigen with some degree of specificity, in particular if presented in the context of MHC molecules. Preferably, said recognition enables the cell carrying the T cell receptor that recognizes a tumor antigen or a tumor antigen peptide derived from said tumor antigen to be responsive as outlined above.

A "cellular response against a tumor antigen" is meant to include a cellular response directed to cells characterized by presentation of a tumor antigen with class I or class II MHC. The cellular response relates to cells called T cells or T lymphocytes which act as either 'helpers' or 'killers'. The helper T cells (also termed CD4+ T cells) play a central role by regulating the immune response and the killer cells (also termed cytotoxic T cells, cytolytic T cells, CD8+ T cells or CTLs) kill tumor cells, preventing the production of more tumor cells. Although both arms of the immune response are thought to be necessary, the CTL response may be more important for controlling cancer.

According to the invention, a "reference" such as a reference sample or reference organism may be used to correlate and compare the results obtained in the methods of the invention from a test sample or test organism, i.e. a patient. Typically the reference organism is a healthy organism, in particular an organism which does not suffer from a tumor disease.

A "reference value" or "reference level" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

According to the invention, the term "binding" preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than $10^2$-fold, $10^3$-fold, $10^4$-fold, $10^5$-fold, $10^6$-fold, $10^7$-fold, $10^8$-fold, $10^9$-fold, or $10^{10}$-fold lower than the dissociation constant ($K_D$) for the target to which the agent does not bind specifically.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

The terms "tumor nucleic acid identified according to the invention" and "nucleic acid encoding a tumor antigen identified according to the invention" have similar meanings.

As used herein, the term "RNA" means a molecule comprising at least one ribonucleotide residue. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA.

Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

If reference is made herein to the detection of or the determination of the quantity of a nucleic acid, the nucleic acid which is actually to be detected or the quantity of which is actually to be determined is preferably mRNA. However, it should be understood that this may also include embodiments wherein mRNA is detected or the quantity of mRNA is determined indirectly. For example, mRNA may be transformed into cDNA and the cDNA detected or its quantity determined. mRNA is given herein as the cDNA equivalent. One skilled in the art would understand that the cDNA sequence is equivalent to the mRNA sequence, and can be used for the same purpose herein, e.g., the generation of probes hybridizing to the nucleic acid to be detected. Thus, if reference is made herein to the sequences shown in the sequence listing this is also to include the RNA equivalents of said sequences.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

The term "variant" with respect to, for example, nucleic acid and amino acid sequences, according to the invention includes any variants, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code.

Furthermore, a "variant" of a specific nucleic acid sequence according to the invention includes nucleic acid sequences comprising single or multiple such as at least 2, at least 4, or at least 6 and preferably up to 3, up to 4, up to 5, up to 6, up to 10, up to 15, or up to 20 nucleotide substitutions, deletions and/or additions.

Preferably the degree of identity between a given nucleic acid sequence and a nucleic acid sequence which is a variant of said given nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "percentage identity" is intended to denote a percentage of nucleotides or of amino acid residues which are identical between the two sequences to be compared, obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

A nucleic acid is "capable of hybridizing" or "hybridizes" to another nucleic acid if the two sequences are complementary with one another. A nucleic acid is "complementary" to another nucleic acid if the two sequences are capable of forming a stable duplex with one another. According to the invention, hybridization is preferably carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, New York, 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the invention is at least 70%, preferably at least 75%, preferably at least 80%, more preferably at least 85%, even more preferably at least 90% or most preferably at least 95%, 96%, 97%, 98% or 99%. Most preferably, the degree of complementarity according to the invention is 100%.

The term "derivative" comprises any chemical derivatization of a nucleic acid on a nucleotide base, on the sugar or on the phosphate. The term "derivative" also comprises nucleic acids which contain nucleotides and nucleotide analogs not occurring naturally. Preferably, a derivatization of a nucleic acid increases its stability.

Nucleic acids coding for tumor antigens or tumor antigen peptides may, according to the invention, be present alone or in combination with other nucleic acids, in particular heterologous nucleic acids. Preferably, a nucleic acid coding for a tumor antigen or tumor antigen peptide expresses said tumor antigen or tumor antigen peptide. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5' untranscribed and 5' untranslated sequences which are involved in initiation of transcription and translation, respectively, such as TATA box, capping sequence, CAAT sequence, and the like. More specifically, 5' untranscribed regulatory sequences comprise a promoter region which includes a promoter sequence for transcriptional control of the functionally linked gene. Regulatory sequences may also comprise enhancer sequences or upstream activator sequences.

According to the invention, a nucleic acid may furthermore be present in combination with another nucleic acid which codes for a peptide controlling secretion of the protein or peptide encoded by said nucleic acid from a host cell. According to the invention, a nucleic acid may also be present in combination with another nucleic acid which codes for a peptide causing the encoded protein or peptide to be anchored on the cell membrane of the host cell or compartmentalized into particular organelles of said cell. Similarly, a combination with a nucleic acid is possible which represents a reporter gene or any "tag".

In a preferred embodiment, a recombinant nucleic acid molecule is according to the invention a vector, where appropriate with a promoter, which controls expression of a nucleic acid, for example a nucleic acid coding for a tumor antigen identified according to the invention. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids, bacteriophages or viral genomes.

The nucleic acids coding for a tumor antigen identified according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application.

According to the invention, the term "host cell" relates to any cell which can be transformed or transfected with an exogenous nucleic acid. The term "host cells" comprises according to the invention prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

According to the invention, the term "expression" is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1, pcDNA3.3 and pRc/CMV (Invitrogen, Carlsbad, Calif.), which contain a selectable marker such as a gene imparting resistance to G418 (and thus enabling stably transfected cell lines to be selected) and the enhancer-promoter sequences of cytomegalovirus (CMV).

In those cases of the invention in which an MHC molecule presents a tumor antigen or a tumor antigen peptide, an expression vector may also comprise a nucleic acid sequence coding for said MHC molecule. The nucleic acid sequence coding for the MHC molecule may be present on the same expression vector as the nucleic acid coding for the tumor antigen or the tumor antigen peptide, or both nucleic acids may be present on different expression vectors. In the latter case, the two expression vectors may be cotransfected into a cell. If a host cell expresses neither the tumor antigen or the tumor antigen peptide nor the MHC molecule, both nucleic acids coding therefor may be transfected into the cell either on the same expression vector or on different expression vectors. If the cell already expresses the MHC molecule, only the nucleic acid sequence coding for the tumor antigen or the tumor antigen peptide can be transfected into the cell.

"Antisense molecules" or "antisense nucleic acids" may be used for regulating, in particular reducing, expression of a nucleic acid. The term "antisense molecule" or "antisense nucleic acid" refers according to the invention to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the invention, an "antisense molecule" also comprises a construct which contains a nucleic acid or a part thereof in reverse orientation with respect to its natural promoter. An antisense transcript of a nucleic acid or of a part thereof may form a duplex with naturally occurring mRNA and thus prevent accumulation of or translation of the mRNA. Another possibility is the use of ribozymes for inactivating a nucleic acid.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3' untranslated region or mRNA splicing site.

In one embodiment, an oligonucleotide of the invention consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the invention is a "modified" oligonucleotide. Here, the oligonucleotide may be modified in very different ways, without impairing its ability to bind its target, in order to increase, for example, its stability or therapeutic efficacy. According to the invention, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having a covalently modified base and/or sugar. "Modified oligonucleotides" comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

It is to be understood that all embodiments described above with respect to oligonucleotides may also apply to polynucleotides.

By "small interfering RNA" or "siRNA" as used herein is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used to identify a target gene or mRNA to be degraded. A range of 19-25 nucleotides is the most preferred size for siRNAs.

siRNA according to the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more nucleotides in the siRNA with deoxyribonucleotides. Furthermore, siRNA may be modified to increase the stability thereof as described above for modified oligonucleotides, in particular by introducing one or more phosphorothioate linkages.

One or both strands of the siRNA can also comprise a 3'-overhang. As used herein, a "3'-overhang" refers to at least one unpaired nucleotide extending from the 3'-end of an RNA strand. Thus in one embodiment, the siRNA comprises at least one 3'-overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length. In the embodiment in which both strands of the siRNA molecule comprise a 3'-overhang, the length of the overhangs can be the same or different for each strand. In a most preferred embodiment, the 3'-overhang is present on both strands of the siRNA, and is 2 nucleotides in length.

For example, each strand of the siRNA of the invention can comprise 3'-overhangs of dideoxythymidylic acid ("TT") or diuridylic acid ("uu").

In order to enhance the stability of the siRNA, the 3'-overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

The sense and antisense strands of the siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

As used herein, "target mRNA" refers to an RNA molecule that is a target for downregulation.

siRNA can be expressed from pol III expression vectors without a change in targeting site, as expression of RNAs from pol III promoters is only believed to be efficient when the first transcribed nucleotide is a purine.

siRNA according to the invention can be targeted to any stretch of approximately 19-25 contiguous nucleotides in any of the target mRNA sequences (the "target sequence"). Techniques for selecting target sequences for siRNA are given, for example, in Tuschl T. et al., "The siRNA User Guide", revised Oct. 11, 2002, the entire disclosure of which is herein incorporated by reference. "The siRNA User Guide" is available on the world wide web at a website maintained by Dr. Thomas Tuschl, Laboratory of RNA Molecular Biology, Rockefeller University, New York, USA, and can be found by accessing the website of the Rockefeller University and searching with the keyword "siRNA". Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon.

siRNA can be obtained using a number of techniques known to those of skill in the art. For example, siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, siRNA is chemically synthesized using appropriately protected ribonucleoside phosphoramidites and a conventional DNA/RNA synthesizer. siRNA can be synthesized as two separate, complementary RNA molecules, or as a single RNA molecule with two complementary regions.

Alternatively, siRNA can also be expressed from recombinant circular or linear DNA plasmids using any suitable promoter. Such embodiments are included according to the present invention when reference is made herein to the administration of siRNA or the incorporation of siRNA into pharmaceutical compositions. Suitable promoters for expressing siRNA of the invention from a plasmid include, for example, the U6 or H1 RNA pol III promoter sequences and the cytomegalovirus promoter.

Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA to cells in vivo is discussed in more detail below. siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art.

siRNA can also be expressed from recombinant viral vectors intracellularly in vivo. The recombinant viral vectors comprise sequences encoding the siRNA and any suitable promoter for expressing the siRNA sequences. The recombinant viral vectors can also comprise inducible or regulatable promoters for expression of the siRNA in a particular tissue or in a particular intracellular environment. siRNA can be expressed from a recombinant viral vector either as two separate, complementary RNA molecules, or as a single RNA molecule with two complementary regions.

The term "peptide" comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

Such proteins and peptides may be used, for example, in producing antibodies and in an immunological or diagnostic assay or as therapeutics. Proteins and peptides described according to the invention may be isolated from biological samples such as tissue or cell homogenates and may also be expressed recombinantly in a multiplicity of pro- or eukaryotic expression systems.

For the purposes of the present invention, "variants" of a protein or peptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid deletion variants are characterized by the removal of one or more amino acids from the sequence.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties.

Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least 70%, preferably at least 80%, preferably at least 85%, even more preferably at least 90% or most preferably at least 95%, 96%, 97%, 98% or 99%. The degree of similarity or identity is given preferably for a region of at least about 20, at least about 40, at least about 60, at least about 80, at least about 100, at least about 120, at least about 140, at least about 160, at least about 200 or 250 amino acids. In preferred embodiments, the degree of similarity or identity is given for the entire length of the reference amino acid sequence.

The peptides and amino acid variants described herein may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides. Preferably, a modified peptide has increased stability and/or increased immunogenicity.

According to the invention, a variant of a nucleic acid or amino acid sequence, a substantially corresponding amino acid sequence or a fragment or derivative of a peptide preferably has a functional property of the nucleic acid or amino acid sequence, the amino acid sequence or the peptide, respectively, from which it has been derived. Such functional properties comprise the interaction with antibodies, the interaction with other peptides or proteins, the selective binding of nucleic acids and an enzymatic activity. In one embodiment, a variant of a nucleic acid or amino acid sequence, a substantially corresponding amino acid sequence or a fragment or derivative of a peptide is immunologically equivalent to the nucleic acid or amino acid sequence, the amino acid sequence or the peptide, respectively, from which it has been derived. In one embodiment, the functional property is an immunological property. A particular property is the ability to form a complex with MHC molecules and, where appropriate, generate an immune response, preferably by stimulating cytotoxic or T helper cells. A fragment of a tumor antigen preferably comprises a sequence of at least 6, in particular at least 8, at least 10, at least 12, at least 15, at least 20, at least 30 or at least 50, consecutive amino acids of the tumor antigen. A fragment of a tumor antigen preferably comprises a sequence of up to 8, in particular up to 10, up to 12, up to 15, up to 20, up to 30 or up to 55, consecutive amino acids of the tumor antigen. A fragment of a tumor antigen is preferably a part of the tumor antigen which may be presented with MHC molecules and when so presented is capable of stimulating a cellular response.

Preferred fragments of a tumor antigen are suitable for the stimulation of cytotoxic T-lymphocytes in vivo but also for the production of expanded and stimulated T-lymphocytes for the therapeutic adoptive transfer ex vivo.

Antisera which contain specific antibodies specifically binding to the target protein can be prepared by various standard processes; see, for example, "Monoclonal Antibodies: A Practical Approach" by Philip Shepherd, Christopher Dean ISBN 0-19-963722-9; "Antibodies: A Laboratory Manual" by Ed Harlow, David Lane, ISBN: 0879693142 and "Using Antibodies: A Laboratory Manual: Portable Protocol NO" by Edward Harlow, David Lane, Ed Harlow ISBN 0879695447. Thereby it is also possible to generate affine and specific antibodies which recognize complex membrane proteins in their native form (Azorsa et al., J. Immunol. Methods 229: 35-48, 1999; Anderson et al., J. Immunol. 143: 1899-1904, 1989; Gardsvoll, J. Immunol. Methods 234: 107-116, 2000). This is in particular relevant for the preparation of antibodies which are to be used therapeutically, but also for many diagnostic applications. In this respect, it is possible to immunize with the whole protein, with extracellular partial sequences as well as with cells which express the target molecule in physiologically folded form.

Monoclonal antibodies are traditionally prepared using the hybridoma technology. (for technical details see: "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142; "Using Antibodies: A Laboratory Manual: Portable Protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology*, 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as F(ab')$_2$ fragment, carries both antigen binding sites of a complete antibody. Similarly, an antibody from which the Fc region has been enzymatically removed or which has been produced without said Fc region, referred to as Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

As another example, WO 92/04381 describes the production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

According to the invention, the term "antibody" also includes F(ab')$_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric F(ab')$_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The term "antibody" also comprises "single-chain" antibodies.

Non-antibody proteins and peptides which bind specifically to tumor antigens may replace antibodies when used according to the invention. Binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Antibodies may also be coupled to a therapeutic label for displaying cells and tissues expressing tumor antigens. They may also be coupled to therapeutic effector moieties.

In one embodiment, the antibodies described herein specifically bind to a portion of the tumor antigens identified according to the invention comprising an amino acid sequence selected from the group consisting of SEQ ID NOs: 3, 4 and 5 of the sequence listing or a fragment thereof, or a variant of said amino acid sequence or fragment. In one embodiment, the antibodies described herein specifically bind to a tumor antigen peptide described herein comprising an amino acid sequence selected from the group consisting of SEQ ID NOs: 3, 4 and 5 of the sequence listing or a fragment thereof, or a variant of said amino acid sequence or fragment. Such antibodies may be obtained using a peptide comprising an amino acid sequence selected from the group consisting of SEQ ID NOs: 3, 4 and 5 of the sequence listing or a fragment thereof, or a variant of said amino acid sequence or fragment for immunization.

Detectable labels include any label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Detectable labels comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

According to the invention, the term "therapeutic effector molecule" means any molecule which may exert a therapeutic effect. According to the invention, a therapeutic effector molecule is preferably selectively guided to a cell which expresses one or more tumor antigens and includes anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "major histocompatibility complex" or "MHC" includes MHC class I and class II and relates to a complex of genes present in all vertebrates. MHC proteins or molecules are involved in signaling between lymphocytes and antigen presenting cells in normal immune reactions by binding peptides and presenting them for recognition by T cell receptors (TCR). MHC molecules bind peptides within an intracellular processing compartment and present these peptides on the surface of antigen presenting cells for recognition by T cells. The human MHC region also termed HLA is located on chromosome 6 and includes the class I and class II region. In one preferred embodiment of all aspects of the invention an MHC molecule is an HLA molecule.

"Reduce" or "inhibit" as used herein means the ability to cause an overall decrease, preferably of 20% or greater, more preferably of 50% or greater, and most preferably of 75% or greater, in the level, e.g. in the level of protein or mRNA as compared to a reference sample (e.g., a sample not treated with siRNA). This reduction or inhibition of RNA or protein expression can occur through targeted mRNA cleavage or degradation. Assays for protein expression or nucleic acid expression are known in the art and include, for example, ELISA, western blot analysis for protein expression, and northern blotting or RNase protection assays for RNA.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

According to the invention the term "increased" or "increased amount" preferably refers to an increase by at least 10%, in particular at least 20%, at least 50% or at least 100%. The amount of a substance is also increased in a test sample such as a biological sample compared to a reference sample if it is detectable in the test sample but absent or not detectable in the reference sample.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

Preferably, a tumor disease according to the invention is a cancer disease, i.e. a malignant disease and a tumor cell is a cancer cell. Preferably, a tumor disease is characterized by cells in which a tumor nucleic acid and/or tumor antigen identified according to the invention is expressed or abnormally expressed and a tumor cell or a circulating or metastatic tumor cell is characterized by expression or abnormal expression of a tumor nucleic acid and/or tumor antigen identified according to the invention. Preferably, a tumor disease, a tumor cell or a circulating or metastatic tumor cell is characterized by presentation of a tumor antigen identified according to the invention with class I MHC.

"Abnormal expression" means according to the invention that expression is altered, preferably increased, compared to the state in a healthy individual. An increase in expression refers to an increase by at least 10%, in particular at least 20%, at least 50%, at least 100%, at least 200%, at least 500%, at least 1000%, at least 10000% or even more. In one embodiment, expression is only found in a diseases tissue, while expression in a healthy tissue is repressed.

According to the invention, cells of a tissue or organ do not substantially express a tumor antigen identified according to the invention and/or a tumor nucleic acid identified according to the invention if the level of expression is lower compared to expression in placenta cells or placenta tissue and/or is lower compared to expression in ovarian tumor cells and/or lung tumor cells or ovarian tumor tissue and/or lung tumor tissue. Preferably, the level of expression is less than 10%, preferably less than 5%, 3%, 2%, 1%, 0.5%, 0.1% or 0.05% or even lower compared to the above cells or tissues. Preferably, a tumor antigen and/or a nucleic acid is not substantially expressed if the level of expression is below the detection limit. Preferably, a tissue that does not substantially express a tumor antigen identified according to the invention and/or a tumor nucleic acid identified according to the invention when the tissue is free of tumors, i.e. does not have a tumor disease, is a tissue of ovary, lung, breast, duodenum, skin, colon, liver, lymph node, stomach, spleen, kidney, esophagus, pancreas, endometrium, brain, gallbladder, urinary bladder, ileum, adrenal gland, rectum and skeletal muscle, preferably tissue of ovary or tissue of lung. Preferably such tissue is a tissue other than placenta tissue.

Preferably, a tumor disease according to the invention is cancer, wherein the term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

Preferred tumor diseases or cancers according to the invention are selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, and uterine cancer, and the metastatic forms thereof.

Particularly preferred tumor diseases or cancers according to the invention are selected from the group consisting of ovarian cancer, lung cancer, metastatic ovarian cancer and metastatic lung cancer. Preferably, the ovarian cancer is an ovarian carcinoma or an ovarian adenocarcinoma. Preferably, the lung cancer is a carcinoma or an adenocarcinoma, and preferably is bronchiolar cancer such as a bronchiolar carcinoma or bronchiolar adenocarcinoma. In one embodiment, the tumor cell is a cell of such a cancer. Metastatic ovarian cancers include metastatic ovarian carcinomas and metastatic ovarian adenocarcinomas, and metastatic lung cancers include metastatic lung carcinomas, metastatic lung adenocarcinomas, metastatic bronchiolar carcinomas, and metastatic bronchiolar adenocarcinomas.

The main types of lung cancer are small cell lung carcinoma (SCLC) and non-small cell lung carcinoma (NSCLC). There are three main sub-types of the non-small cell lung carcinomas: squamous cell lung carcinoma, adenocarcinoma, and large cell lung carcinoma. Adenocarcinomas account for approximately 10% of lung cancers. This cancer usually is seen peripherally in the lungs, as opposed to small cell lung cancer and squamous cell lung cancer, which both tend to be more centrally located.

Skin cancer is a malignant growth on the skin. The most common skin cancers are basal cell cancer, squamous cell cancer, and melanoma. Malignant melanoma is a serious type of skin cancer. It is due to uncontrolled growth of pigment cells, called melanocytes.

According to the invention, a "carcinoma" is a cancer that begins in the lining layer (epithelial cells) of organs.

"Bronchiolar carcinoma" is a carcinoma of the lung, thought to be derived from epithelium of terminal bronchioles, in which the neoplastic tissue extends along the alveolar walls and grows in small masses within the alveoli. Mucin may be demonstrated in some of the cells and in the material in the alveoli, which also includes denuded cells.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

"Cystadenocarcinoma" is a malignant form of a surface epithelial-stromal tumor, a type of ovarian cancer.

Surface epithelial-stromal tumors are a class of ovarian neoplasms that are thought to be derived from the ovarian surface epithelium (modified peritoneum) or from ectopic endometrial or Fallopian tube (tubal) tissue. This group of tumors accounts for the majority of all ovarian tumors.

Teratocarcinoma refers to a germ cell tumor that is a mixture of teratoma with embryonal carcinoma, or with choriocarcinoma, or with both. Choriocarcinoma is a malignant, trophoblastic and aggressive cancer, usually of the placenta. It is characterized by early hematogenous spread to the lungs.

A sarcoma is a cancer of the connective tissue (bone, cartilage, fat) resulting in mesoderm proliferation. This is in contrast to carcinomas, which are of epithelial origin. A synovial sarcoma is a rare form of cancer which usually occurs near to the joints of the arm or leg. It is one of the soft tissue sarcomas.

Renal cell carcinoma also known as renal cell cancer or renal cell adenocarcinoma is a kidney cancer that originates in the lining of the proximal convoluted tubule, the very small tubes in the kidney that filter the blood and remove waste products. Renal cell carcinoma is by far the most common type of kidney cancer in adults and the most lethal of all the genitorurinary tumors. Distinct subtypes of renal cell carcinoma are clear cell renal cell carcinoma and papillary renal cell carcinoma. Clear cell renal cell carcinoma is the most common form of renal cell carcinoma. When seen under a microscope, the cells that make up clear cell renal cell carcinoma appear very pale or clear. Papillary renal cell carcinoma is the second most common subtype. These cancers form little finger-like projections (called papillae) in some, if not most, of the tumors.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

In ovarian cancer, metastasis can occur in the following ways: by direct contact or extension, it can invade nearby tissue or organs located near or around the ovary, such as the fallopian tubes, uterus, bladder, rectum, etc.; by seeding or shedding into the abdominal cavity, which is the most common way ovarian cancer spreads. Cancer cells break off the surface of the ovarian mass and "drop" to other structures in the abdomen such as the liver, stomach, colon or diaphragm; by breaking loose from the ovarian mass, invading the lymphatic vessels and then traveling to other areas of the body or distant organs such as the lung or liver; by breaking loose from the ovarian mass, invading the blood system and traveling to other areas of the body or distant organs.

According to the invention, metastatic ovarian cancer includes cancer in the fallopian tubes, cancer in organs of the abdomen such as cancer in the bowel, cancer in the uterus, cancer in the bladder, cancer in the rectum, cancer in the liver, cancer in the stomach, cancer in the colon, cancer in the diaphragm, cancer in the lungs, cancer in the lining of the abdomen or pelvis (peritoneum), and cancer in the brain. Similarly, metastatic lung cancer refers to cancer that has spread from the lungs to distant and/or several sites in the body and includes cancer in the liver, cancer in the adrenal glands, cancer in the bones, and cancer in the brain.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

According to the invention, a biological sample may be a tissue sample, including bodily fluids, and/or a cellular sample and may be obtained in the conventional manner such as by tissue biopsy, including punch biopsy, and by taking blood, bronchial aspirate, sputum, urine, feces or other body fluids. According to the invention, the term "biological sample" also includes processed biological samples such as fractions or isolates of biological samples, e.g. nucleic acid and peptide/protein isolates.

According to the invention, the term "immunoreactive cell" means a cell which can mature into an immune cell (such as B cell, T helper cell, or cytolytic T cell) with suitable stimulation. Immunoreactive cells comprise $CD34^+$ hematopoietic stem cells, immature and mature T cells and immature and mature B cells. If production of cytolytic or T helper cells recognizing a tumor antigen is desired, the immunoreactive cell is contacted with a cell expressing a tumor antigen under conditions which favor production, differentiation and/or selection of cytolytic T cells and of T helper cells. The differentiation of T cell precursors into a cytolytic T cell, when exposed to an antigen, is similar to clonal selection of the immune system.

The terms "T cell" and "T lymphocyte" are used interchangeably herein and include T helper cells (CD4+ T cells) and cytotoxic T cells (CTLs, CD8+ T cells) which comprise cytolytic T cells.

Some therapeutic methods are based on a reaction of the immune system of a patient, which results in a lysis of diseases cells such as cancer cells which present a tumor antigen with class I MHC. In this connection, for example autologous cytotoxic T lymphocytes specific for a complex of a tumor antigen peptide and an MHC molecule may be administered to a patient having a tumor disease. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting cytotoxic T lymphocytes, fluorogenic tetramers of MHC class I molecule/peptide complexes are used for obtaining specific clones of cytotoxic T lymphocytes (Altman et al., *Science* 274:94-96, 1996; Dunbar et al., *Curr. Biol.* 8:413-416, 1998).

Furthermore, cells presenting the desired complex (e.g. dendritic cells) may be combined with cytotoxic T lymphocytes of healthy individuals or another species (e.g. mouse) which may result in propagation of specific cytotoxic T lymphocytes with high affinity. The high affinity T cell receptor of these propagated specific T lymphocytes may be cloned and optionally humanized to a different extent, and the T cell receptors thus obtained then transduced via gene transfer, for example using retroviral vectors, into T cells of patients. Adoptive transfer may then be carried out using these genetically altered T lymphocytes (Stanislawski et al., Nat Immunol. 2:962-70, 2001; Kessels et al., Nat Immunol. 2:957-61, 2001).

Cytotoxic T lymphocytes may also be generated in vivo in a manner known per se. One method uses nonproliferative cells expressing an MHC class I/peptide complex. The cells used here will be those which usually express the complex, such as irradiated tumor cells or cells transfected with one or both genes necessary for presentation of the complex (i.e. the antigenic peptide and the presenting MHC molecule). Another preferred form is the introduction of the tumor antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining a tumor antigen or a tumor antigen peptide with an adjuvant in order to make incorporation into antigen-presenting cells in vivo possible. The tumor antigen or tumor antigen peptide may be represented as protein, as DNA (e.g. within a vector) or as RNA. The tumor antigen may be processed to produce a peptide partner for the MHC molecule, while a fragment thereof may be presented without the need for further processing. The latter is the case in particular, if these can bind to MHC molecules. Preference is given to administration forms in which the complete antigen is processed in vivo by a dendritic cell, since this may also produce T helper cell responses which are needed for an effective immune response (Ossendorp et al., *Immunol Lett.* 74:75-9, 2000; Ossendorp et al., *J. Exp. Med.* 187:693-702, 1998). In general, it is possible to administer an effective amount of the tumor antigen to a patient by intradermal injection, for example. However, injection may also be carried out intranodally into a lymph node (Maloy et al., *Proc Natl Acad Sci USA* 98:3299-303, 2001).

The pharmaceutical compositions and methods of treatment described according to the invention may also be used for immunization or vaccination to therapeutically treat or prevent a disease described herein. According to the invention, the terms "immunization" or "vaccination" preferably relate to an increase in or activation of an immune response to an antigen. It is possible to use animal models for testing an immunizing effect on cancer. For example, human cancer cells may be introduced into a mouse to generate a tumor. The effect on the cancer cells (for example reduction in tumor size) may be measured as a measure for the effectiveness of an immunization by an agent administered to the animal.

As part of the composition for an immunization or a vaccination, preferably one or more agents as described herein are administered together with one or more adjuvants for inducing an immune response or for increasing an immune response. An adjuvant is a substance which enhances an immune response. Adjuvants may enhance the immune response by providing an antigen reservoir (extracellularly or in macrophages), activating macrophages and/or stimulating particular lymphocytes. Adjuvants are known and comprise in a nonlimiting way monophosphoryl lipid A (MPL, SmithKline Beecham), saponins such as QS21 (SmithKline Beecham), DQS21 (SmithKline Beecham; WO 96/33739), QS7, QS17, QS18 and QS-L1 (So et al., Mol. Cells 7:178-186, 1997), incomplete Freund's adjuvant, complete Freund's adjuvant, vitamin E, montanide, alum, CpG oligonucleotides (cf. Kreig et al., Nature 374:546-9, 1995) and various water-in-oil emulsions prepared from biologically degradable oils such as squalene and/or tocopherol. Preferably, according to the invention, peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 µg to about 100 µg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise costimulating molecules provided in the form of proteins or nucleic acids such as B7-1 and B7-2 (CD80 and CD86, respectively).

Peptides may be administered in a manner known per se. In one embodiment, nucleic acids are administered by ex vivo methods, i.e. by removing cells from a patient, genetic modification of said cells in order to incorporate a nucleic acid and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker.

The invention also provides for administering nucleic acids in vivo by using, for example, vectors such as viruses and target-controlled liposomes.

In a preferred embodiment, a virus or viral vector for administering a nucleic acid is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Methods of introducing nucleic acids into cells in vitro or in vivo comprise transfection of nucleic acid calcium phosphate precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutically active compounds of the invention may be administered via any conventional route, including by injection or infusion. The administration may be carried out, for example, orally, intravenously, intraperitonealy, intramuscularly, subcutaneously or transdermally. Preferably, antibodies are therapeutically administered by way of a lung aerosol. Antisense nucleic acids are preferably administered by slow intravenous administration.

The compositions of the invention are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. According to the invention, a diagnosis or treatment of cancer may also include the diagnosis or treatment of cancer metastases which have already formed or will form. According to the invention, the term "treatment" comprises therapeutic and prophylactic treatment, i.e. prevention.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses of the compositions of the invention administered may depend on various of such parameters. In the case that a reaction in a patient is insufficient with an initial dose, higher doses (or effectively higher doses achieved by a different, more localized route of administration) may be used.

The pharmaceutical compositions of the invention are preferably sterile and contain an effective amount of the therapeutically active substance to generate the desired reaction or the desired effect.

Generally, doses of a peptide of from 1 ng to 1 mg, preferably from 10 ng to 100 µg, are formulated and administered. If the administration of nucleic acids (DNA and RNA) is desired, doses of from 1 ng to 0.1 mg may be formulated and administered.

The pharmaceutical compositions of the invention are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. The term "carrier" refers to an organic or inorganic component, of a natural or synthetic nature, in which the active component is combined in order to facilitate application. According to the invention, the term "pharmaceutically compatible carrier" includes one or more compatible solid or liquid fillers, diluents or encapsulating substances, which are suitable for administration to a patient. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

It should be emphasized that the term "comprises/comprising" when used in this specification is taken to specify the presence of stated features, integers, steps or components but does not preclude the presence or addition of one or more other features, integers, steps, components or groups thereof. The mere fact that certain measures are recited in mutually different dependent claims or described in different embodiments does not indicate that a combination of these measures cannot be used to advantage. However, the term "comprises/comprising" also includes embodiments consisting of stated features, integers, steps or components.

The present invention is described in detail by the figures and examples below, which are used only for illustration purposes and are not meant to be limiting.

Owing to the description and the examples, further embodiments which are likewise included in the invention are accessible to the skilled worker.

FIGURES

FIG. 1. Quantification of CLDN6 expression in normal and cancerous tissues by real-time RT-PCR. With the exception of placenta only trace amounts of CLDN6 transcripts could be detected in normal tissues. High expression of CLDN6 is found in samples from ovarian cancer (adenocarcinomas) and lung cancer (adenocarcinomas).

Figure 2:
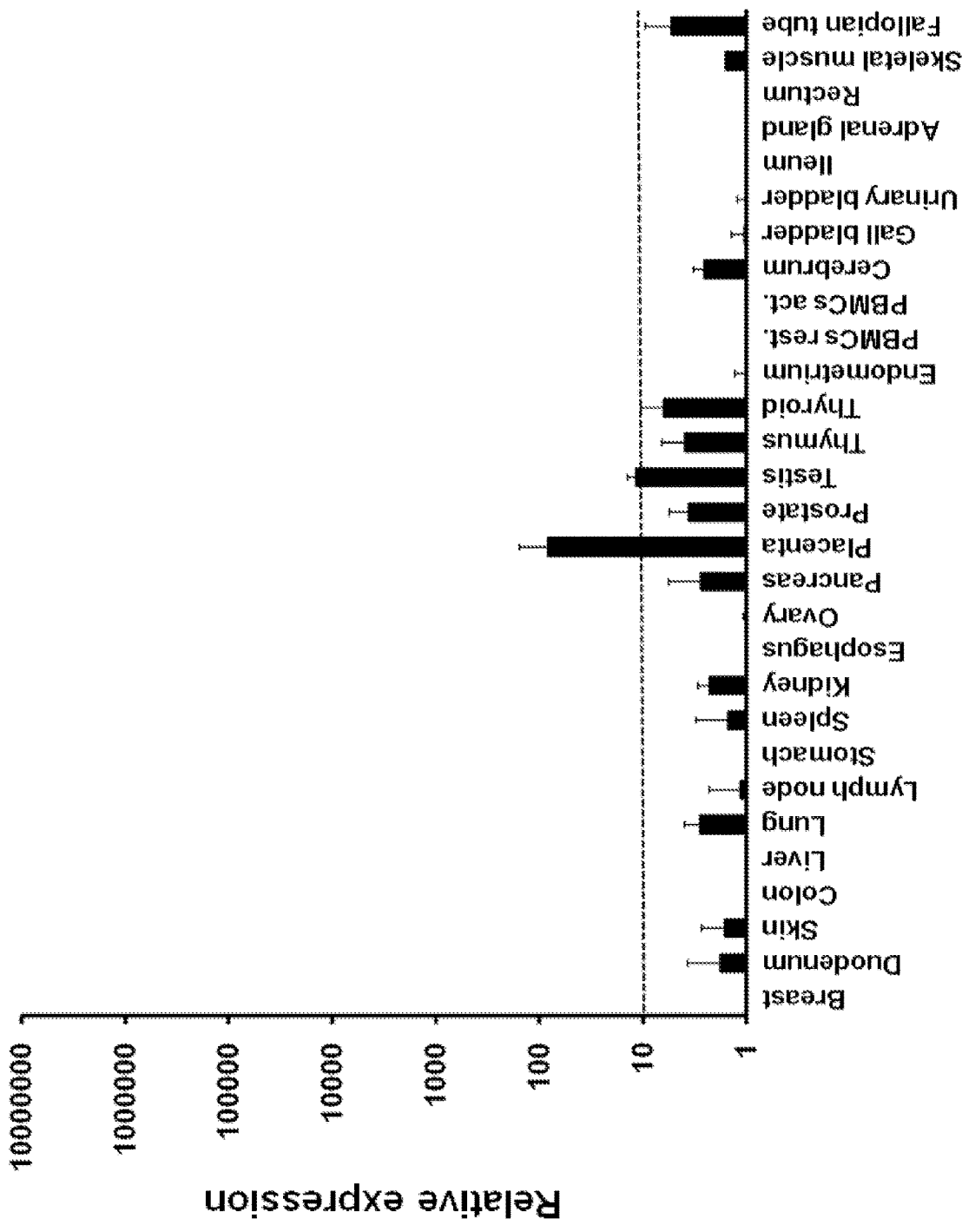
Figure 3A:
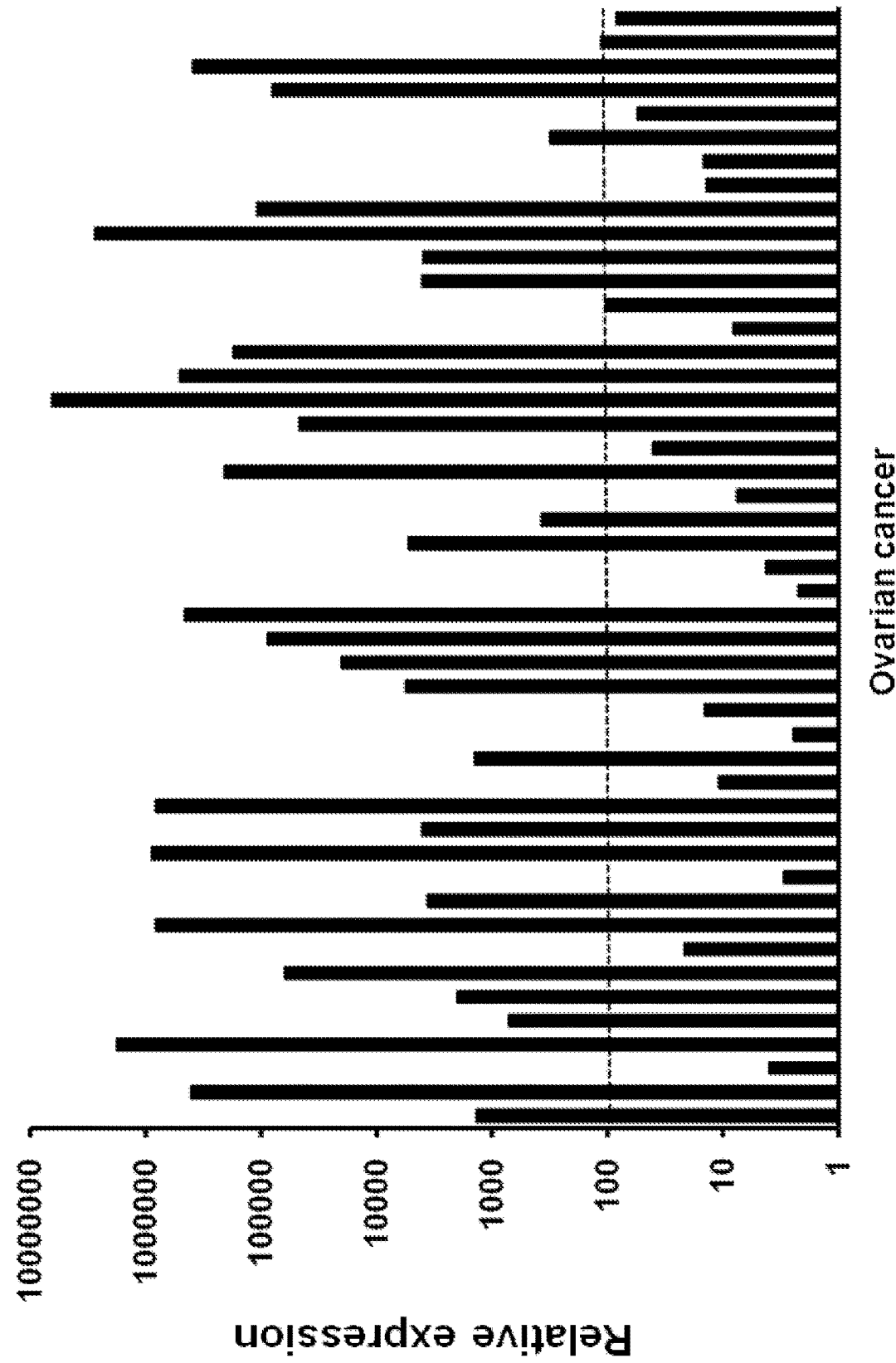
Figure 3B:
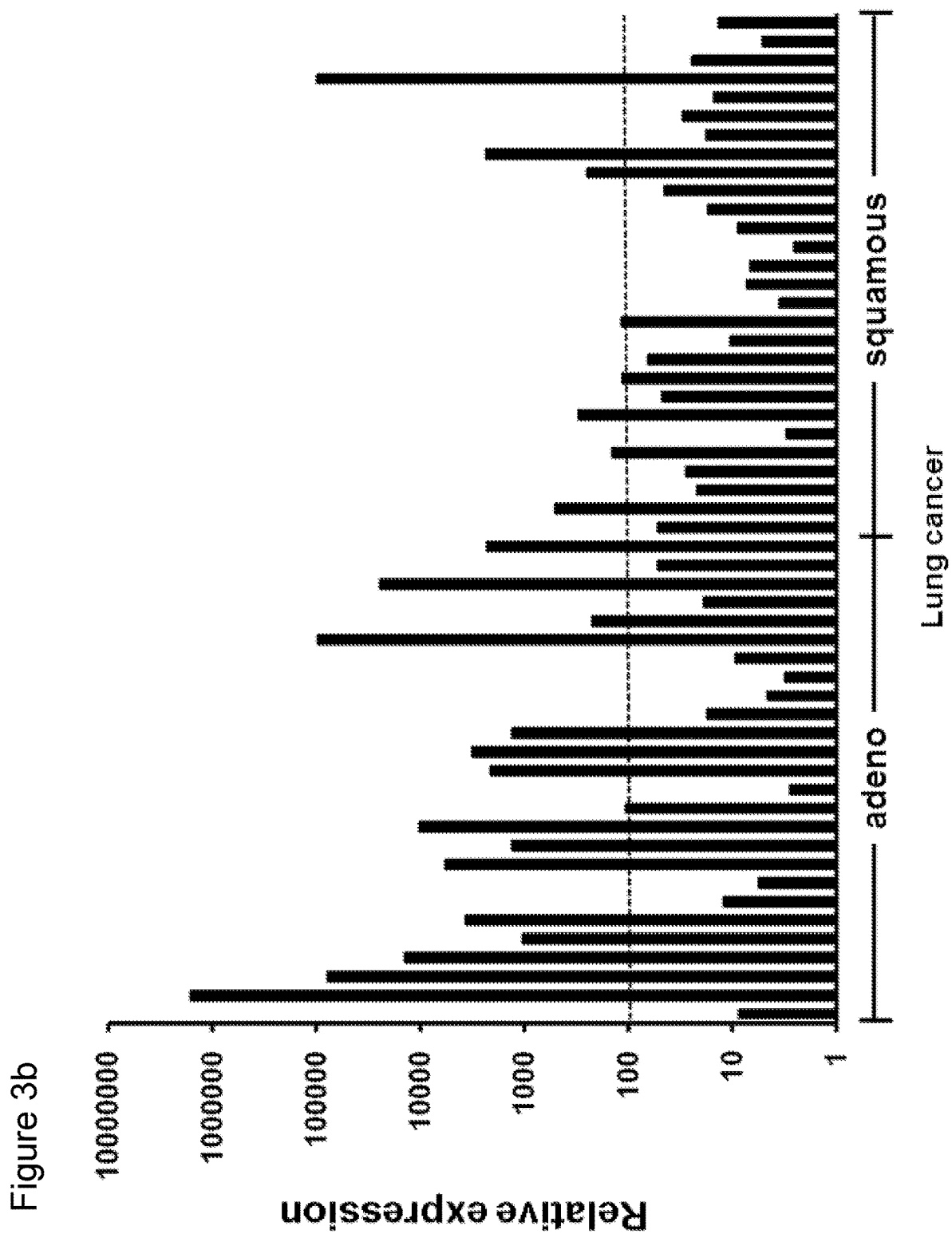
Figure 3C:
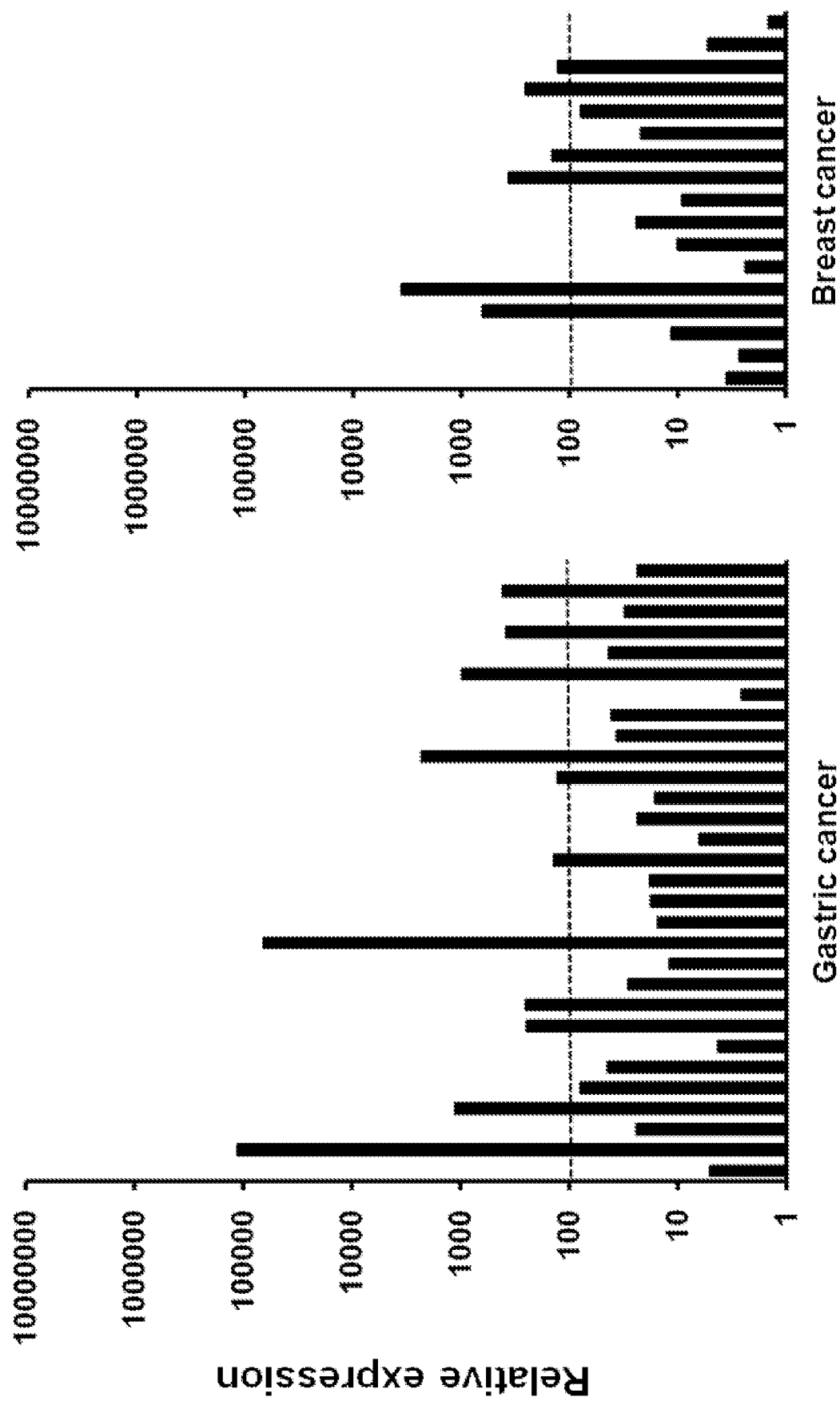
Figure 3D:
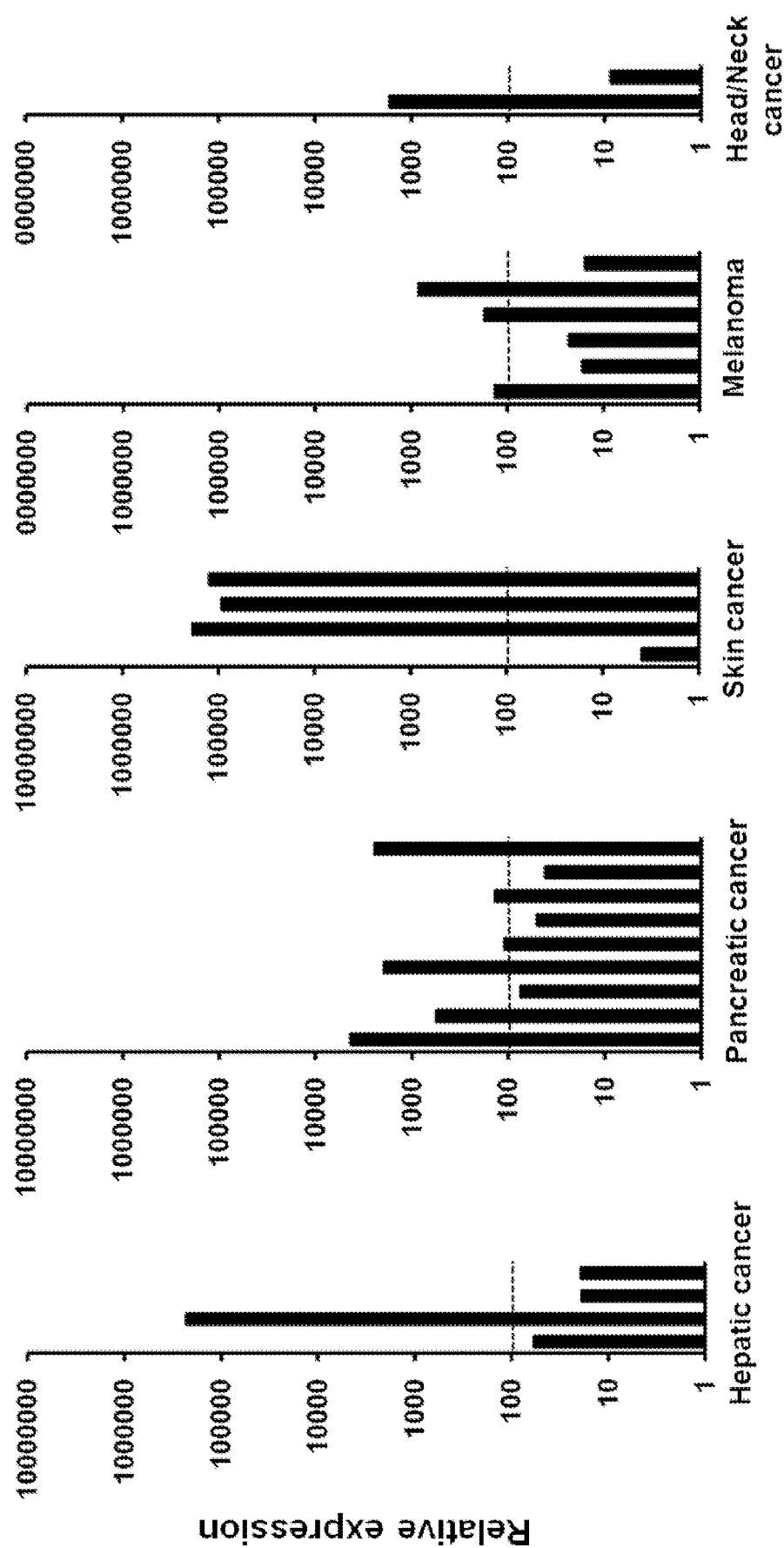
Figure 3E:
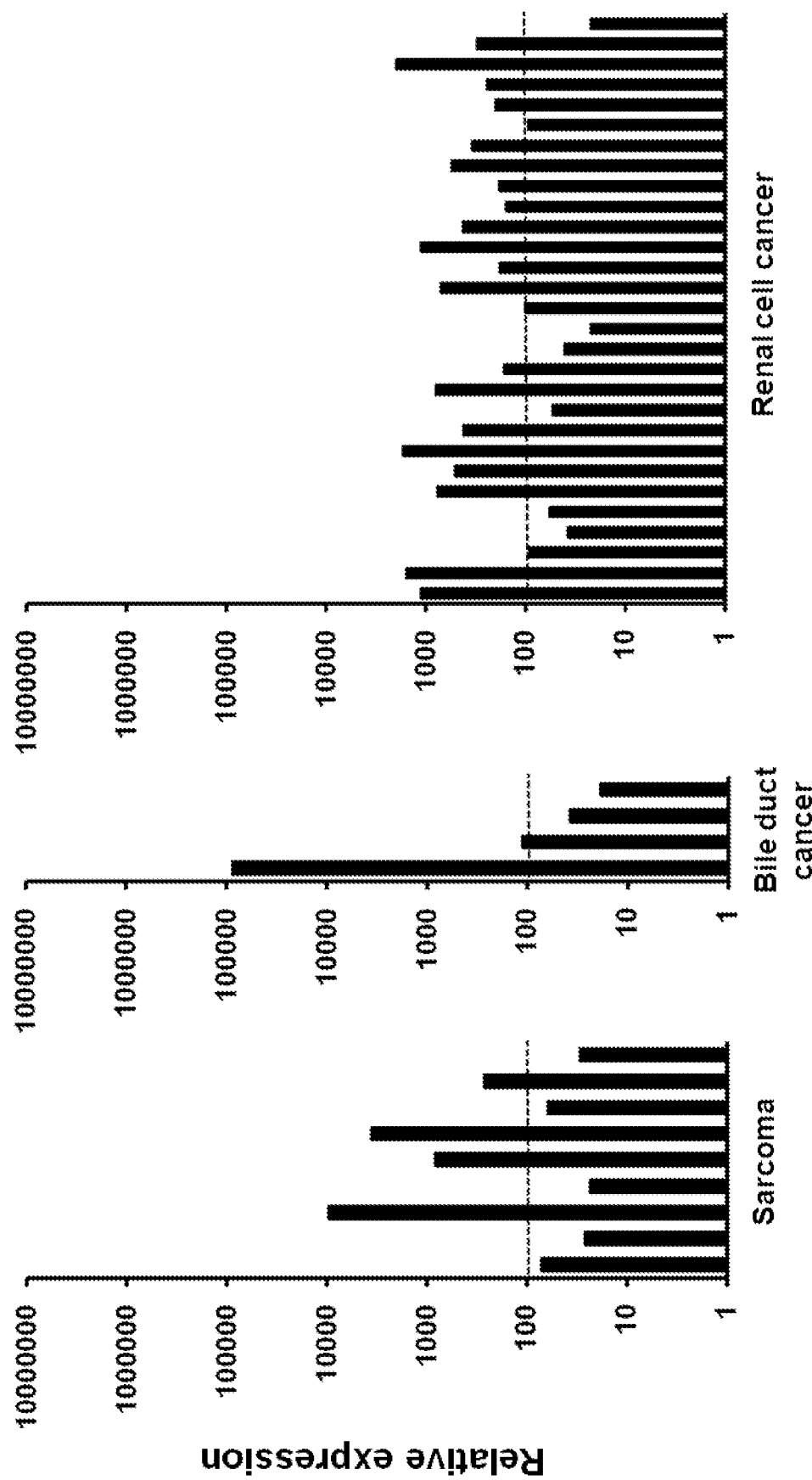
Figure 3F:
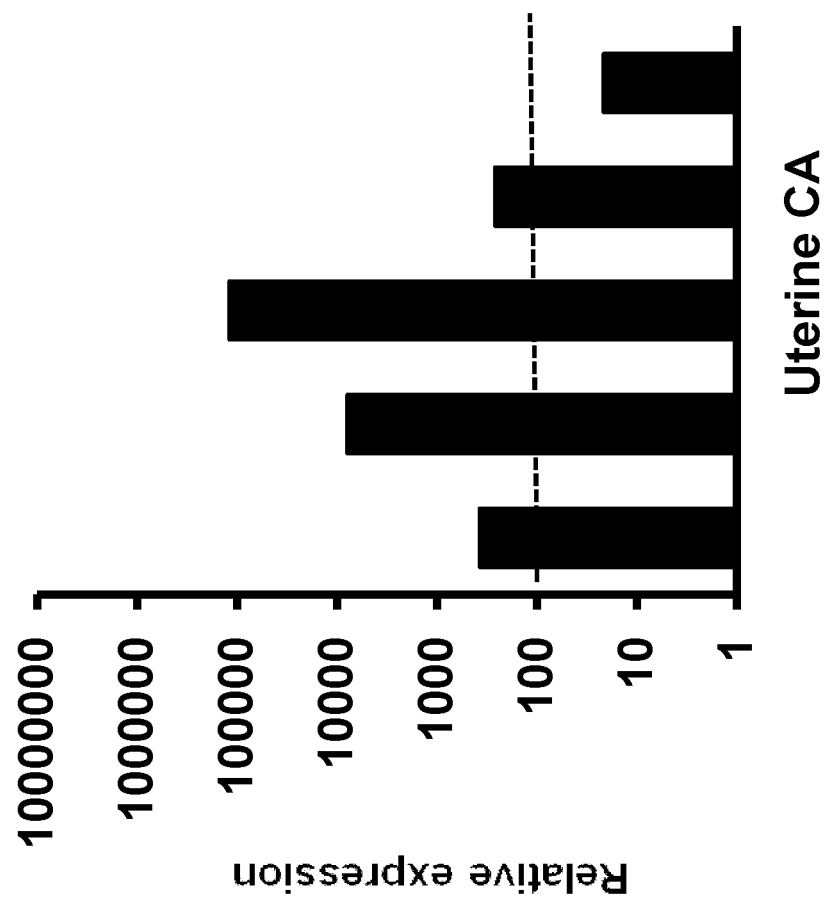
Figure 3G:
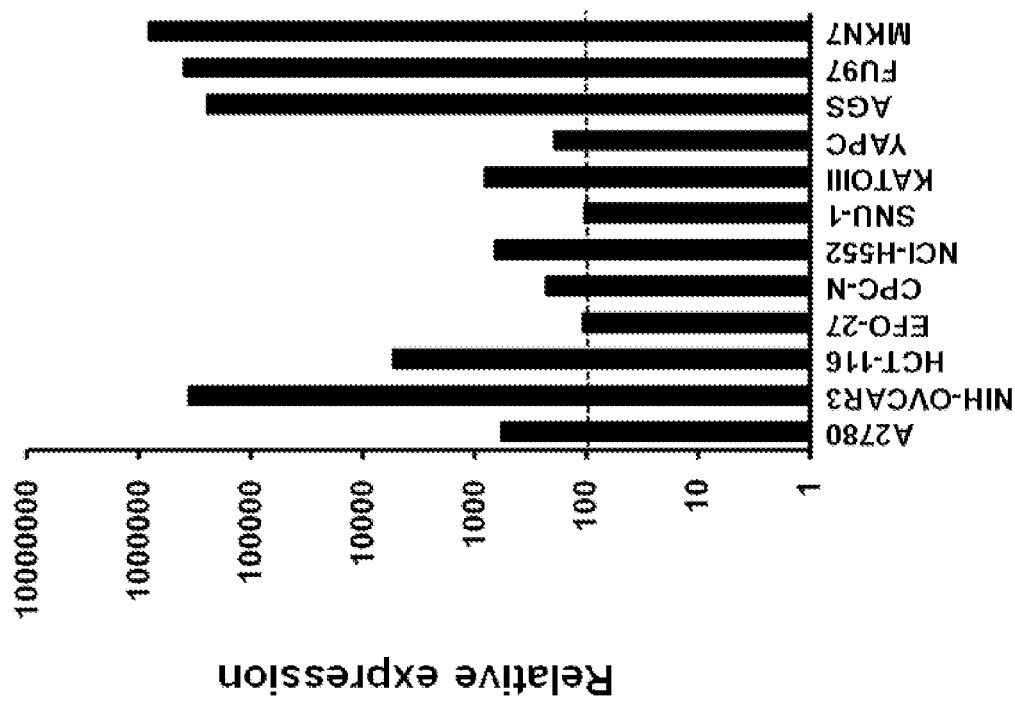
Figure 3H:
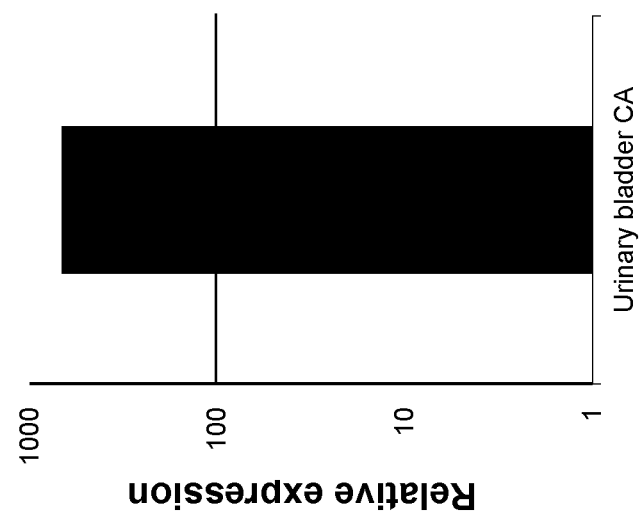

FIG. 2: Quantification of CLDN6 expression in normal tissues using real-time RT-PCR. Tissues from three individuals were tested for each normal tissue type. Only trace amounts of CLDN6 transcripts could be detected in normal tissues after 40 cycles of RT-PCR. The only normal tissue slightly exceeding the expression cutoff (dashed line, mean expression of all normal tissues +3 STDs (99% percentile)) was placenta. Error bars, STD.

FIG. 3A-3H: Quantification of CLDN6 expression in cancerous tissues and cell lines using real-time RT-PCR. In contrast to normal tissues, we found high expression of CLDN6 in samples from ovarian cancer (adenocarcinomas), lung cancer (NSCLC, with highest frequency and expression levels in adenocarcinomas), gastric cancer, breast cancer, hepatic cancer, pancreatic cancer, skin cancer (basal cell carcinoma and squamous cell carcinoma), malignant melanoma, head and neck cancer (malignant pleomorphic adenoma), sarcoma (synovial sarcoma and carcinosarcoma), bile duct cancer, renal cell cancer (clear cell carcinoma and papillary carcinoma), uterine cancer, urinary bladder cancer (papillary carcinoma) and cancer cell lines A2780 (ovarian cancer), NIH-OVCAR3 (ovarian cancer), HCT-116 (colon cancer), EFO-27 (ovarian cancer), CPC-N (SCLC), NCI-H552 (NSCLC), SNU-1 (gastric cancer), KATOIII (gastric cancer), YAPC (pancreatic cancer), AGS (gastric cancer), FU97 (gastric cancer), MKN7 (gastric cancer). In order not to overestimate CLDN6 expression frequency in cancerous tissues and cell lines only transcript levels at least 10-fold above normal tissue expression cutoff were classified as positive (dashed line).

FIG. 4: Western blot analysis of CLDN6 expression in normal tissues. Tissue lysates from up to five individuals were tested for each normal tissue type. No CLDN6 protein expression was detected in any of the normal tissues analyzed. NIH-OVCAR3, positive control.

Figure 5:
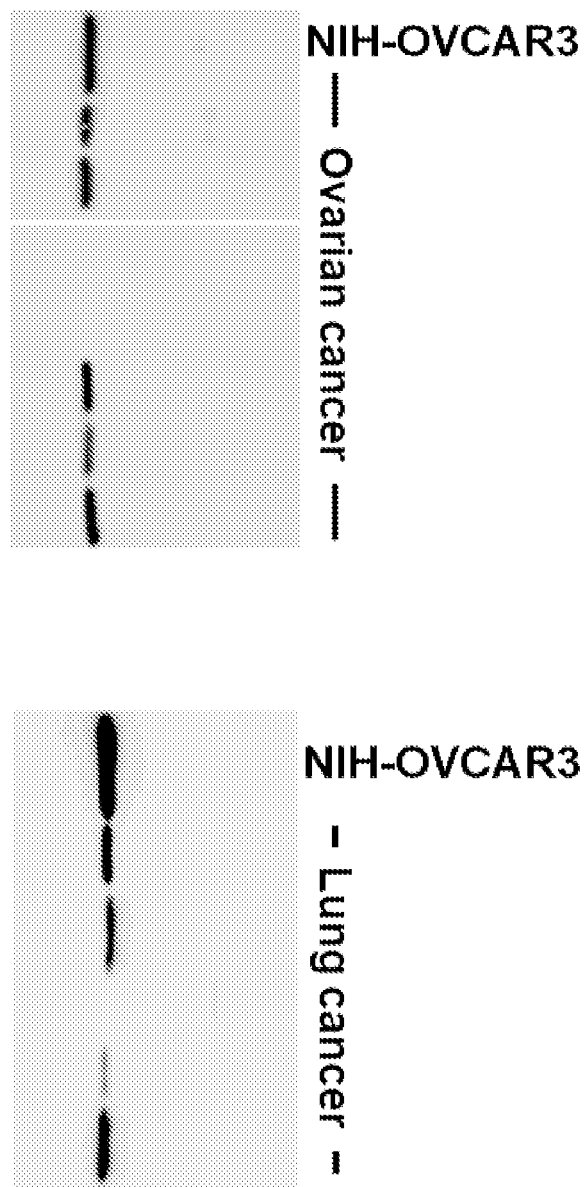

FIG. 5: Western blot analysis of CLDN6 expression in cancerous tissues. In contrast to normal tissues, high expression of CLDN6 protein was detected in samples from ovarian cancer and lung cancer. NIH-OVCAR3, positive control.

Figure 6:
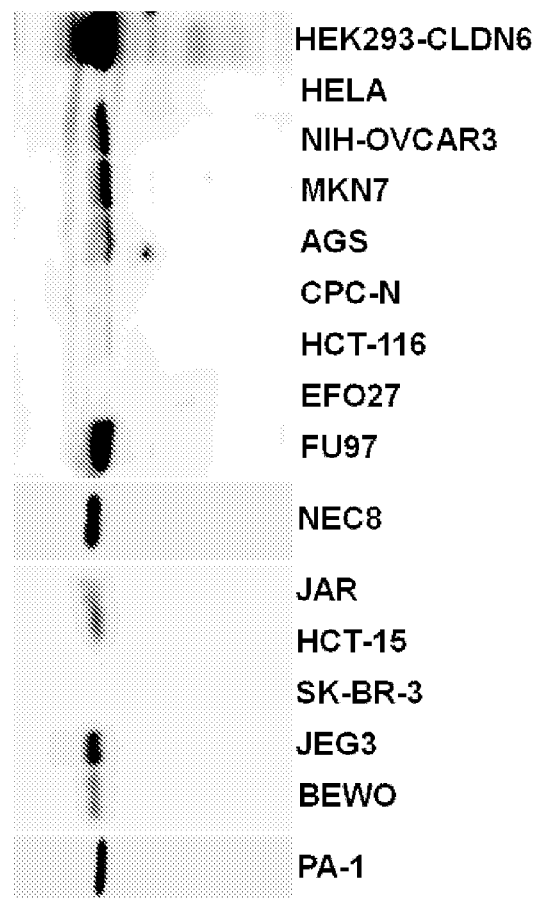

FIG. 6: Western blot analysis of CLDN6 expression in cancer cell lines. CLDN6 expression was detected in HEK293 cells transfected with CLDN6 expression plasmid (positive control), NIH-OVCAR3 (ovarian cancer), MKN7 (gastric cancer), AGS (gastric cancer), CPC-N (SCLC), HCT-116 (colon cancer), FU97 (gastric cancer), NEC8 (testicular embryonal carcinoma), JAR (placental choriocarcinoma), JEG3 (placental choriocarcinoma), BEWO (placental choriocarcinoma), and PA-1 (ovarian teratocarcinoma).

Figure 7:
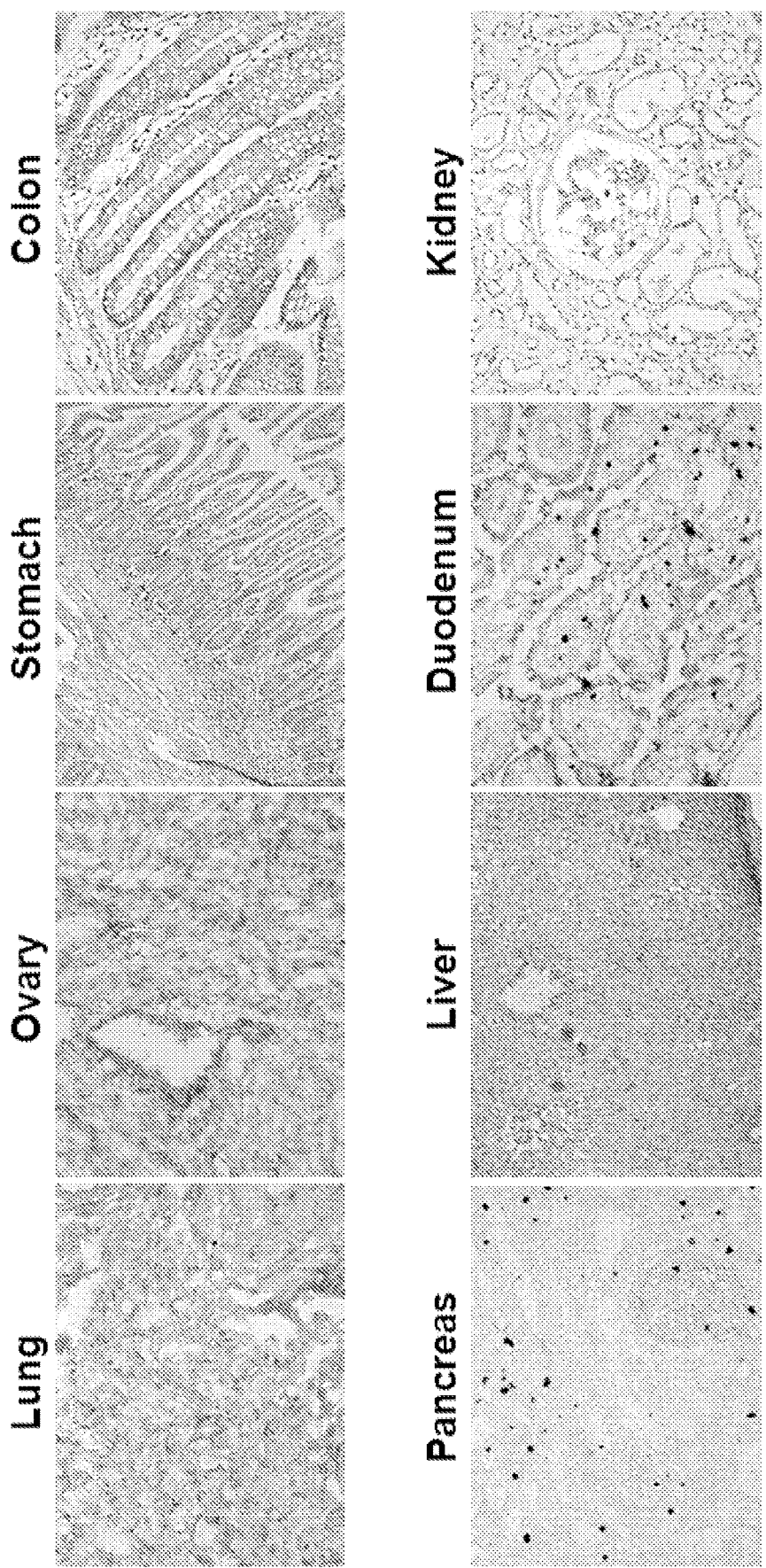

FIG. 7: Immunohistochemical (IHC) analysis of CLDN6 expression in normal tissues. No CLDN6 protein expression was detectable in any of the tissues analyzed. The dark marks visible in pancreas, duodenum and kidney represent dye precipitates not associated with cellular structures.

FIG. 8A-8H: Immunohistochemical (IHC) analysis of CLDN6 expression in cancerous tissues. In contrast to normal tissues, strong or at least significant staining was observed on tissue sections from (A) ovarian cancer, (B) lung cancer, (C) skin cancer, (D) pancreatic cancer, gastric cancer, (E) breast cancer, urinary bladder cancer (transitional cell carcinoma), (F) cervical cancer, testicular cancer (seminoma), (G) uterine cancer, small bowel cancer and (H) testicular cancer (embryonal and teratoma). Staining was clearly accentuated at the plasma membrane of the malignant epithelial cell populations, whereas adjacent stromal and non-malignant epithelial cells were negative. These results indicate that CLDN6 protein is localized at the plasma membrane of malignant cells.

Figure 9:
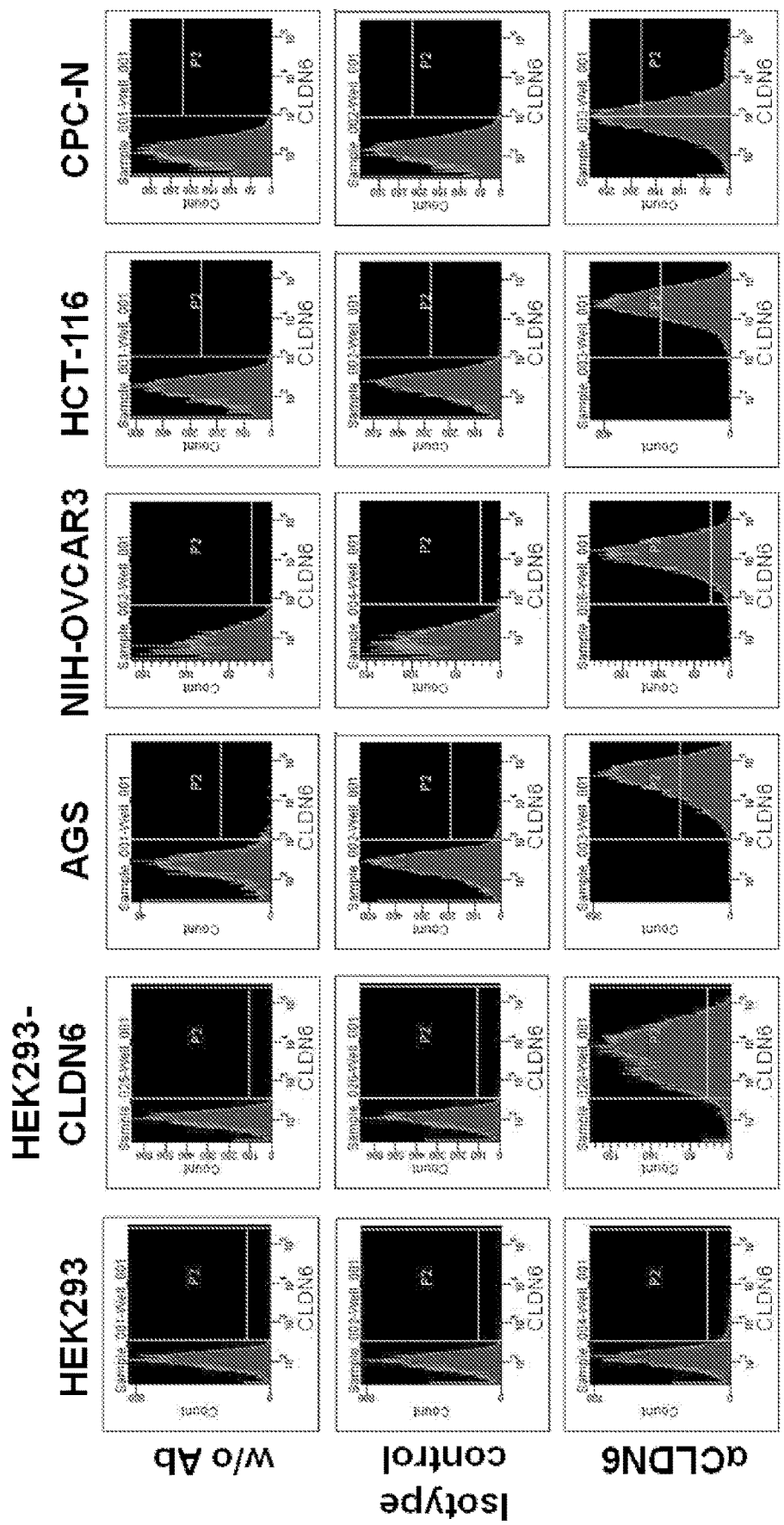

FIG. 9: Flowcytometric analysis of CLDN6 expression in cancer cells. Native cells were stained using a commercial monoclonal antibody targeting an extracellular domain of CLDN6 (αCLDN6). As control HEK293 cells transfected with a CLDN6 expression plasmid and untransfected HEK293 cells were used. No labeling of untransfected control cells was observed, however, strong labeling was observed in CLDN6 transfected control cells and in endogenously CLDN6 expressing AGS (gastric cancer), NIH-OVCAR3 (ovarian cancer), HCT-116 (colon cancer), and CPC-N (SCLC) cancer cells. These results clearly show that CLDN6 is localized at the plasma membrane of cancer cells and can be targeted by monoclonal antibodies directed against an extracellular protein domain.

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Example 1

CLDN6 is a Marker Which is Specific for Ovarian Tumors and Lung Tumors

CLDN6 (nucleic acid sequence according to SEQ ID NO: 1, amino acid sequence according to SEQ ID NO: 2) expression was quantified in normal tissues and samples from ovarian cancer and lung cancer (adenocarcinomas) using real-time RT-PCR.

For RNA extraction, first-strand cDNA synthesis and real-time reverse transcription-PCR (RT-PCR) were performed as previously described (Koslowski et al, 2006; Koslowski et al, 2007). Real-time quantitative expression analysis was performed in triplicates in a 40 cycle RT-PCR. After normalization to HPRT (sense 5'-TGA CAC TGG CAA AAC AAT GCA-3'; antisense 5'-GGT CCT TTT CAC CAG CAA GCT-3', 62° C. annealing) expression of CLDN6 (sense 5'-CTT ATC TCC TTC GCA GTG CAG-3'; antisense 5'-AAG GAG GGC GAT GAC ACA GAG-3', 60° C. annealing) was quantified using ΔΔCT calculation. Tissues from up to three individuals were tested for each normal tissue type.

With the exception of placenta only trace amounts of CLDN6 transcripts could be detected in normal tissues. In contrast, we found high expression of CLDN6 in samples from ovarian cancer (adenocarcinomas) and lung cancer (adenocarcinomas); see FIG. 1.

Example 2

Quantification of CLDN6 Expression in Normal Tissues, Cancerous Tissues and Cell Lines Using Real-Time RT-PCR Total cellular RNA was extracted from frozen tissue specimens and cancer cell lines using RNeasy Mini Kit (Qiagen), primed with a $dT_{18}$ oligonucleotide and reverse-transcribed with Superscript II (GIBCO/Lifetech) according to the manufacturer's instructions. Integrity of the obtained cDNA was tested by amplification of p53 transcripts in a 30 cycle PCR (sense, 5'-CGTGAGCGCTTCGAGATG-TTCCG-3'; antisense, 5'-CCTAACCAGCTGCC-CAACTGTAG-3'; annealing temperature 67° C.). After normalization to HPRT (sense 5'-TGA CAC TGG CAA AAC AAT GCA-3'; antisense 5'-GGT CCT TTT CAC CAG CAA GCT-3', 62° C. annealing) expression of CLDN6 (sense 5'-CTT ATC TCC TTC GCA GTG CAG-3'; antisense 5'-AAG GAG GGC GAT GAC ACA GAG-3', 60° C. annealing) was quantified using ΔΔCT calculation.

Tissues from three individuals were tested for each normal tissue type. Only trace amounts of CLDN6 transcripts could be detected in normal tissues after 40 cycles of RT-PCR; see FIG. 2. The only normal tissue slightly exceeding the expression cutoff (dashed line, mean expression of all normal tissues +3 STDs (99% percentile)) was placenta. Error bars, STD.

In contrast to normal tissues, we found high expression of CLDN6 in samples from ovarian cancer (adenocarcinomas), lung cancer (NSCLC, with highest frequency and expression levels in adenocarcinomas), gastric cancer, breast cancer, hepatic cancer, pancreatic cancer, skin cancer (basal cell carcinoma and squamous cell carcinoma), malignant melanoma, head and neck cancer (malignant pleomorphic adenoma), sarcoma (synovial sarcoma and carcinosarcoma), bile duct cancer, renal cell cancer (clear cell carcinoma and papillary carcinoma), uterine cancer, urinary bladder cancer (papillary carcinoma) and cancer cell lines A2780 (ovarian cancer), NIH-OVCAR3 (ovarian cancer), HCT-116 (colon cancer), EFO-27 (ovarian cancer), CPC-N (SCLC), NCI-H552 (NSCLC), SNU-1 (gastric cancer), KATOIII (gastric cancer), YAPC (pancreatic cancer), AGS (gastric cancer), FU97 (gastric cancer), MKN7 (gastric cancer); see FIG. 3a-g. In order not to overestimate CLDN6 expression frequency in cancerous tissues and cell lines only transcript levels at least 10-fold above normal tissue expression cutoff were classified as positive (dashed line).

Example 3

Quantification of CLDN6 Expression in Normal Tissues, Cancerous Tissues and Cell Lines Using Western Blot Analysis For Western blot analysis 20 μg of total protein extracted from cells lyzed with Laemmli-lysis buffer was used. Extracts were diluted in reducing sample buffer (Roth), subjected to SDS-PAGE and subsequently electrotransferred onto PVDF membrane (Pall). Immunostaining was performed with polyclonal antibodies reactive to CLDN6 (ARP) and beta-Actin (Abcam) followed by detection of primary antibodies with horseradish-peroxidase conjugated goat anti-mouse and goat anti-rabbit secondary antibodies (Dako).

Tissue lysates from up to five individuals were tested for each normal tissue type. No CLDN6 protein expression was detected in any of the normal tissues analyzed; see FIG. 4. NIH-OVCAR3, positive control.

In contrast to normal tissues, high expression of CLDN6 protein was detected in samples from ovarian cancer and lung cancer; see FIG. 5. NIH-OVCAR3, positive control.

CLDN6 expression was detected in HEK293 cells transfected with CLDN6 expression plasmid (positive control), NIH-OVCAR3 (ovarian cancer), MKN7 (gastric cancer), AGS (gastric cancer), CPC-N (SCLC), HCT-116 (colon cancer), FU97 (gastric cancer), NEC8 (testicular embryonal carcinoma), JAR (placental choriocarcinoma), JEG3 (placental choriocarcinoma), BEWO (placental choriocarcinoma), and PA-1 (ovarian teratocarcinoma); see FIG. 6.

Example 4

Immunohistochemical (IHC) Analysis of CLDN6 Expression in Normal Tissues and Cancerous Tissues Paraffin-embedded tissue sections (4 μm) were incubated for 1 hour at 58° C. on a heating plate (HI 1220, Leica). Paraffin was removed from the sections by incubating the slides in Roticlear (Roth) for 2×10 min at RT. Afterwards the sections were rehydrated in graded alcohol (99%, 2×96%, 80% and 70%, 5 min each). Antigen retrieval was performed by boiling slides at 120° C. (15 psi) for 15 min in 10 mM citrate buffer (pH 6.0)+0.05% Tween-20. Directly after boiling slides were incubated in PBS for 5 min. Endogenous peroxidase activity was blocked with 0.3% hydrogen peroxide in MeOH for 15 min at RT. To avoid non-specific binding the slides were blocked with 10% goat serum in PBS for 30 min at RT. Thereafter, the slides were incubated with CLDN6-specific polyclonal antibody (1 μg/ml) (ARP) overnight at 4° C. On the next day the slides were washed with PBS at RT (3×5 min) and incubated with 100 μl of the secondary antibodies (PowerVision poly HRP-Anti-Rabbit IgG ready-to-use (ImmunoLogic)) for one hour at RT. Afterwards, slides were washed with PBS at RT (3×5 min). Final staining was performed by using the VECTOR Nova-RED Substrate Kit SK-4800 from Vector Laboratories (Burlingame). Sections were counterstained with haematoxylin for 90 sec at RT. After dehydration with graded alcohol (70%, 80%, 2×96% and 99%, 5 min each) and 10 min incubation in Xylol slides were mounted with X-tra Kit (Medite Histotechnic).

No CLDN6 protein expression was detectable in any of the tissues analyzed; see FIG. 7. The dark marks visible in pancreas, duodenum and kidney represent dye precipitates not associated with cellular structures.

In contrast to normal tissues, strong or at least significant staining was observed on tissue sections from (a) ovarian cancer, (b) lung cancer, (c) skin cancer, (d) pancreatic cancer, gastric cancer, (e) breast cancer, urinary bladder cancer (transitional cell carcinoma), (f) cervical cancer, testicular cancer (seminoma), (g) uterine cancer, small bowel cancer and (h) testicular cancer (embryonal and teratoma); see FIG. 8a-h. Staining was clearly accentuated at the plasma membrane of the malignant epithelial cell populations, whereas adjacent stromal and non-malignant epithelial cells were negative. These results indicate that CLDN6 protein is localized at the plasma membrane of malignant cells.

Example 5

Flowcytometric Analysis of CLDN6 Expression in Cancer Cells

Cells were harvested with 5 mM EDTA/PBS and resuspended in PBS/2% FCS/0.1% Na Acid. 2×10⁵ cells were incubated with a mouse monoclonal antibody targeting an extracellular domain of CLDN6 (R&D) at 4° C. for 30 min. After washing cells were incubated with an APC-labeled goat-anti mouse secondary antibody (Jackson ImmunoResearch Laboratories) at 4° C. for 30 min. After washing cells were stained with propidium iodide (PI). Analysis was done after gating on live (PI-negative cells) using the BD FACSArray Bioanalyzer System.

Native cells were stained using a commercial monoclonal antibody targeting an extracellular domain of CLDN6 (αCLDN6). As control HEK293 cells transfected with a CLDN6 expression plasmid and untransfected HEK293 cells were used. No labeling of untransfected control cells was observed, however, strong labeling was observed in CLDN6 transfected control cells and in endogenously CLDN6 expressing AGS (gastric cancer), NIH-OVCAR3 (ovarian cancer), HCT-116 (colon cancer), and CPC-N (SCLC) cancer cells; see FIG. 9. These results clearly show that CLDN6 is localized at the plasma membrane of cancer cells and can be targeted by monoclonal antibodies directed against an extracellular protein domain.

The invention claimed is:

1. A method of treating a patient having a tumor disease that expresses a tumor antigen encoded by a nucleic acid sequence according to SEQ ID NO: 1 or a variant of said nucleic acid sequence,
   wherein the method comprises administering to the patient a pharmaceutical composition comprising an antibody that specifically binds a tumor antigen encoded by a nucleic acid according to SEQ ID NO: 1, wherein the tumor disease is a testicular cancer.

2. The method of claim 1, wherein the antibody is a monoclonal, chimeric, human or humanized antibody, or is an antigen binding fragment of an antibody or a synthetic antibody.

3. The method of claim 1, wherein the antibody is a monoclonal, chimeric, human or humanized antibody.

4. The method of claim 1, wherein the antibody is attached to one or more therapeutic effector moieties selected from the group consisting of a radiolabel, cytotoxin, and cytotoxic enzyme.

5. The method of claim 1, wherein the testicular cancer is selected from the group consisting of germ cell tumors, testicular seminoma, testicular teratoma, embryonic testicular cancer, and testicular embryonal carcinoma.

6. A method of treating a patient who has been diagnosed with a tumor disease associated with a tumor antigen comprising an amino acid sequence encoded by a nucleic acid sequence of SEQ ID NO: 1 or a variant of said nucleic acid sequence,
   wherein the method comprises administering to the patient a pharmaceutical composition comprising an antibody that specifically binds a tumor antigen encoded by a nucleic acid according to SEQ ID NO: 1, wherein the tumor disease is a testicular cancer.

7. The method of claim 6, wherein the antibody is a monoclonal, chimeric, human or humanized antibody, or is an antigen binding fragment of an antibody or a synthetic antibody.

8. The method of claim 6, wherein the antibody is a monoclonal, chimeric, human or humanized antibody.

9. The method of claim 6, wherein the antibody is attached to one or more therapeutic effector moieties selected from the group consisting of a radiolabel, cytotoxin, and cytotoxic enzyme.

10. The method of claim 6, wherein the testicular cancer is selected from the group consisting of germ cell tumors, testicular seminoma, testicular teratoma, embryonic testicular cancer, and testicular embryonal carcinoma.

* * * * *

```
                        SEQUENCE LISTING

<160> NUMBER OF SEQ ID NOS: 11

<210> SEQ ID NO 1
<211> LENGTH: 1369
<212> TYPE: DNA
<213> ORGANISM: Homo sapiens

<400> SEQUENCE: 1
cgacactcgg cctaggaatt tcccttatct ccttcgcagt gcagctcctt caacctcgcc     60
atggcctctg ccggaatgca gatcctggga gtcgtcctga cactgctggg ctgggtgaat    120
ggcctggtct cctgtgccct gcccatgtgg aaggtgaccg ctttcatcgg caacagcatc    180
gtggtggccc aggtggtgtg ggagggcctg tggatgtcct gcgtggtgca gagcaccggc    240
cagatgcagt gcaaggtgta cgactcactg ctggcgctgc cacaggacct gcaggctgca    300
cgtgccctct gtgtcatcgc cctccttgtg gccctgttcg gcttgctggt ctaccttgct    360
ggggccaagt gtaccacctg tgtggaggag aaggattcca aggcccgcct ggtgctcacc    420
tctgggattg tctttgtcat ctcaggggtc ctgacgctaa tccccgtgtg ctggacggcg    480
catgccatca tccgggactt ctataacccc ctggtggctg aggcccaaaa gcgggagctg    540
ggggcctccc tctacttggg ctgggcgcc tcaggccttt gttgctggg tgggggttg     600 ctgtgctgca cttgccccctc ggggggtcc cagggcccca gccattacat ggcccgctac    660
tcaacatctg ccctgccat ctctcgggggg ccctctgagt accctaccaa gaattacgtc    720
tgacgtggag gggaatgggg gctccgctgg cgctagagcc atccagaagt ggcagtgccc    780
aacagctttg ggatgggttc gtacctttg tttctgcctc ctgctattt tcttttgact     840 gaggatattt aaaattcatt tgaaaactga gccaaggtgt tgactcagac tctcacttag    900
gctctgctgt ttctcaccct tggatgatgg agccaaagag gggatgcttt gagattctgg    960
atcttgacat gccatctta gaagccagtc aagctatgga actaatgcgg aggctgcttg   1020
ctgtgctggc tttgcaacaa gacagactgt ccccaagagt tcctgctgct gctggggct   1080 gggcttccct agatgtcact ggacagctgc cccccatcct actcaggtct ctggagctcc   1140
tctcttcacc cctggaaaaa caaatgatct gttaacaaag gactgcccac ctccggaact   1200
tctgacctct gtttcctccg tcctgataag acgtccaccc cccagggcca ggtcccagct   1260
atgtagaccc ccgcccccac ctccaacact gcaccttct gccctgcccc cctcgtctca   1320
ccccctttac actcacattt ttatcaaata aagcatgttt tgttagtgc                1369
```

<210> SEQ ID NO 2
<211> LENGTH: 220
<212> TYPE: PRT
<213> ORGANISM: Homo sapiens

<400> SEQUENCE: 2

```
Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220
```

<210> SEQ ID NO 3
<211> LENGTH: 53
<212> TYPE: PRT
<213> ORGANISM: Homo sapiens

<400> SEQUENCE: 3

```
Pro Met Trp Lys Val Thr Ala Phe Ile Gly Asn Ser Ile Val Val Ala
1               5                   10                  15

Gln Val Val Trp Glu Gly Leu Trp Met Ser Cys Val Val Gln Ser Thr
            20                  25                  30

Gly Gln Met Gln Cys Lys Val Tyr Asp Ser Leu Leu Ala Leu Pro Gln
        35                  40                  45

Asp Leu Gln Ala Ala
    50
```

<210> SEQ ID NO 4
<211> LENGTH: 33
<212> TYPE: PRT
<213> ORGANISM: Homo sapiens

<400> SEQUENCE: 4

```
Glu Gly Leu Trp Met Ser Cys Val Val Gln Ser Thr Gly Gln Met Gln
```

```
1               5                   10                  15
Cys Lys Val Tyr Asp Ser Leu Leu Ala Leu Pro Gln Asp Leu Gln Ala
            20                  25                  30

Ala

<210> SEQ ID NO 5
<211> LENGTH: 13
<212> TYPE: PRT
<213> ORGANISM: Homo sapiens

<400> SEQUENCE: 5

Arg Asp Phe Tyr Asn Pro Leu Val Ala Glu Ala Gln Lys
1               5                   10

<210> SEQ ID NO 6
<211> LENGTH: 21
<212> TYPE: DNA
<213> ORGANISM: Artificial
<220> FEATURE:
<223> OTHER INFORMATION: Oligonucleotide

<400> SEQUENCE: 6
cttatctcct tcgcagtgca g                                          21

<210> SEQ ID NO 7
<211> LENGTH: 21
<212> TYPE: DNA
<213> ORGANISM: Artificial
<220> FEATURE:
<223> OTHER INFORMATION: Oligonucleotide

<400> SEQUENCE: 7
aaggagggcg atgacacaga g                                          21

<210> SEQ ID NO 8
<211> LENGTH: 21
<212> TYPE: DNA
<213> ORGANISM: Artificial
<220> FEATURE:
<223> OTHER INFORMATION: Oligonucleotide

<400> SEQUENCE: 8
tgacactggc aaaacaatgc a                                          21

<210> SEQ ID NO 9
<211> LENGTH: 21
<212> TYPE: DNA
<213> ORGANISM: Artificial
<220> FEATURE:
<223> OTHER INFORMATION: Oligonucleotide

<400> SEQUENCE: 9
ggtccttttc accagcaagc t                                          21

<210> SEQ ID NO 10
<211> LENGTH: 23
<212> TYPE: DNA
<213> ORGANISM: Artificial
<220> FEATURE:
<223> OTHER INFORMATION: Oligonucleotide

<400> SEQUENCE: 10
cgtgagcgct tcgagatgtt ccg                                        23
```

```
<210> SEQ ID NO 11
<211> LENGTH: 23
<212> TYPE: DNA
<213> ORGANISM: Artificial
<220> FEATURE:
<223> OTHER INFORMATION: Oligonucleotide

<400> SEQUENCE: 11
cctaaccagc tgcccaactg tag                                              23
```